United States Patent [19]

Haynes et al.

[11] Patent Number: 5,993,819
[45] Date of Patent: *Nov. 30, 1999

[54] SYNTHETIC VACCINE FOR PROTECTION AGAINST HUMAN IMMUNODEFICIENCY VIRUS INFECTION

[75] Inventors: Barton F. Haynes; Thomas J. Palker, both of Durham, N.C.

[73] Assignee: Duke University, Durham, N.C.

[ * ] Notice: This patent is subject to a terminal disclaimer.

[21] Appl. No.: 08/546,515

[22] Filed: Oct. 20, 1995

Related U.S. Application Data

[63] Continuation-in-part of application No. 08/235,305, Apr. 29, 1994, abandoned, which is a continuation-in-part of application No. 07/858,361, Mar. 27, 1992, abandoned, which is a continuation-in-part of application No. 07/832,849, Feb. 10, 1992, abandoned, which is a continuation-in-part of application No. 07/591,109, Oct. 1, 1990, abandoned, which is a continuation-in-part of application No. 07/093,854, Sep. 8, 1987, Pat. No. 5,019,387.

[51] Int. Cl.⁶ .......................... A61K 39/21; A61K 39/38; A61K 39/12; C07K 1/00
[52] U.S. Cl. .................. 424/188.1; 424/184.1; 424/208.1; 424/204.1; 530/350; 530/325; 530/326; 530/324
[58] Field of Search .............................. 424/188.1, 184.1, 424/208.1, 204.1; 530/350, 325, 326, 324

[56] References Cited

U.S. PATENT DOCUMENTS 5,013,548   5/1991   Haynes et al. ............................ 424/89
5,019,387   5/1991   Haynes et al. ............................ 424/89

FOREIGN PATENT DOCUMENTS 9104051   4/1991   WIPO .

OTHER PUBLICATIONS

Palker, et al, 1988, "Type specific neutral . . . " PNAS 85: 1932–1936.
Hart, et al, "Synthetic Peptides . . . ", J. Immunol. 145(8): 2677–2685, 1990.
Javaherian, et al, 1989, "Principal Neutralizing Determinant . . . " PNAS 86: 6768–6772.
Palker, et al, "Polyvalent Human Immuno. . . " J. Immunol. 142(10): 3612–3619, 1989.
Gallaher, 1987, "Detection of a Fusion . . . " Cell, 50: 327–328.
Fox, "No Winners Against AIDS" Biotechnology 12:128, 1994.
Cohen, "Jitters Jeopardize AIDS Vaccine . . . " Science 262: 980–981, 1993.
Butini, et al, "Comparative Analysis . . . " J. Cell Biochem. Suppl. 18B, J306, 1994.

*Primary Examiner*—Lynette R. F. Smith
*Assistant Examiner*—Brett Nelson
*Attorney, Agent, or Firm*—Nixon & Vanderhye P.C.

[57] ABSTRACT

The present invention relates to immunogenic preparations of peptides comprising amino acid sequences corresponding to antigenic determinants of the envelope glycoprotein of HIV, covalently coupled, directly or through a spacer molecule, to carrier molecules suitable for vaccination of mammals.

2 Claims, 35 Drawing Sheets

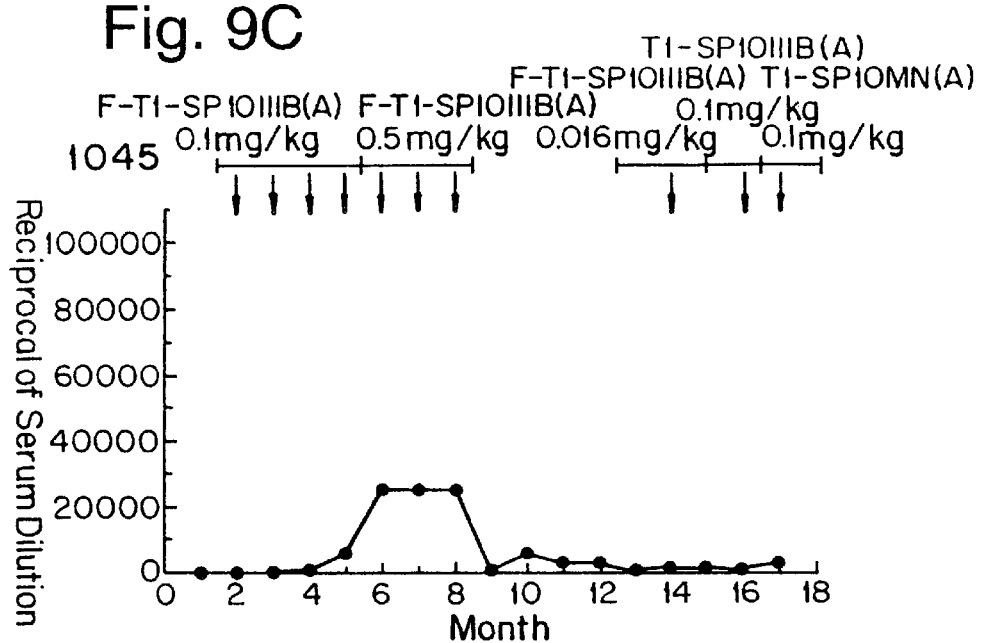
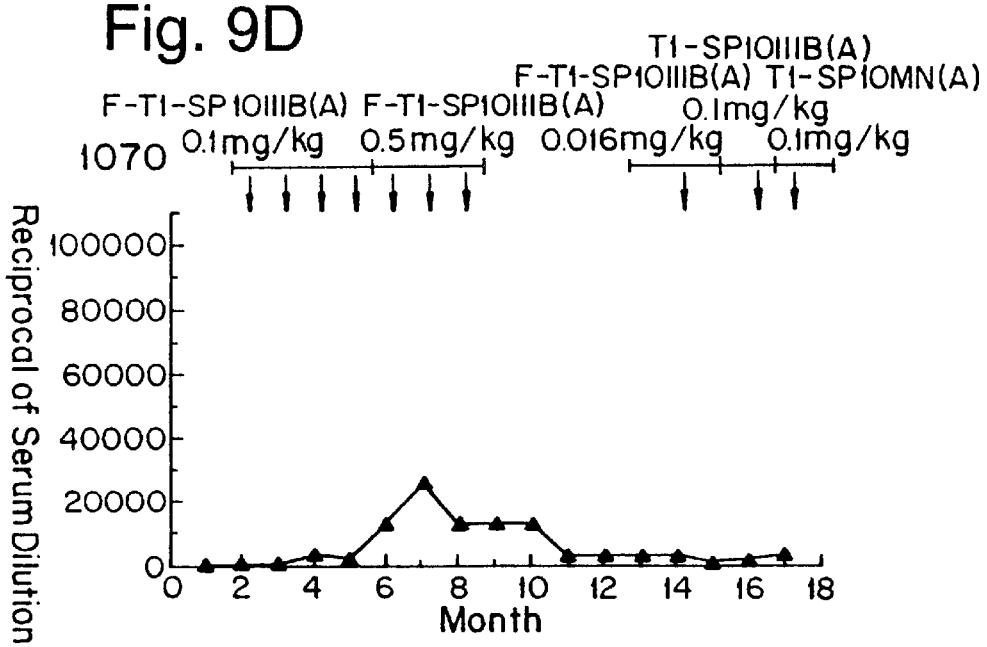

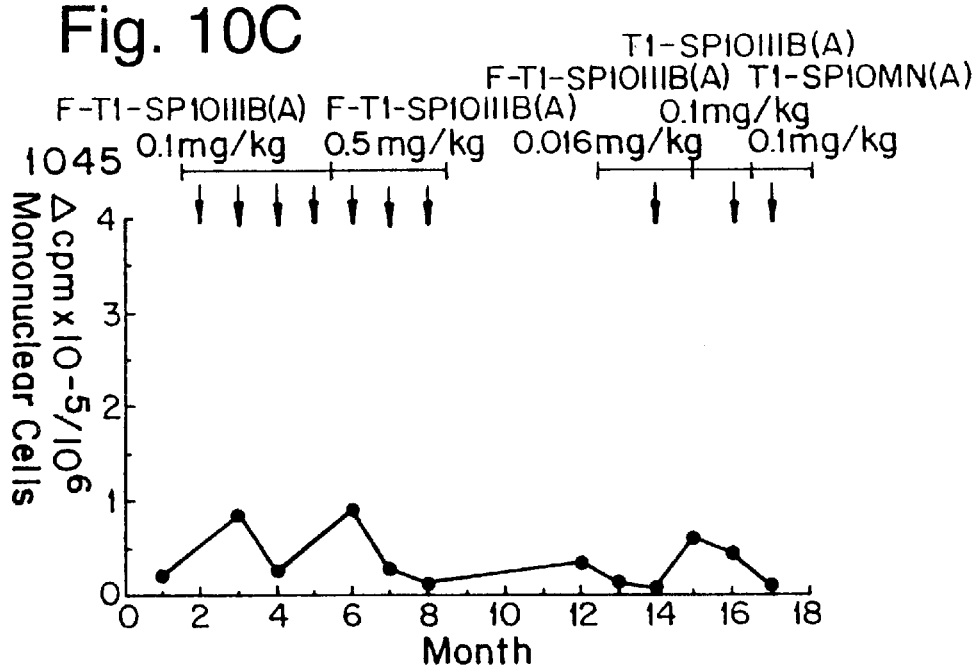
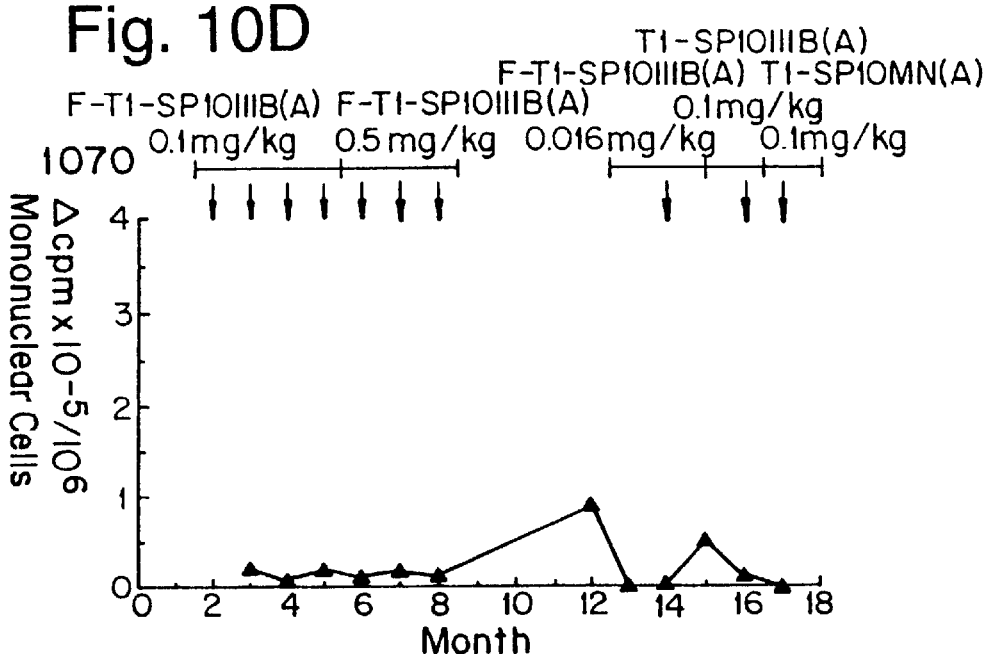

ANTIBODY TO IMMUNIZING PEPTIDE IN RHESUS MONKEYS IMMUNIZED WITH T1-SP10MN(A) PEPTIDE

Fig. 15

NEUTRALIZING ANTIBODY LEVELS IN SYNCYTIUM
INHIBITION ASSAY IN SERUM OF RHESUS MONKEYS
IMMUNIZED WITH F-T1-SP10MN(A) PEPTIDE

SERUM ANTIBODY TITERS TO IMMUNIZING PEPTIDE IN RHESUS MONKEYS IMMUNIZED WITH F-T1-SP10MN(A) PEPTIDE

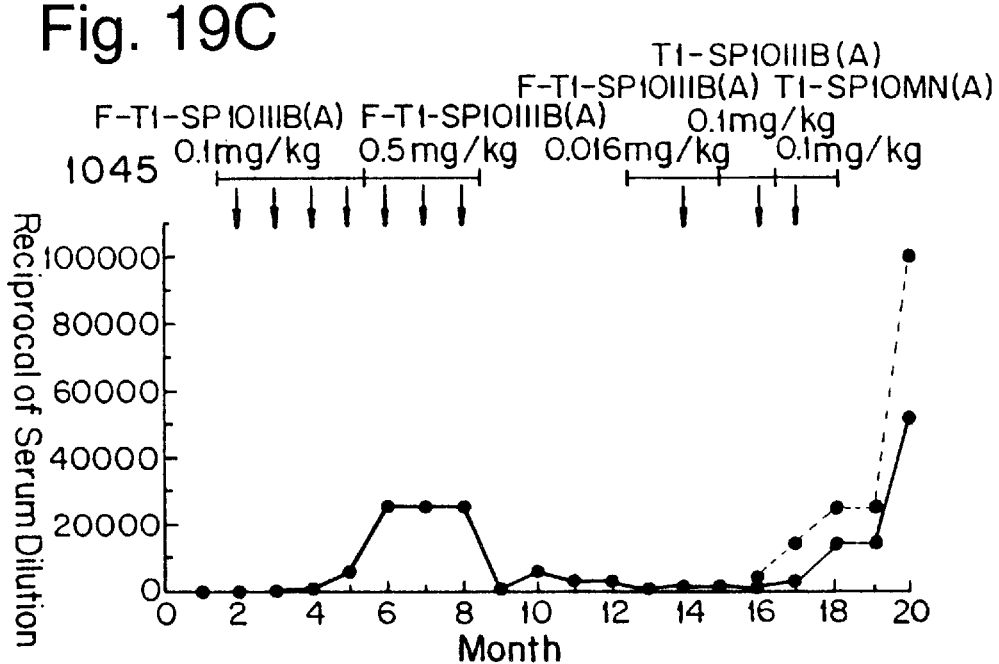
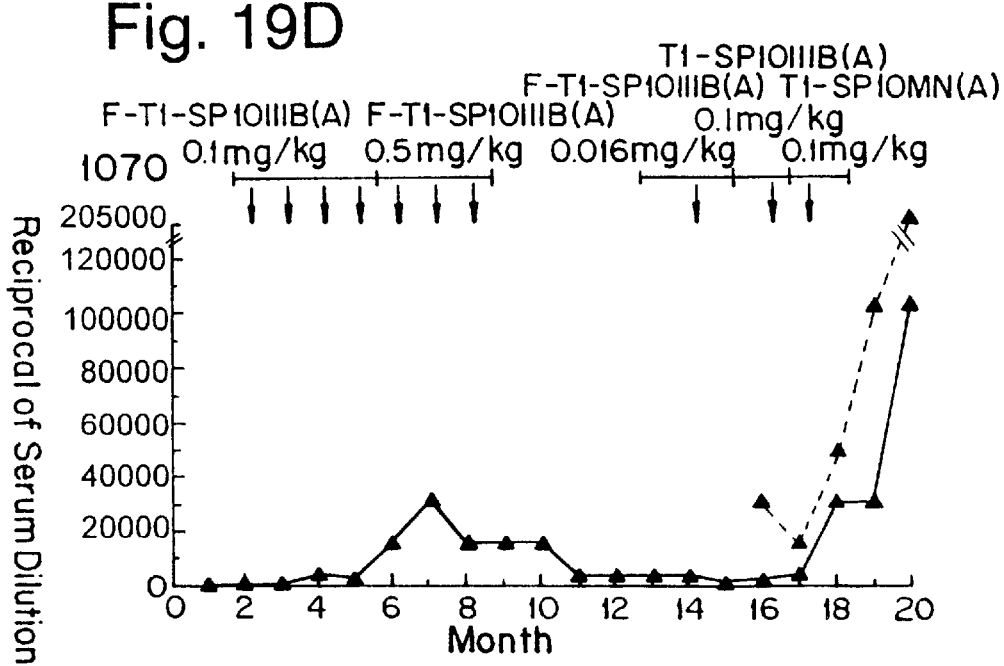

Fig. 27 Sequence of T1-SP10(A) Th-B-Tc Peptides For Human Immunization

| T1 | SP10 | A | |
|---|---|---|---|
| KQIINMWQEVGKAMYA | TRPNYNKRKRIHIGPGRA | FYTK | T1-SP10MN(A) |
| KQIINMWQEVGKAMYA | TRPNNNTRKSITKGPGRV | IYATG | T1-SP10RF(A) |
| KQIINMWQEVGKAMYA | TRPGNNTRKSIPIGPGRA | FIATS | T1-SP10EV91(A) |
| KQIINMWQEVGKAMYA | TRPHNNTRKSIHMGPGKA | FYTTG | T1-SP10Can0A(A) |

SYNTHETIC VACCINE FOR PROTECTION AGAINST HUMAN IMMUNODEFICIENCY VIRUS INFECTION

This is a continuation-in-part of application Ser. No. 08/235,305, filed Apr. 29, 1994 now abandoned, which is a continuation-in-part of application Ser. No. 07/858,361, filed Mar. 27, 1992 now abandoned, which is a continuation-in-part of application Ser. No. 07/832,849, filed Feb. 10, 1992 now abandoned, which is a continuation-in-part of application Ser. No. 07/591,109, filed Oct. 1, 1990 now abandoned, which is a continuation-in-part of application Ser. No. 07/093,854, filed Sep. 8, 1987 now U.S. Pat. No. 5,019,387, the entire contents of which are hereby incorporated by reference.

This invention was made with Government support under Grant No. CA-43447 awarded by the National Institutes of Health. The Government has certain rights in the invention.

BACKGROUND OF THE INVENTION

1. Technical Field

The present invention relates, in general, to immunogenic preparations and, in particular, to peptides comprising amino acid sequences corresponding to a region of the human immunodeficiency virus (HIV) envelope protein, against which neutralizing antibodies are produced. The invention further relates to a vaccine comprising the peptide coupled, either directly or through a spacer molecule, to a carrier molecule, suitable for vaccination of humans.

2. Background Information

The human retrovirus HIV has been demonstrated to be the causative agent of acquired immunodeficiency syndrome (AIDS), a disease for which there is currently no cure. The epidemiologic pattern among AIDS-related cases indicates that it is a transmissible disease. The virus is frequently found in saliva, semen, whole blood and plasma from individuals in high risk categories, including male homosexuals, intravenous drug users, patients receiving blood products, and individuals from Haiti and Central Africa. The rapid rise in seropositivity among individuals in high risk categories, the virulence of the disease, and its growing world-wide distribution, underscore an overwhelming and immediate need for a vaccine capable of inducing complete protective immunity in non-infected individuals. The need for diagnostic reagents to be used in testing for the presence of antibodies against HIV in biological samples is also clear.

Previous work has demonstrated that HIV infects T lymphocytes of the immune system by attaching its external envelope glycoprotein (gp120) to the CD4 (T4) molecule on the surface of T lymphocytes, thus using the CD4 (T4) molecule as a receptor to enter and infect T cells. After infecting the cell, the virus subverts the ability of the T cell to fend off the virus.

Retroviral envelope glycoproteins have been shown to be important in evoking a virus-neutralizing antibody response, as determined by the ability of sera containing anti-envelope antibodies to inhibit HIV infection in vitro. Specifically, the HIV external envelope glycoprotein gp120 has been shown to be capable of inducing neutralizing antibodies in coats and in man (Robey et al., *Proc. Nat'l. Acad. Sci. (USA)* 83: 7023, 1986). Little is known of the precise location of epitopes on gp120 that are either immunogenic in HIV-infected patients or that give rise to neutralizing antibodies. However, the recombinant protein PB1 (Putney et al., *Science,* 234:1392, 1986), which encodes approximately one-third of the entire gp120 molecule, has been shown to include the part of the envelope protein that induces the formation of neutralizing antibodies.

The data accumulated to date suggest that neither PB1 nor intact gp120 are appropriate for use in a vaccine against HIV infection. Studies involving the use of goats and chimpanzees demonstrate that neither molecule has the ability to induce the production of high titers of neutralizing antibodies. In addition, it has been shown that the intact gp120 molecule binds to the T4 molecule of normal T cells and is capable of disrupting normal immune function. Specifically, whole gp120 envelope molecules interfere with normal CD4 (T4) function and suppress T cell activation in vitro (Mann et al., *J. Immunol.* 138:2640, 1987). Thus, the administration of vaccines comprising large pieces of the external envelope glycoprotein may actually be detrimental to the normal immune system.

It has become clear that HIV sequence diversity in the principle neutralizing domain of gp120 (the V3 gp120 envelope loop region) and rapid V3 loop sequence mutation rate is a major obstacle to overcome for vaccine development (Myers et al., *Human Retroviruses and AIDS* 1991; La Rosa et al., *Science,* 249:932–935, 1990; and Holley et al., *PNAS (USA),* 88:6800–6804, 1991). Nonetheless, studies continue to show the critical role that the gp120 V3 region plays in generating anti-HIV neutralizing antibodies (Jiang et al., *J. Exp. Med.* 174:1557–1593, 1990). Moreover, it has recently been shown that approximately 50% of current HIV isolates share a consensus of V3 sequences that is similar to the HIV MN isolate, and that approximately 80% of HIV isolates in the US share one of the 4 most common HIV sequences (Myers et al., *Human Retroviruses and AIDS* 1991; La Rosa et al., *Science,* 249:932–935, 1990; and Holley et al., *PNAS (USA),* 88:6800–6804, 1991). Further, two of these sequences, GPGRAF and IHIGPGRA, have induced widely cross-reactive HIV neutralizing antibodies in animals (Jahaverian et al., *Science,* 250:1590–1593, 1990 and Haynes et al., *AIDS Res. Humans. Retroviral,* 6:38–39, 1990).

Thus, critical to the development of a vaccine against HIV, is the generation of an antibody response against gp120 that will interfere with gp120 interaction with the CD4 (T4) molecule, but will not interfere with normal CD4 (T4) interaction with class II major histocapatibility molecules, a major normal function of the CD4 (T4) molecule in the mediation of a myriad of stages of normal T cell response. In addition, an effective vaccine against HIV will induce protective immune responses in primates and in man, that is, will prevent subsequent HIV infection from occurring.

An immunogen that induced salutory (protective) anti-HIV immune responses for about 80% of HIV strains would be of great clinical use in at least three settings. First, the successful immunization of HIV negative IV drug users, prison inmates and homosexual populations thought to be at high risk for contracting HIV infection would significantly blunt the progression of the AIDS epidemic. Second, if immunization of HIV-infected mothers during the first trimester of pregnancy could boost salutory anti-HIV virus responses and decrease transmission of HIV by 80%, then maternal-fetal HIV transmission would decrease form 30% to 6% of children born to HIV-infected mothers. Third, an immunogen against HIV that induced salutory and not pathogenic anti-HIV responses, would be useful for immunization of HIV-infected assymptomatic individuals to boost anti-HIV immune responses, and promote the maintenance of the assymptomatic HIV-infected state.

OBJECTS OF THE INVENTION

It is an object of the present invention to provide a peptide that, when linked to a carrier molecule and/or polymerized to form molecular aggregates, is capable of inducing the production in mammals of high titers of neutralizing antibodies against HIV, which peptide does not distrub normal immune function.

It is another object of the invention to provide a synthetic vaccine comprising a peptide having an amino acid sequence corresponding to an antigenic determinant of the HIV envelope protein that is capable of inducing protective immunity in mammals against HIV.

It is a further object of the invention to provide a vaccine capable of inducing protective immunity in mammals against various forms of HIV.

It is an additional object of the invention to provide a method of detecting the presence of anti-gp120 antibodies in biological test samples.

SUMMARY OF THE INVENTION

The invention relates to immunogenic preparations and vaccines made therefrom. Peptides having amino acid sequences corresponding to antigenic determinants of the envelope protein of HIV are covalently coupled, either directly or through spacer molecules, to suitable carrier molecules. Synthetic vaccines comprising one or more such peptides are disclosed.

In one embodiment, the present invention comprises an essentially pure form of a peptide having an amino acid sequence corresponding to an antigenic determinant of the envelope glycoprotein of HIV, which peptide is capable, when covalently linked to a carrier molecule, of inducing in a mammal high titers of protective antibodies against HIV. The peptide can have, for example, the sequence CTRPNNNTRKSIRIQRGPG, corresponding to amino acids 303–321 of the envelope glycoprotein of the HTLV-III$_B$ isolate (Ratner et al., Nature 313:277, 1985), or any portion thereof.

In another embodiment, the present invention comprises an immunogenic conjugate capable of inducing in a mammal high titers of protective antibodies against HIV, said conjugate comprising: (i) a carrier molecule covalently attached to (ii) a peptide comprising an amino acid sequence corresponding to an antigenic determinant of the envelope glycoprotein of HIV.

In yet another embodiment, the present invention comprises a method of producing immunity to HIV comprising administering the above-described conjugate to a mammal.

In another embodiment, the present invention comprises a method of detecting the presence of anti-gp120 antibodies in biological test samples.

BRIEF DESCRIPTION OF THE DRAWINGS

FIGS. 3A and 3B. Reactivity to gp120 of antibodies from HIV+ patient purified over synthetic peptide affinity columns.

FIGS. 9A–9D show antibody titers in ELISA assay against immunizing peptide over time in chimpanzees immunized with HIV env synthetic peptides.

FIGS. 10A–10D show peripheral blood mononuclear cell proliferative responses to the T1-SP10IIIB(A) peptide in 7 day tritiated thymidine incorporation assays.

FIG. 15 shows neutralizing antibody levels in syncytium inhibition assay in serum of Rhesus monkeys immunized with F-T1-SP10MN(A) peptide.

FIGS. 19A–19D. For details, see legend to FIG. 9. Solid lines indicate antibody titer against T1-SP10IIIB peptide; dotted line indicates antibody response against T1-SP10MN (A) peptide.

FIG. 27. Sequence of T1-SP10(A) Th-B-Tc peptides for human immunization.

FIG. 28 shows that mab 48d bound to the T1-SP10CANO(A) peptide, and the 17b antibody did not. This plate was stripped with 8 molar urea (a treatment previously shown not to affect antibody binding to linear V3 determinants of peptides on the plate) and demonstrated that 8 molar urea treatment of the peptide denatured the peptide and preventive subsequent 48d binding to the peptide. These data strongly suggested that 48d antibody bound to a conformational determinant on the C4-V3 peptide T1-SP10CANO(A).

DETAILED DESCRIPTION OF THE INVENTION

Figure 1:
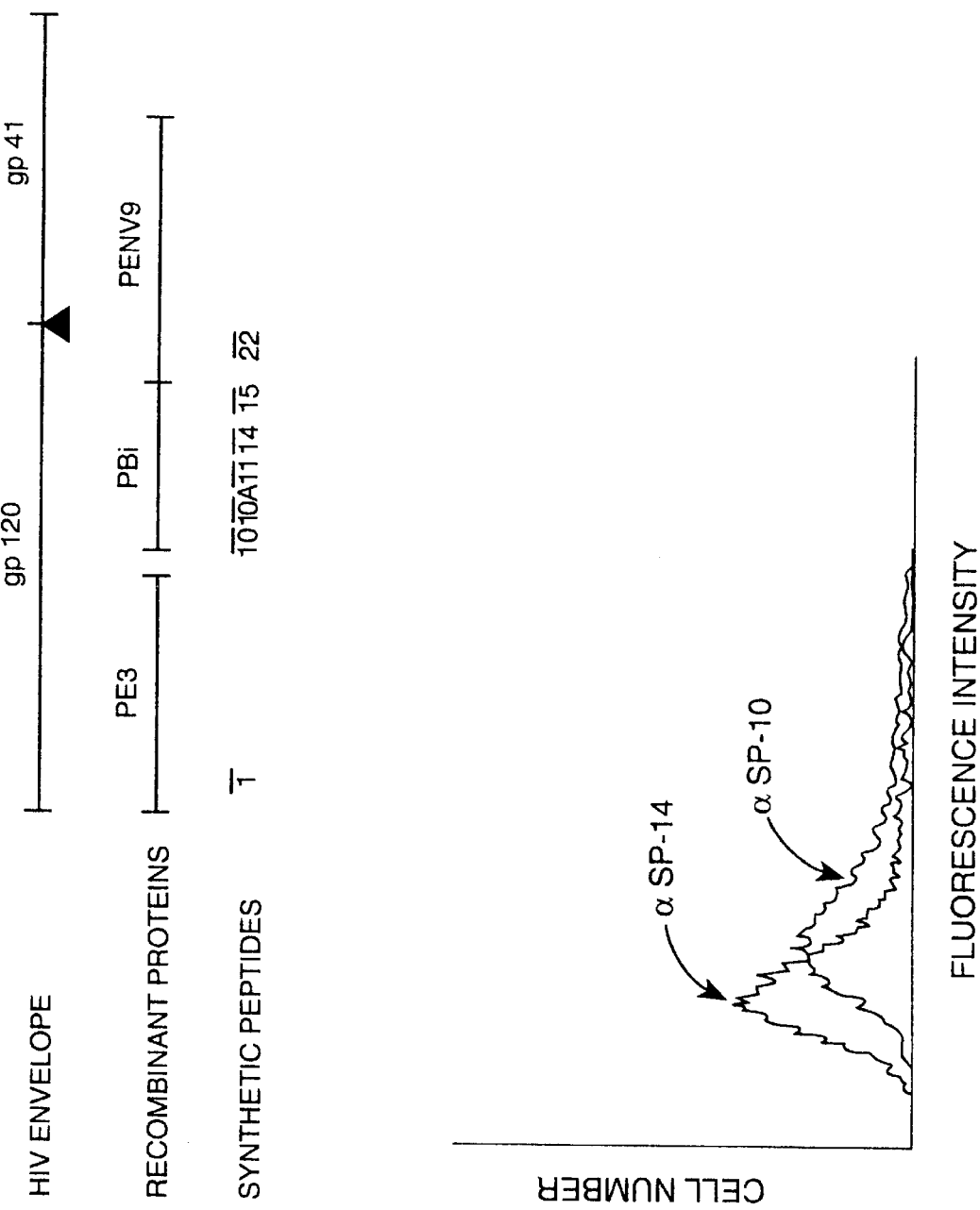
FIG. 1. Recombinant proteins and relation to synthetic peptides.

The present invention relates to peptides corresponding to immunogenic epitopes of HIV and synthetic vaccines made therefrom. These novel immunogenic agents are prepared by chemically synthesizing peptides sharing antigenic determinants with the envelope protein of HIV. The peptides are linked to carrier molecules (and/or are polymerized) rendering them suitable as vaccines. These vaccines are useful for immunization against AIDS when administered to mammals, for example, by the parenteral route.

It was determined that peptides that should be studied for immunogenic potential included those corresponding to hydrophilic, charged regions of the HIV envelope glycoprotein. It was further determined that, of such peptides, those with predicted beta turns would likely be of particular importance. It was recognized that the formation of intrapeptide disulfide bonds would be useful in establishing native configurational determinants. Also, it was recognized that formation of interchain disulfide bonds would be useful in polymerizing peptide molecules so as to form larger, more immunogenic peptide aggregates.

Computer analysis of the predicted amino acid sequence of the envelope protein of the HTLV-III$_B$ and ARV-2 isolates of HIV established the secondary structure and location of hydrophilic regions. Secondary structure was determined from the computer analysis using the method of Chou and Fasman (*Biochemistry* 13:211 and 13:222, 1974; *Advances in Enzymology* 47:45, 1978). Potential areas of beta turns were localized using the method of Rose (*Nature* 272:586, 1978). Hydrophilic regions of the envelope protein were identified by the technique of Rose and Roy (*Proc. Nat'l. Acad. Sci. USA* 77:4643, 1980).

The peptides of the instant invention correspond to, or are homologous with, B-cell epitopes present within the central region of the HIV isolate HTLV-III$_B$ envelope protein, or envelope protein of related HIV isolates. The peptides of the present invention are about 35 amino acids (units) or less in length, are hydrophilic, and when conjugated to appropriate carrier molecules, evoke the production in mammals of high titers (that is, advantageously, a reduction in infectivity of 100 infectious units of approximately 80% in vitro at 1:600 dilution of serum) of type (or isolate) specific neutralizing antibodies against HIV. Unlike the intact gp120 molecule, the peptides themselves are not capable of inhibiting interaction between the CD4 (T4) molecule on the surface of T lymphocytes and macrophage HLA class II molecules, and thus do not interfere with normal immune function. That is, peptides of the instant invention capable of inducing anti-HIV neutralizing antibodies, do not inhibit antigen-specific normal T cell proliferative responses in vitro.

Peptides of the instant invention can have, for example, the sequence CTRPNNNTRKSIRIQRGPG (designated SP-10), corresponding to amino acids 303–321 of the HTLV-III$_B$ envelope glycoprotein gp120 (Ratner et al., *Nature* 313:277, 1985), or some portion of that sequence. Peptides of the invention can also have sequences corresponding to the analogous SP-10 regions of HIV isolates other than HTLV-III$_B$, or portions thereof, these sequences being designated "SP-10-like" (see, for example, sequences in Table I).

TABLE I

| SP-10 and SP10-Like Sequences | |
|---|---|
| SP-10 III$_B$ | CTRPNNNTRKSIRIQRGPG |
| SP-10 MN | CTRPNYNKRKRIHIGPGRAF |
| SP-10 RF | CTRPNNNTRKSITKGPGRVIY |

TABLE I-continued

SP-10 and SP10-Like Sequences

| SP-10 SC | CTRPNNNTTRSIHIGPGRAFY |
|---|---|
| SP-10 WMJ-1 | CTRPNNNVRRRHIHIGPGRAFY |
| SP-10 WMJ-2 | CTRPYNNVRRSLSIGPGRAFR |
| SP-10 WMJ-3 | CTRPNDIARRRIHIGPGRAFY |
| SP-10 ARV-2 | CTRPNNNTRKSIYIGPGAFH |
| SP-10 LAV-1 | CTRPNNNTRKSIRRQRGPG |
| SP-10 HIV-2 (LAV-2) | CKRPGNKTVKQIMLMSGHVFHSHY |

The expression "SP-10-like" includes within its meaning the SP-10 sequence itself.

Carrier molecules to which peptides of the invention are covalently linked (conjugated) are advantageously, non-toxic, pharmaceutically acceptable and of a size sufficient to produce an immune response in mammals. Examples of suitable carrier molecules include tetanus toxoid, keyhole limpet hemocyanin (KLH), and peptides corresponding to T cell epitopes (that is, T1 and T2) of the gp120 envelope glycoprotein that can substitute for non-AIDS virus-derived carrier molecules (Cease, Proc. Nat'l. Acad. Sci. (USA) 84:4249, 1987; Kennedy et al., J. Biol. Chem. 262:5769, 1987). Peptides can also be administered with a pharmaceutically acceptable adjuvant, for example, alum, or conjugated to other carrier molecules more immunogenic than tetanus toxoid.

Linkage of a carrier molecule to a peptide of the invention can be direct or through a spacer molecule. Spacer molecules are, advantageously, non-toxic and reactive. Two glycine residues added to the amino terminal end of the peptide can provide a suitable spacer molecule for linking SP-10-like sequences, or portions thereof, to a carrier molecule; alternatively, SP-10-like sequences, or portions thereof, can for example be synthesized directly adjacent to, for example, another immunogenic HIV envelope sequence, for example, T1 or T2. Cysteines can be added either at the N or C terminus of the SP-10-like peptide for conjugation to the carrier molecule or to both ends to facilitate interchain polymerization via di-sulfide bond formation to form larger molecular aggregates.

Conjugation of the carrier molecule to the peptide is accomplished using a coupling agent. Advantageously, the heterofunctional coupling agent M-maleimidobenzoyl-N-hydroxysuccinimide ester (MBS) or the water soluble compound m-maleimidobenzoylsulfosuccinimide ester (sulfo-MBS) is used, as described by Green et al (Cell, 28:477; 1982) and by Palker et al. (Proc. Nat'l Acad. Sci. (U.S.A.) 84:2479, 1987).

Vaccines of the instant invention comprise one or more SP-10-like peptides, or portion thereof, each SP-10-like peptide being derived from a different HIV strain, which peptides are conjugated to carrier molecules. A polyvalent vaccine comprising a mixture of synthetic peptides, advantageously about 2 to about 10, corresponding in sequence to, for example, the isolates indicated in Tables I, can be used to provide immunity in man against various forms of HIV.

Advantageously, the SP-10 sequence of HTLV-III$_B$ (see Table I) can be conjugated to or synthesized with either the HTLV-III$_B$ gp120 envelope T cell epitope T1 (amino acids 428–443 of gp120), KQIINMWQEVGKAMYA, or to the T2 epitope (amino acids 112–124 of HTLV-III$_B$ gp120), HEDIISLWNQSLK (Cease et al., Proc. Nat'l. Acad. Sci (USA) 84:4249, 1987) to form a single polypeptide (in the case of T1-SP-10 from the HTLV-III$_B$ isolate of HIV, KQIINMWQEVGKAMYACTRPNNNTRKSIRIQRGPG). Similarly, T1 or T2 sequences from other HIV isolates can be linked to synthetic peptides derived from the SP-10 region of the corresponding isolates (see Table I), advantageously, at the N terminus of the SP-10-like peptide, to make a T1(or T2-)-SP-10-like peptide capable of inducing neutralizing antibody titers against a specific strain of HIV. Linkage at the C terminus of the SP-10-like peptide is also possible.

Smaller portions of SP-10-like peptides, for example, SP-10 RF(A) and SP-10 C (Table II) can also be covalently linked to carrier molecules, including gp120 T cell epitopes, and used in a vaccine.

The present invention also relates to an effective protective vaccine against strains of HIV comprising, in addition to SP-10-like sequences and appropriate carrier molecule(s) additional sequences from the gp120 envelope molecule. Since there is a major hypervariable region that is carboxy terminal to peptides designated as SP-10-like in Table I (envelope amino acids 322–333, Ratner et al, Nature 313:277, 1985), and since the hypervariable region may play a role in enhancing the ability of SP-10 -like peptides to raise type-specific neutralizing antibodies, amino acid sequences corresponding to a hypervariable region (approximately amino acids 322–333) of HIV isolates can be included as vaccine components, in part or in whole, as described for other SP-10-like peptides (see, for example, sequences in Table II). Hypervariable sequences are linked advantageously C-terminal to the SP-10-like peptide. Linkage N-terminal to the SP-10-like peptide is also possible.

TABLE II

SP-10 and SP-10-like sequences containing an additional carboxyterminal hypervariable domain and shortened SP-10-like sequences.

| SP-10 IIIB | CTRPNNNTRKSIRIQRGPGRAFVTIGKIGN |
|---|---|
| SP-10 MN | CTRPNYNKRKRIHIGPGRAFYTTKNIIGT |
| SP-10 RF | CTRPNNNTRKSITKGPGRVIYATGQIIGD |
| SF-10 SC | CTRPNNNTTRSIHIGPGRAFYATGDIIGD |
| SP-10 WMJ-1 | CTRPNNNVRRRHIHIGPGRAFYTGEIRGN |
| SP-10 WMJ-2 | CTRPYNNVRRSLSIGPGRAFRTREIIGI |
| SP-10 WMJ-3 | CTRPNDIARRRIHIGPGRAFYTGKIIGN |
| SP-10 ARV-2 | CTRPNNNTRKSIYIGPGRAFHTTGRIIGD |
| SP-10 LAV-Z | CTRPNNNTRKSIRIQRGPGRAFVTIGKIGN |
| SP-10 HIV-2 (LAV-2) | CKRPGNKTVKQIMLMSGHVFHSHYQPINKRPRQ |
| SP-10 C | CTRKSIRIQRGPGR(Y) |
| SP-10 RF(A) | CRKSITKGPGRVIY |

The present invention also relates to an effective protective vaccine against strains of HIV comprising, in addition to a SP-10-like sequence and a carrier molecule, a peptide corresponding to the HIV gp41 transmembrane region that is involved in viral-induced cell fusion, FLGFLG, (Gallagher, Cell 50:327, 1987). The FLGFLG sequence is added, advantageously, at the C terminus of the SP-10-like peptide. Addition at the N terminus of the SP-10-like peptide is also possible.

The present invention also relates to an effective vaccine against HIV formed from cysteine-T1-(or T2-)SP-10-like, cysteine-T1-(or T2-)SP-10-like-hypervariable region, or cysteine-T1-(or T2-) SP-10-like-FLGFLG polypeptides; and/or SP-10-like-cysteine or SP-10-like-hypervariable region-cysteine polypeptides. The polypeptides can be treated with oxidizing agents to induce disulfide bonds between polypeptide chain cysteines, to effect polymerized and therefore, highly immunogenic antigens. The molecular aggregates thus formed advantageously comprise SP-10-like peptides derived from (corresponding to) at least 2 HIV isolates.

A polyvalent HIV vaccine of the instant invention comprises, advantageously, two or more conjugates comprising an SP-10-like sequence, or portion thereof (see, for example, sequences in Table 1) derived from 2 or more HIV isolates, and a carrier molecule such as tetanus toxoid, or two or more T1- or T2-SP-10-like peptide conjugates, wherein both the T1 (or T2) and the SP-10-like sequences correspond to sequences present in a specific HIV isolate.

The advantage of using, as a carrier molecule, a synthetic peptide reflecting a portion of the gp120 molecule recognized by helper T cells, is that no other carrier molecule, such as tetanus toxoid, would be required, and the B and T cell response to HIV would be specific. Combining in a poylvalent vaccine several peptides reflecting sequences from the SP-10 region of different isolates, and possibly the T cell recognition region of the gp120 envelope, overcomes the problem of isolate-specific neutralization.

The present invention also relates to a polyvalent vaccine comprising SP-10-like peptides linked to hypervariable sequences described above (see, for example, Table II). A mixture of such polypeptides, coupled to appropriate carrier molecules and/or polymerized via disulfide bond formation (Harington, C. R., et al., *Biochem. J.,* 30:1598, 1930; Harington, C. R., et al., *Biochem. J.,* 38;417, 1944; Weygand et al., *Z. Naturforsch.,* 176:807, 1962), can be used as a vaccine to evoke a protective antibody response to multiple isolates of HIV.

SP-10-like peptides can be used in a solid phase radioimmunoassay (Palker et al. *J. Immunol* 136:2393, 1986; ibid., *Proc. Nat'l. Acad. Sci.* (*USA*) 84:2479, 1987) to (i) detect the presence and titers of neutralizing antibodies of HIV; and (ii) to determine with which strain of HIV the patient is infected. Thus, in addition to SP-10-like peptides being used as a vaccine or a component of a vaccine, the peptide can be used, as described above, for diagnostic purposes. Peptides of the instant invention can also be used in standard enzyme linked immunosorbent assays to detect the presence of HIV antibodies.

Summarizing and supplementing specific aspects of the foregoing, the present invention relates, at least in part, to a synthetic peptide comprising at least two regions of HIV proteins, the T1 gp120 env region, reported to be recognized by both B cells (Palker et al *J. Immunol.* 142:3612, 1989) and helper T cells (Cease et al *Proc. Natl. Acad. Sci.* (*USA*) 84:4249, 1987), and the SP10-like gp120 env region, a region that is also recognized by helper T cells and as well as by B cells and induces antibodies that are capable of neutralizing the human immunodeficiency virus (HIV) (see reference of Palker et al cited immediately above; Palker et al *Proc. Natl. Acad. Sci.* (*USA*) 85:1932, 1988; and also Rusche et al *Proc. Natl. Acad. Sci.* (*USA*) 85:3198–3202, 1988 and Goudsmit et al *Proc. Natl. Acad. Sci.* (*USA*) 85:4478, 1988) (see Tables III and IV).

TABLE III

VARIANTS OF THE T1-SP10 PEPTIDE DERIVED FROM HIV MN ENVELOPE SEQUENCES

| | F T1 SP10 A |
|---|---|
| T1-SP10 | KQIINMWQEVGKAMYACTRPNYNKRKRIHIGPGRA |
| T1-SP10(A) | KQIINMWQEVGKAMYACTRPNYNKRKRIHIGPGRAFYTTK |
| F-T1-SP10 | AVGIGALFLGFLKQIINMWQEVGKAMYACTRPNYNKRKRIHIGPGRA |
| F-T1-SP10(A) | AVGIGALFLGFLKQIINMWQEVGKAMYACTRPNYNKRKRIHIGPGRAFYTTK |

Sequences from Meyers et al. Human Retroviruses and AIDS, 1988, Los Alamos National Laboratory, Los Alamos, New Mexico, p. 11 68–92.

TABLE IV

VARIANTS OF THE T1-SP10 PEPTIDE DERIVED FROM HIV IIIB ENVELOPE SEQUENCES

| | F T1 SP10 A |
|---|---|
| T1-SP10 | KQIINMWQEVGKAHYACTRPNNNTRKSIRIQRGPG |
| T1-SP10(A) | KQIINMWQEVGKAMYACTRPNNNTRKSIRIQRGPGRAFVTI |
| F-T1-SP10 | AVGIGALFLGFLKQIINMWQEVGKAMYACTRPNNNTRKSIRIQRGPG |
| F-T1-SP10(A) | AVGIGALFLGFLKQIINMWQEVGXAMYACTRPNNNTRKSIRIQRGPGRAFVTI |

Sequences from Ratner et al. Nature, 313:277, 1985.

Neutralizing antibodies produced by TI-SP10-like peptides are type-specific, in that antibodies raised against the HIV HTLVIIIB (IIIB) isolate do not neutralize the HIV HTLVIIIMN (MN) or HTLVIIIRF (RF) HIV isolates (Palker et al. *J. Immunol.* 142:3612, 1989). Similarly, neutralizing antibodies raised against the T1-SP10-like peptides containing sequences from the MN or RF HIV isolate neutralize the homologous isolate but do not neutralize any of the other two HIV isolates. However, when goat anti-T1-SP10-like antisera were tested against 9 HIV field isolates in North Carolina, anti-TI-SP10IIIB serum was observed to neutralize 1 of 9 HIV isolates, anti-T1-SP10RF serum neutralized 3 of 9 HIV isolates, and anti-T1-SP10MN serum neutralized 6 of 9 HIV isolates (Haynes et al *AIDS Res. Retrol.* 6:38, 1990) (see Table V).

TABLE V

| ABILITY OF ANTI-TI-SP10 SERUM TO NEUTRALIZE NORTH CAROLINA FIELD ISOLATES OF HIV | |
|---|---|
| ANTI-T1-SP10IIIB | 1/9 (11%) |
| ANTI-T1-SP10RF | 3/9 (33%) |
| ANTI-T1-SP10MN | 6/9 (67%) |

La Rosa et al (*Science* 249:932, 1990) have shown that the HIV MN motif described by Haynes et al in *AIDS Res. Retrol.* (above) is one of the prodominant motifs of HIV isolates cultured from AIDS patients around the United States.

Palker et al (*J. Immunol.* 142:3612, 1989) were the first to report that the strategy of mixing peptides from various isolates could be a successful approach to the problem of raising antibodies against numerous strains of HIV with divergent amino acid sequences in the 303–337 region of the HIV envelope. Moreover, Palker et al reported that the T1-SP10-like peptide was advantageous over synthetic peptides coupled to carrier molecules such as KLH or tetanus toxoid. Whereas carrier coupled peptides only induced large amounts of antibody against the carrier in polyvalent mixtures of peptides, when the T1 sequence of HIVIIIB env (amino acids 429–443) was covalently linked N-terminal to the SP10 sequence (amino acids 303–321), this carrier-free immunogen induced high titers of neutralizing antibodies to all three HIV isolates whose sequences were present in the T1-SP10 peptides. Moreover, Hart et al (*J. Immunol.* 1990) have recently shown that the T1-SP10 peptide is non-toxic to immune cells in rhesus monkeys and is capable of inducing high-titered neutralizing antibodies and T helper cells in vivo in these primates. Thus, the T1-SP10-like synthetic peptide construct is a simple, non-toxic and highly efficacious molecule for inducing high titered anti-HIV neutralizing antibody responses and T-helper cell responses in goats and primates.

One of the major problems in developing a vaccine for AIDS has been the question of whether antibody responses alone can protect an individual against both cell-free HIV and HIV-infected cells, or whether cell mediated immune responses (antigen-specific cytotoxic T cells) are needed as well. Certainly, many other viral infections require both antibody and cellular anti-viral immune responses for the generation of protective immunity (Long et al *Immunol. Today* 10:45, 1989). In addition, local immunity at mucosal surfaces consisting of IgG and IgA antibody responses and mucosal surface-associated cytotoxic T cell activity may be required to protect against transmission of HIV via sexual contact or via exposure of mucosal surfaces with infected blood. Thus, a synthetic peptide immunogen would be desirable that induced cytotoxic T cell (CTL) responses to HIV in addition to inducing neutralizing antibody and T helper cell responses. In addition to the embodiments disclosed and summarized above, the present invention relates to such an immunogen.

The F region (for example, amino acids 519–530 of the BH10/IIIB HIV isolate and homologous regions of other HIV-1, HIV-2 and simian immunodeficiency virus (SIV) isolates) has sequence homology to the F1 (fusion) peptides of paramyxoviruses (Gallaher *Cell* 50:327, 1987). The F region has been postulated to form a hydrophobic helical structure capable of inserting into lipid bilayers of cell membranes and inducing cell fusion. Bosch et al (*Science* 244:694, 1989) have demonstrated that the F region in SIV (that is, the region homologous to the 519–530 env gp41 region of the BH10/IIIB HIV isolate) does indeed mediate cell fusion of SIV-infected cells.

It has been determined that F-derivatized peptides are internalized in immune cells in such a way as to induce the same type of cytotoxic T cell response that is necessary for control of many viral infections, namely, the generation of HLA-restricted CD8+ cytotoxic T cells. F-derivatized peptides interact with cells of the immune system such that when injected into a mammal, they induce anti-HIV memory T helper cell activity, anti-HIV neutralizing antibodies, and memory anti-HIV CD8+, HLA-Class I restricted cytotoxic T cell responses.

Accordingly, the present invention relates, in a preferred embodiment, to peptides of the general formulae:

F-Th-SP10(X)

Th-SP10(X)

Th-SP10 and

F (X)

wherein:

F sequences are from the putative fusogenic domain of HIV env gp41 (for example, amino acids 519–530 in HIV isolate BH10/IIIB or homologous regions in other HIV-1, HIV-2 or SIV isolates, or sequences functionally equivalent thereto);

Th sequences are either the T1 or T2 T helper epitopes or alternatively are any of the T helper cell epitopes listed in Table X (below) or amino acid sequences from other regions of HIV proteins not listed but that function as T helper epitopes;

SP10-like sequences are from Tables I or II (see also Table VIII below) or from any SP10-like sequence from HIV field isolates (see, for example, LaRosa et al *Science* 249:932, 1990); and (X) sequences are HIV protein sequences recognized by MHC Class I or Class II restricted cytotoxic T cells. Examples of (X) region sequences are given in Tables VIII and IX below.

Alternatively, F sequences can be, for example, C-terminal to Th-SP10(X) sequences. Moreover, Th, SP10 and (X) sequences can be arranged in any order in the peptide construct.

The synthetic peptide immunogen of this embodiment of the invention is capable of inducing anti-HIV neutralizing antibodies, anti-HIV helper T cells, and anti-HIV cytotoxic (killer) T cells. One skilled in the art will appreciate that this immunogen (which is a fusion protein) can either be synthesized chemically or by recombinant means known in the art.

The immunogen can have, for example, the structure: F-T1-SP10-(A). While examples of such immunogens are given in Tables III and IV, one skilled in the art will appreciate that any SP10-like sequence from field or laboratory HIV isolates (for example, LaRosa et al *Science* 249:932, 1990) can be substituted for the SP10 sequences shown in Tables III and IV (see also Tables I and II).

The T1-like sequences can be selected from T1-homologous sequences from any sequenced HIV isolate including those shown in Table VI.

TABLE VI

HIV Envelope gp120 T1 Sequences From Multiple HIV Isolates

| Isolate | Sequence |
|---|---|
| HIV-1 | |
| BH10/IIIB | K Q I I N M W Q E V G K A M Y A |
| BRU | - - F - - - - - - - - - - - - - |
| MN | - - - - - - - - - - - - - - - - |
| SC | - E I - - - - - - - - - - - - - |
| SF2 | - - I - - - - - - - - - - - - - |
| CDC4 | - - I - - R - - V - - - - - - - |
| WMJ2 | - - I - - - - - G - - - - - - - |
| RF | - - I V - - - - - - - - - - - - |
| ELI | - - I - - - V A G : R - - I - - |
| MAL | - - I - - - - - K T - - - - - - |
| Z6 | - - I - - - - - G - - - - - - - |
| Z3 | - - V V R T - - G - - Q - - - - |
| Z321 | - - I V - - - - R - - Q - - - - |
| JY1 | - - I - - - - - G - - - - - - - |
| HIV-2 | |
| ROD | K Q I I N T W H K V G R N V Y L |
| NIHZ | R - - - - - - - R - - K - L - - |

Sequences for BH10 are amino acids 428–443 from Ratner, L. et al, Nature 313:227–284, 1985.
Sequences for the remainder of the HIV-1 and HIV-2 isolates from Myers, et al, Human Retroviruses and AIDS, 1988, Los Alamos National Laboratory, Los Alamos, New Mexico, p. II-89.
: = no amino acid.

The F-like sequences can be selected from F-homologous sequences from any sequenced HIV isolate, including those shown in Table VII.

TABLE VII

HIV Envelope gp41 Fusion Protein (F) Sequences From Multiple HIV Isolates

| Isolate | Sequence |
|---|---|
| HIV-1 | |
| BH10 | A V G : I G A L F L G F L |
| MN | A A : : - - - - - - - - - |
| SC | - - - T - - - M - - - - - |
| SF2 | - - - I V - - M - - - - - |
| CDC4 | - - - M L - - M - - - - - |
| WMJ2 | - - - T - - - M - - - - - |
| RF | - - - T - - - M - - - - - |
| ELI | - I - : L - - M - - - - - |
| MAL | - I - : L - - M - - - - - |
| Z6 | - I - : L - - M - - - - - |
| Z321 | - I - M : - - F - - - - - |
| JY1 | - I - : L - - V - - - - - |
| WMJ1 | - - - A - - - M - - - - - |
| HIV-2 | |
| ROD | R G V F V L G F L G F L |
| NIHZ | - - - - - - - - - - - - |

Sequences for BH10 are amino acids 519–530 from Ratner, L. et al Nature 313:277–284, 1985.
Sequences for the remainder of the HIV-1 and HIV-2 isolates from Myers, et al, Human Retroviruses and AIDS, 1988, Los Alamos National Laboratory, Los Alamos, New Mexico, p. II-90. WMJ1 sequence is from Brasseur et al. AIDS Res. Retrovirol. 4:83–90, 1988.
: = no amino acid.

The (A) region-like sequences can be selected from (A)-homologous sequences from any HIV isolate, including those shown in Tables II and VIII.

TABLE VIII

SP 10 AND SP10-LIKE and (A) REGION gp120 SEQUENCES FROM MULTIPLE HIV ISOLATES

| Isolate | SP10 Region | (A) Region |
|---|---|---|
| HIV-1 | | |
| BH10(IIIB) | C T R P N N N T R K S I R I Q R G P G | R A F V T I G K I G |
| MN | C T R P N Y N K R K R I H I G P G R A | F Y T T K N I I G T |
| RF | C T R P N N N T R K S I T K G P G R V I Y | A T G Q I I G D |

TABLE VIII-continued

SP 10 AND SP10-LIKE and (A) REGION gp120 SEQUENCES
FROM MULTIPLE HIV ISOLATES

| Isolate | SP10 Region | (A) Region |
|---------|-------------|------------|
| SC | C T R P N N N T T R S I H Z G P G R A F Y | A T G D I I G D |
| WMJ-1 | C T R P N N N V R R R H I H I G P G R A F Y | T G E I R G N |
| WMJ-2 | C T R P Y N N V R R S L S I G P G R A F R | T R E I I G I |
| WMJ-3 | C T R P N D I A R R R I H I G P G R A F Y | T G K I I G N |
| ARV-2 | C T R P N N N T R K S I Y I G P G R A F H | T T G R I I G D |
| LAV-1 | C T R P N N N T R K S I R I Q R G P G | R A F V T I G K I G |
| HIV-2 | | |
| LAV-2 | C K R P G N K T V K Q I M L M S G H V F H S H Y | Q P I N K R P R Q |

Sequences from BH10 (IIIB) are from Ratner et al Nature 313:270–284, 1985.

The invention further relates to a peptide comprising the F region sequence (that is, for example, amino acids 519–530 of the BH10/IIIB isolate or other homologous region in other HIV-1, HIV-2 or SIV isolates) from HIV gp41 placed (covalently linked) N terminal to SP10 or SP10-like regions from any HIV sequence (see, for example, Table II) from field isolates such that the resulting construct can induce neutralizing antibodies and cytotoxic T cells against HIV.

One skilled in the art will appreciate from a reading of the present disclosure that MHC Class I restricted cytotoxic T cells can be induced by administering in vivo, as an example, the 519–530 amino acid region of HIV gp41, consisting of the 12 amino acids: AVGIGALFLGFL (F) or F-region sequences of other HIV-1, HIV-2 or SIV isolates (see, for example, Table VII) that are homologous to the 519–530 amino acid sequence of isolate BH10/IIIB (Table VII), covalently linked to any other peptide ranging in length from, for example, 3 to 50 amino acids, such that the F-linked peptide will associate with antigen-presenting cells in such a way as to effect the processing and presentation of the synthetic peptide that is covalently linked to F so that the peptide is presented to T cells in the context of MHC Class I molecules and generates the development of CD8+ cytotoxic T cells in vivo. In the context of an efficacious AIDS vaccine, several F-derivatized hybrid HIV peptides can be constructed comprising the F amino acid sequence (see, for example, Table VII) coupled N or C terminal to an amino acid sequence of HIV proteins that are capable of inducing cytotoxic T cells in vivo. Examples of described HIV peptides that are capable of being recognized by HLA Class I cytotoxic T cells are shown in Table IX.

TABLE IX

CYTOTOXIC T CELL EPITOPES OF HIV PROTEINS

| AA | Peptide Name | HIV Protein | Sequence | (Restricting HLA) | Ref. |
|---|---|---|---|---|---|
| 315–329 | P18 | gp120 | RIQRGPGRAFVTIGK | | a |
| 350–360 | P21 | gp120 | KQIDSKLREQFGNNK | | |
| 410–429 | --- | gp120 | GSDTITLPCRIKQFINMWQE | (DR4) | b |
| 644–658 | P41 | gp41 | NYTSLIHSLIEESQN | | a |
| 664–678 | P42 | gp41 | EQELLELDKWASLWN | | a |
| 787–801 | P47 | gp41 | RIVELLGRRGWEALK | | a |
| 172–196 | 40 | pol(rt) | IETVPVKLKPGMDGPKVKQWPLTEE | (B8) | c |
| 325–349 | 49 | pol(rt) | AIFQSSMTKILEPFRKQNPDIVIYQ | (All) | c |
| 342–366 | 50 | pol(rt) | NPDIVIYQYMDDLYVGSDLEIGQHR | (All) | c |
| 359–383 | 51 | pol(rt) | DLEIGQHRTKIEELRQHLLRWGLTT | (Bw60) | c |
| 461–485 | 57 | pol(rt) | PLTEEAELELAENREILKEPVHGVY | (A2) | c |

TABLE IX-continued

CYTOTOXIC T CELL EPITOPES OF HIV PROTEINS

| AA | Peptide Name | HIV Protein | Sequence (Restricting HLA) | | Ref. |
|---|---|---|---|---|---|
| 495–519 | 59 | pol(rt) | EIQKQGQGQWTYQIYQEPFKNLKTG (All) | | c |
| 265–279 | --- | gag p24 | KRWIILGLNKIVRMY(C) | (B27) | d |

Sequence numbers for gp120 and gp41 are from Ratner et al Nature 313:277–284, 1985.
Sequence numbers for pol and gag proteins from Sciliciano et al (Cell 54:561, 1988) and Walker et al (Proc. Natl. Acad. Sci. (USA) 86:9514, 1989), respectively.
[a]Takahashi et al Proc. natl. Acad. Sci. (USA) 85:3105, 1988
[b]Sciliciano et al Cell 54:561, 1988
[c]Walker et al Proc. Natl. Acad. Sci. (USA) 86:9514, 1989
[d]Nixon et al Nature 336:484, 1988.

This latter strategy is important in that cytotoxic T cell epitopes are recognized by specific polymorphic HLA Class I or Class II molecules. If only 1 such epitope [represented by one linear sequence of a peptide, such as the (A) peptide] is present in the vaccine, then only those individuals with the specific HLA antigen that the (A) peptide uses to be presented to cytotoxic T cells would develop cytotoxic T cells against HIV. However, if numerous F-derivatized peptides, each containing a peptide that is capable of being recognized in the context of a distinct HLA Class I or Class II molecule by cytotoxic T cells, are contained in an immunogen, then individuals with a wide spectrum of HLA-types will make cytotoxic T cells against HIV.

Thus, an immunogen capable of inducing anti-HIV cytotoxic T cells in the majority of people in a population, advantageously contains a mixture of peptides, each recognized by a distinct HLA Class I type (for instance) such that together, the mixture includes peptides that are immunogenic and recognized by Class I types of molecules that, taken together, are expressed by the majority of individuals in a given population. Table IX shows examples of described cytotoxic T cell epitopes and their HLA restricting elements, if known, that are the types of peptides that can be derivatized by F-sequences and used as a mixture with F-T1-S10 (A) peptides. Alternatively, sequences in Table IX can be covalently linked C-terminal to SP10 sequences in F-T1-SP10 peptides instead of (X) sequences and a mixture of F-T1-SP10(X) peptides used as an AIDS vaccine (in the formulation F-T1-SP10(X), X is either an (A) sequence (see Tables II and VIII) or other cytotoxic T cell-inducing sequence such as are listed in Table IX).

The same considerations of MHC restriction that apply to T cytotoxic epitopes also apply to T helper epitopes. That is, recognition of antigens by T helper cells is HLA restricted and for the majority of members of a population cohort to respond to an immunogen and generate a T helper cell response to the immunogen, sufficient T helper cell epitopes will need to be present in order to have available sufficient varieties of T helper epitopes within which each patients' T cells may be able to see processed antigen in the context of their own HLA Class II molecules. Table X shows T helper cell epitopes of HIV proteins that can be substituted for the T1 or T2 sequences in the F-Th-SP10(X) construct to provide alternative T helper cell epitopes in the construct.

TABLE X

| T Cell Helper Epitopes in HIV Proteins | | | |
|---|---|---|---|
| Peptide Name | Amino Acid | Protein | % Responding |
| gp41-1 | 603–614 | gp41 | 41 |
| gp41-2 | 609–620 | gp41 | 42 |
| gp41-3 | 655–667 | gp41 | 38 |
| gp41-5 | 737–749 | gp41 | 21 |
| gp41-7 | 584–609 | gp41 | 24 |
| gp120-1 | 108–119 | gp120 | 31 |
| gp120-2 | 115–126 | gp120 | 38 |
| gp120-4 | 296–312 | gp120 | 14 |
| gp120-5 | 368–377 | gp120 | 21 |
| gp120-6 | 74–85 | gp120 | 7 |
| gp120-7 | 233–244 | gp120 | 7 |
| p24-1 | 466–473 | p24 | 14 |
| p24-2 | 439–446 | p24 | 14 |
| p24-3 | 228–235 | p24 | 14 |
| p24-4 | 22–29 | p24 | 14 |
| p24-11 | 282–301 | p24 | 24 |
| pol-1 | 899–913 | pol | 28 |
| pol-2 | 923–937 | pol | 38 |
| pol-3 | 942–954 | pol | 48 |
| pol-4 | 720–730 | pol | 35 |
| T1 | 428–443 | gp120 | 77 |
| T2 | 112–124 | gp120 | 54 |
| TH4 | 834–848 | gp41 | 75 |
| p18 | 315–329 | gp120 | 50 |
| gp41-1 + gp41-2 + gp41-3 | | | 80 |
| pol-1 + pol-2 + pol-3 | | | 80 |
| gp41-1 + gp41-3 + pol-1 + pol-2 | | | 93 |

Sequences from the first 20 peptides above are from Schrier et al (J. Immunol. 142:1166–1176, 1989) and sequences T1, T2, Th4 and p18 are from Clerici et al (Nature 339:383–385, 1989).

Studies indicate that the same T helper cell epitope may be recognized by T cells in the context of multiple HLA Class II specificities and, therefore, only a few T helper epitopes are needed to formulate an effective synthetic peptide based AIDS vaccine. Clerici et al (*Nature* 339:383–385, 1989) have provided data that T cells of 85% of the population studied could recognize either T2 or T1 T helper cell epitopes (see Table X). Schrier et al (*J. Immunol.* 142:1166–1176, 1989) have identified a number of helper T cell epitopes in HIV proteins and demonstrated that T cells of 93% of the population studied responded to at least 1 of 4 T helper cell epitopes (see Table X).

Thus, in a preferred embodiment, the AIDS vaccine of the present invention has the general structure and composition of mixtures of peptides of the formulation:

F-Th-SP10(X)

Th-SP10(X)

Th-SP10 and

F(X)

where, as indicated above, F sequences are from the putative fusogenic domain of HIV env gp41 (for example, amino acids 519–530 in HIV isolate BH10/IIIB or homologous regions in other HIV-1, HIV-2 or SIV isolates, or sequences functionally equivalent thereto) (see, for example, Table VII); Th sequences are either the T1 or T2 T helper epitopes or alternatively are any of the T helper cell epitopes listed in Table X or amino acid sequences from other regions of HIV proteins not listed but that function as T helper epitopes, SP10-like sequences are from Tables I, II or VIII or from any SP10-like sequence from HIV field isolates (see, for example, LaRosa, G. et al. Science 249:932–935, 1990); and (X) sequences are HIV protein sequences recognized by MHC Class I or Class II restricted cytotoxic T cells. Examples of (X) region sequences are given in Tables VIII and IX.

The exact sequences to be included in the F-Th-SP10(X), Th-SP10(X), Th-SP10 and F(X) peptides and the number of different peptides comprising the AIDS vaccine of the invention is determined by the number of cytotoxic T cell (X) and Th epitopes needed to induce cytotoxic T cells and T helper cell responses in the majority of subjects in a given population cohort. One skilled in the art will appreciate that the order of F, Th, SP10 and (X) can vary as long as the above-indicated function of each is retained. For the induction of protective anti-HIV neutralizing antibodies, the specific SP10-like sequences necessary to be present in F-Th-SP10(X) peptides will depend upon the number of variations of HIV isolates in a given population at a given time. One skilled in the art will appreciate that this information will need to be actively and continuously monitored in the population and the formulation of the AIDS vaccine changed from time to time depending on changes in the above variables.

The induction of protective anti-HIV neutralizing antibodies in populations that include a number of different HIV isolates can be effected using the vaccine strategy described above and/or by employing at least one peptide construct that mimics a conserved conformational determinant of gp120 and thus is capable of inducing broadly cross-reactive anti-HIV antibodies. One such construct takes the form of a mimotope of a conformational determinant of the native HIV gp120 C4-V3 region and is exemplified by T1-SP10CANO(A) (see Table XXIII). While the primary V3 sequence of the CANO envelope is widely disparate from other HIV envelop V3 sequences (see again Table XXIII), the T1-SP10CANO(A) peptide induces cross-reactive anti-V3 antibodies against a variety of HIV V3 motifs (see Example 11). This induction of cross-reactivity is due to secondary and higher order structures of the V3 loop of the HIV CANO isolate that result in the T1-SP10CANO(A) C4-V3 hybrid mirroring a broadly neutralizing determinant of HIV gp120. This is demonstrated by the fact that the human anti-gp120 monoclonal antibody 48d (which blocks mouse monoclonal antibodies that prevent CD4 binding to gp120 but does not itself block gp120-CD4 binding (Thali et al, J. Virol. 67:3978–3988 (1993)) binds T1-SP10CANO(A).

As an alternative embodiment (strategy), an effective vaccine can be formulated by determining the HLA Class I and Class II types for a particular individual by, for example, either polymerase chain reaction analysis or by conventional HLA tissue typing analysis. Based on that information, the specific immunogens that need to be included in the F-Th-SP10(X), Th-SP10(X), Th-SP10 and F(X) formulation can be determined. Thus, in this latter embodiment, the peptides given to the subject are those necessary for eliciting the desired anti-HIV B and T cell responses.

From a reading of the foregoing, one skilled in the art will appreciate that this is a general strategy for development of a vaccine for any infectious disease. Moreover, the ability to conjugate the F-region from the HIV g41 envelope protein to any sequence capable of being recognized by cytotoxic T cells (thereby creating a linear peptide suitable for injection and capable of being recognized by cytotoxic T cells in the context of MHC Class I molecules) provides a simple and effective method of inducing MHC Class I restricted cytotoxic T cells to any peptide bearing cytotoxic T cell epitope. This is the case regardless of whether the sequence of the cytotoxic T cell epitope is derived from proteins in an invading organism or whether the cytotoxic T cell epitope sequences are derived from host proteins.

As an example of the use of F-derivatized peptides that include sequences from host proteins, it is contemplated that F-derivatized peptides can be used comprising HIV gp41 F sequences (for example, amino acids 519–530 from the BH10/IIIB HIV-1 isolate or from homologous regions of other HIV-1, HIV-2 or SIV isolates, or sequences functionally equivalent thereto) conjugated either N- or C-terminal to peptides capable of being recognized by cytotoxic T cells in the context of MHC Class I or Class II, the sequences for such peptides being derived from the variable region of T cell receptor for antigen (TCR) molecules expressed on the surface of autoreactive T cells that mediate host tissue destruction in various autoimmune diseases, infectious diseases and in the setting of organ transplantation.

Sun et al (*Nature* 332:843, 1988; *Eur. J. Immunol.* 18:1993, 1988) have reported the isolation of cytotoxic T cell clones that are specific for idiotypic determinants on encephalitogenic T cells and which adoptively transfer resistance to experimental autoimmune encephalomyelitis. The concept of immunization of subjects with autoimmune disease with immunogens that would induce an immune response against the autoimmune clone of T cells has recently been recognized as an important experimental approach (Reviewed on Cohen et al *Immunol. Today* 332, 1988; Howell et al *Science* 246:668, 1989; Wralth et al *Cell* 57:709, 1589). Thus, the present invention provides a simple and effective method for inducing MHC-restricted Class I or Class II cytotoxic T cells to peptides of host antigens and thus represents a major advance in the development of vaccines for autoimmune disease.

Using standard recombinant DNA techniques and existing probes and sequences for TCR molecule antigen binding regions, sequences can be obtained from unique regions of the TCR molecules (Barns et al *J. Exp. Med.* 169:27, 1989). F-derivatized peptides can be used to induce a cytotoxic T cell immune response targeted to the specific clones of T cells bearing TCRs responsible for antigen-specific T cell-mediated host tissue damage in the above disease categories. Once induced, such an F-peptide-induced anti-TCR-targeted cytotoxic T cell response can eliminate the autoreactive clone or T cells, thereby providing a novel, highly specific strategy for the control of T cell-mediated tissue destruction.

A second example of the use of F-derivatized host peptides is to similarly control antibody-mediated tissue damage that occurs in the context of autoimmune diseases, infectious diseases, and in the setting of organ transplantation. B cell surface receptors for antigen (surface immunoglobulin) also contain regions that are specific for clones of B cells making antibodies. By identifying clones of B cells producing antibodies responsible for tissue-specific damage in the setting of the above disease categories, the sequence of peptides from the region of the B cell immunoglobulin molecule that binds antigen can be identified using, for example, recombinant DNA techniques. Further, sequences capable of inducing MHC Class I or Class II cytotoxic T cell responses can be identified. By derivatizing such an immunoglobulin antigen-binding region peptide with F sequences and injecting the F-derivatized peptide into the subject making the autoantibody, a cytotoxic T cell response against an autoantibody-producing B cell can be induced, thereby eliminating a tissue damaging autoantibody response that occurs in the context of the above disease categories.

A third example of the use of F-derivatized non-HIV proteins is the use of the principles described above for specific elimination of autoreactive T and B cell types for the treatment of clonal B and T cell malignancies that express on their surface clonal immunoglobulin or TCR molecules. Anti-tumor therapeutic strategies have been described that employ antibodies against variable regions of either B cell surface immunoglobulin molecules (Hamblin et al *Brit. J. Cancer* 42:495, 1980; Miller et al *N. Eng. J. Med.* 306:517, 1982) or antibodies against variable TCR regions in the case of treatment of T cell tumors (Kanagawa, O. *J. Exp. Med.* 170:1513–1519, 1989). Thus, F-derivatized synthetic peptides containing the sequences of variable regions of the TCR or immunoglobulin molecules expressed on the surface of T or B cell malignant cells respectively, can be injected into the tumor-bearing host to induce anti-TCR or anti-immunoglobulin-specific cytotoxic T cell responses that kill the tumor cells.

A fourth example of the use of F-derivatized non-HIV proteins is the creation of an immunogen that kills pathogen-infected cells and thus facilitates the elimination of pathogen-infected cells from the host. For example, Hepatitis C (non-A, non-B hepatitis) is a disease that is caused by the transfer of viral particles in cells or in serum from one individual to another. By F-derivatizing cytotoxic T cell epitope sequences of the Hepatitis C virus protein and injecting such sequences into individuals, memory anti-Hepatitis C specific cytotoxic T cell responses can be induced that protect the individual from infection with live Hepatitis C virus, thus providing a novel Hepatitis C vaccine, Such a strategy can also be used to create a vaccine for other infectious pathogens.

The following nonlimiting examples illustrate the invention in more detail.

EXAMPLE 1

Synthesis of Peptides and Preparation of Conjugates

Synthetic essentially pure peptides containing hydrophilic amino acid sequences from the HTLV-$III_B$ envelope glycoprotein gp120 (Ratner, et al. *Nature,* 313:277, 1985) were synthesized on an Applied Biosystems 430A peptide synthesizer using chemical and program cycles supplied by the manufacturer. Sequences of synthetic peptides are given in Table XI.

TABLE XI

SYNTHETIC PEPTIDES WITH HYDROPHILIC AMINO ACID SEQUENCES OF HTLV-$III_B$ ENVELOPE PROTEIN

| Synthetic Peptide | Amino Acid Number[a] | Sequence[b] |
|---|---|---|
| SP-1 | 80–91 | ACVPTDPNPQEV(Y) |
| 10 | 303–321 | CTRPNNNTRKSIRIQRGPG(Y) |
| 10A | 328–344 | (Y)GKIGNHRQAHCHISRAK |
| 11 | 341–363 | (Y)SRAKWNNTLKQIDSKLREQFGNN(C) |
| 14 | 393–421 | (Y)NSTQLFNSTWFNSTWSTKGSNNTEGSDTI(C) |
| 15 | 461–475 | (Y)LTRDGGNSNNESEIF(C) |
| 22 | 504–518 | APTKAXRRVVQREKR(C) |

[a]According to Ratner et. al., Nature, 313:277, 1985.
[b]Amino acids in parentheses were added for iodination of peptide (Y) and coupling to carrier protein (C).

The relationship of the peptides synthesized to known recombinant proteins PE3, PBI and PENV9 is shown in FIG. 1 (Putney et al., *Science,* 234:1392, 1986; Petteway et al., *Viruses and Human Cancer: UCLA Symposia on Molecular and Cellular Biology* 1987).

Peptides were conjugated to carrier molecules such as bovine serum albumin (BSA) or tetanus toxoid (TT) with MBS, as described by Green et al. (*Cell,* 28:477, 1982; Palker et al, *Proc. Natl. Acad. Sci.* (*USA*) 84:2479, 1987). For the coupling procedure, 24 mg of tetanus toxoid (for example) in 0.5 ml of phosphate buffered saline, pH 7.2, was incubated with 1 mg of MBS dissolved in 100 $\mu$l of dimethylformamide for 1 hr. at 23° C. Tetanus toxoid treated with MBS (TT-MBS) was then subjected to sieving chromatography on a PD-10 (Pharmacia) column to remove unreacted MBS from TT-MBS and fractions containing TT-MBS were recovered in the void volume of the column as determined by spectrophotometric assay at an optical density of 280 nm. TT-MBS was then incubated with rocking at 23° C. for 3 hr. with 6–9 mg of synthetic peptide (molar ratio 30:1, peptide carrier protein) in PBS containing reduced cysteine at either the carboxyl or amino terminus. TT-peptide conjugates were dialyzed overnight at 4° C. against PBS or again desalted on a PD-10 column and were used as an immunogen.

Conjugation of peptides to BSA or tetanus toxoid was monitored by subjecting conjugates to sodium dodecylsulfate-polyacrylamide gel electrophoresis (SDS- PAGE) under non-reducing conditions and by measuring the increase in apparent molecular weights over that of BSA and TT treated with MBS. Coupling efficiencies also monitored by trace iodination of peptides varied from 10–30% depending on the peptide.

EXAMPLE 2

Reactivity of AIDS Patient Antibodies to Synthetic Peptides

Figure 2:
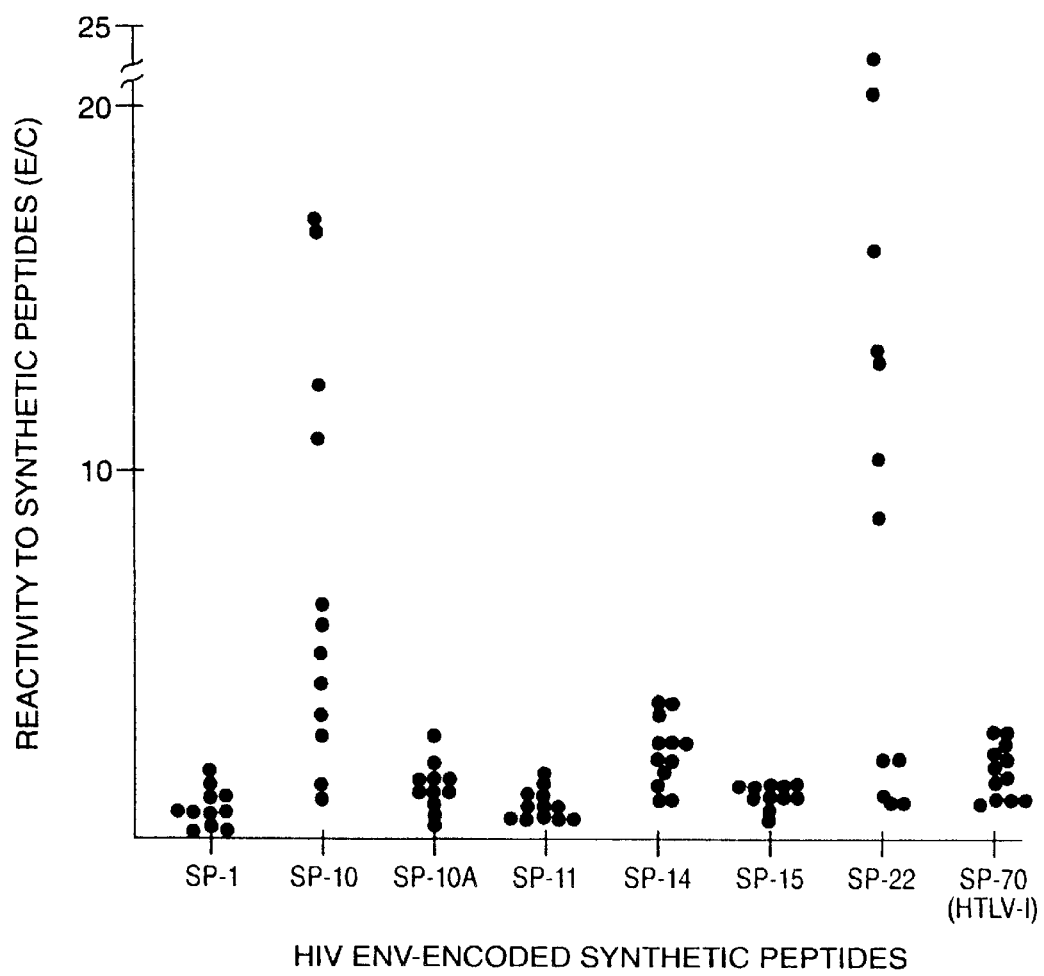
FIG. 2. Reactivity of AIDS patient antibodies to synthetic peptides.

Synthetic peptides derived from hydrophilic regions of gp120 coupled to BSA were used as antigens in a radioimmunoassay (RIA) with HIV+ patient sera (N=12) and normal serum control (N=4), to evaluate the AIDS patient antibody response to epitopes on gp120 (FIG. 2) (Palker et al., *J. Immunol.* 136:2393, 1986; ibid, *Proc. Nat'l. Acad. Sci (USA)*, 84:2479, 1987). The majority of HIV+ patient sera reacted with two synthetic peptides, SP-10 (9/12, 75%) and SP-22 (8/12, 67%).

Results are expressed as a ratio (E/C) of duplicate cpm values obtained with experimental (E) AIDS sera and control (C) serum samples. E/C>3.0=positive.

EXAMPLE 3

Figure 3A:
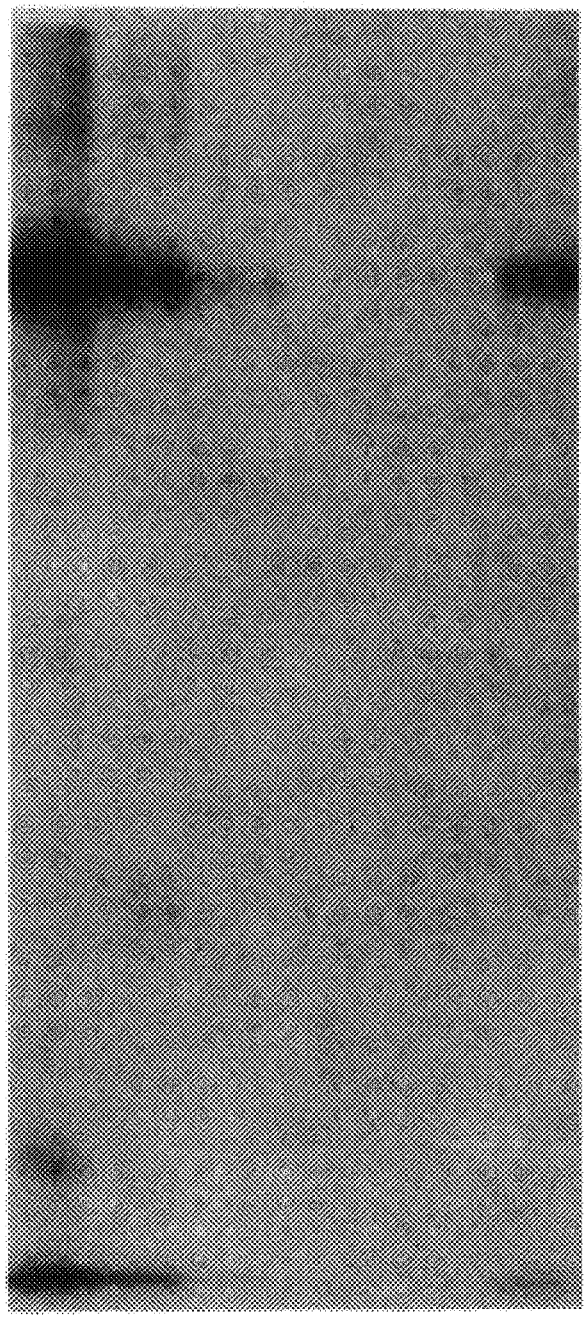

Reactivity of gp120 to Antibodies from HIV+ Patient Purified Over Synthetic Peptide Affinity Columns For preparation of affinity columns, synthetic peptides containing amino acid sequences from HTLV-III$_B$ gp120 (SP-10, 10A, 11, 14, 15, 22, see FIG. 1) were coupled to BSA and then covalently linked to CNBr-activated Sepharose. Serum aliquots (2 ml) from an HIV seropositive patient were then passed over each column and the antibodies that bound to the affinity columns were then tested for reactivity to purified $^{125}$I-labelled HTLV-III$_B$ gp120 in RIP assay (FIG. 3A) and for reactivity to the surface of H-9 cells infected with HTLV-III$_B$ in indirect immunofluorescence assays (FIG. 3B).

A) In RIP assay (Palker et al., *Proc. Nat'l. Acad. Sci (USA)* 84:2479, 1987; ibid, *J. Immunol.* 136:2393, 1986), bound antibodies from the SP-10 (lane 1), SP-10A (lane 2), SP-11 (lane 3), and SP-22 (lane 6) affinity columns reacted with gp120-III$_B$ in RIP assay, with antibodies from the SP-10 column showing the greatest reactivity to gp120-III$_B$.

B) When tested in FACS analysis (Shapiro, *Practiced Flow Cytometry*, Alan R. Liss Pub., N.Y., N.Y., 1985), antibodies reactive with synthetic peptide SP-10 bound to the surface of HIV-infected cells while binding of affinity purified antibodies to SP-14 or to SP-10A, 11, 15 or 22 (not shown) was not detected. These data suggest that the antigenic site(s) defined by SP-10 are accessible to antibody binding when gp120 is present on the surface of HIV+ cells.

EXAMPLE 4

Neutralization of HIV by Goat Anti-SP-10 Antisera

Figure 4:
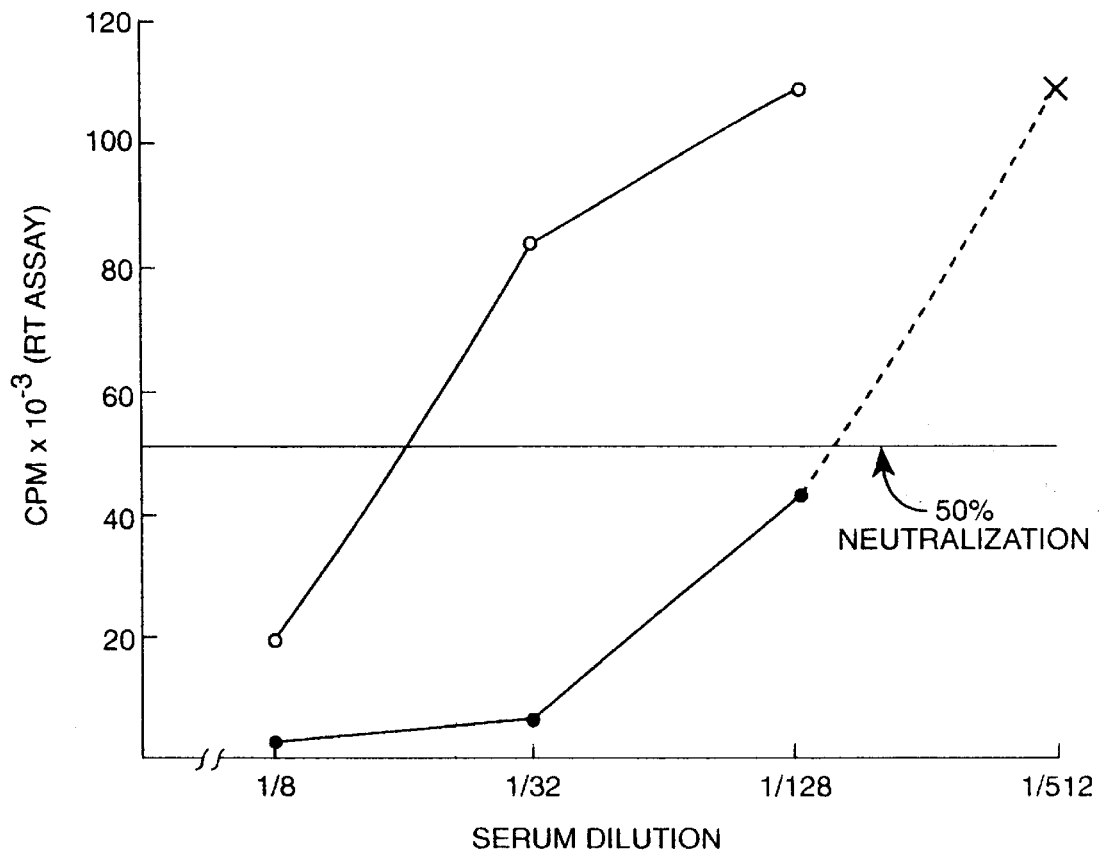
FIG. 4. Neutralization of HTLV-III$_B$ by goat anti-SP-10 antisera.

Goats were immunized subcutaneously with 28 mg of tetanus toxoid SP-10 conjugates (SP-10-TT) in Freunds complete adjuvant (days 0) followed by biweekly inoculations in incomplete Freunds adjuvant (days 14 and 28). Serum samples were collected after the second immunization and tested for the ability to inhibit (i.e. neutralize) HIV infection of H-9 T cells in vitro as measured by the presence of reverse transcriptase (RT) activity in cell culture supernatants (FIG. 4). Decreased cpm values obtained in RT assays reflect decreased levels of HIV after cocultivation of virus and cells for 10 days.

When pre-incubated with 100 infectious units of HTLV-III$_B$, goat anti-SP-10 antiserum neutralized the ability of HIV isolate HTLV-III$_B$ to infect H-9 T cells (●● 50% neutralization titer=1/145). In contrast, serum collected from the same goat prior to immunization did not appreciably neutralize HTLV-III$_B$ (O—O, 50% neutralization titer=1/16).

The original animal injected with SP-10-TT (whose serum neutralized HTLV-III$_B$ in reverse transcriptase assay) was subsequently injected with additional doses of SP-10-TT (0.5 mg/kg body weight). The 50% neutralization titer rose to 1:1600 after two injections. Neutralization data from these and other experiments with SP-10-like peptides are shown in Table XII as the serum dilutions that result in 80% rather than 50% neutralizations of HIV.

In addition, a second goat was injected twice with 0.5 mg/kg doses of SP-10-TT. Serum from the second goat neutralized HTLV-III$_B$ at a titer of 1:100. Importantly, both sera against SP10-TT raised in goats also inhibited HTLV-III$_B$ infectivity of T cells in the syncytium-inhibition assay (Table XII).

The syncytium-inhibition assay (Lifson et al., *Nature* 323:725, 1986) measures the ability of antibodies to inhibit the fusion of HIV-infected T cells, those expressing HIV gp120 envelope protein on the cell surface, with CD4 (T4)+ uninfected T cells. The CD4 (T4) molecule serves as the receptor for the AIDS virus (Maddon et al., *Cell* 47:333, 1986). The result of fusion of these two cell types is the formation of giant cells that are infected with HIV. In many instances, the result of HIV infection of cells and giant cell formation is death of the infected cell (Zagary et al., *Science* 231:850, 1986).

TABLE XII

EFFECT OF ANTI-SP-10 ANTISERA ON INFECTIVITY OF HIV ISOLATES HTLV-III$_B$, HTLV-III$_{RF}$, AND HTLV-III$_{HN}$

| Goal # | Inoculum[1] | # of Immunizations | Days Post Immunization | Syncytium Inhibition[2] Using HIV Isolates | | Neutralization of[3] HIV Isolates | | |
|---|---|---|---|---|---|---|---|---|
| | | | | III$_B$ | III$_{RF}$ | III$_B$ | III$_{RF}$ | III$_{HN}$ |
| 70 | SP-10 IIIB-TT | 0 | 0 | — | — | <10 | <10 | <10 |
| | | 2 | 29 | — | — | 50 | <10 | <10 |
| | | 3 | 22 | +(40) | — | 600 | <10 | <10 |
| | | 4 | 96 | +(>80) | — | 250 | <10 | <10 |
| | | 5 | 112 | +(>80) | — | ND | ND | ND |

TABLE XII-continued

EFFECT OF ANTI-SP-10 ANTISERA ON INFECTIVITY OF HIV ISOLATES
HTLV-III$_B$, HTLV-III$_{RF}$, AND HTLV-III$_{HN}$

| Goal # | Inoculum[1] | # of Immunizations | Days Post Immunization | Syncytium Inhibition[2] Using HIV Isolates | | Neutralization of[3] HIV Isolates | | |
|---|---|---|---|---|---|---|---|---|
| | | | | III$_B$ | III$_{RF}$ | III$_B$ | III$_{RF}$ | III$_{HN}$ |
| 86 | SP-10 IIIB-TT | 0 | 0 | — | — | <10 | <10 | <10 |
| | | 1 | 19 | — | — | <10 | <10 | <10 |
| | | 2 | 23 | +(10) | — | 100 | <10 | <10 |
| | | 3 | 48 | +(10) | — | ND | ND | ND |
| 69 | SP-10 IIIB(C) | 0 | 0 | — | — | ND | ND | ND |
| | | 3 | 43 | +(20) | — | ND | ND | ND |
| 76 | SP-10 RF(A)-TT | 0 | 0 | — | — | ND | ND | ND |
| | | 1 | 15 | — | +(40) | ND | ND | ND |
| | | 2 | 29 | — | +(>80) | ND | ND | ND |
| | | 3 | 43 | — | +(>80) | ND | ND | ND |
| 84 | SP-22 IIIB-TT (control) | 0 | 0 | — | — | <10 | <10 | <10 |
| | | 2 | 23 | — | — | <10 | <10 | <10 |
| | | 3 | 48 | — | — | ND | ND | ND |
| 80 | TT-HBS (control) | 0 | 0 | — | — | ND | ND | ND |
| | | 2 | 21 | — | — | ND | ND | ND |

Synthetic peptides were coupled to tetanus toxoid (TT) with m-maleimidobenzoyl-N-hydroxysuccinimide ester (HDS).
SP-10 RF(A)-CHKSITKGPGRVIY; SP-10 IIIB(C):CTRKSIRIQRCPCRY
Values in parentheses are the inverse of serum dilutions that inhibited the number of syncytia (60–80) per well) by >80%.
Neutralization was determined by evaluation of reverse transcriptase activity in supernatants of H-9 cells cultured for 10 days in the presence of 100 infectious units of HIV isolates. Values are inverse of anti-serum dilutions that inhibited reverse transcriptase activity by >HOX.
ND, NOT DONE Therefore, the above-described ability of goat anti-SP-10 sera to inhibit HTLV-III$_B$ infectivity in the syncytium inhibition assay and in the reverse transcriptase assay, indicated that anti-SP-10 antibodies are capable of blocking the binding of HIV gp120 protein to T cell CD4 (T4) molecules. In addition, goat antiserum raised to a peptide [SP-10 RF(A)] containing SP-10-like sequence from HIV isolate HTLV-III$_{RF}$ inhibited syncytium formation by HTLV-III$_{RF}$ but not by HTLV-III$_B$, indicating that type-specific antigens contained in SP-10 RF(A) are suitable as vaccine components to raise antibodies that inhibit the interaction of HTLV-III$_{RF}$ gp120 and T cell CD4 (T4) molecules.

EXAMPLE 5

Induction of Antibodies Capable of Inhibiting HIV gp120-CD4 (T4) Interactions A series of studies were undertaken to determine 1) whether the SP-10 peptide conjugated either to bovine albumin or to tetanus toxoid, exerted any inhibitory effect on antigen-specific, CD4 (T4) dependent, T cell responses in vitro; and 2) whether the anti-SP-10 antiserum (described in Example 4) bound to human white blood cell populations not infected with HIV.

When the SP-10 peptide was added directly in vitro human uninfected peripheral blood lymphocyte cultures stimulated with tetanus toxoid, no inhibition of normal T cell response to tetanus toxoid was observed (Table XIII).

TABLE XIII

SP-10-TT and SP-10-BSA DO NOT INHIBIT ANTIGEN SPECIFIC PROLIFERATIVE RESPONSES OF NORMAL HUMAN PERIPHERAL BLOOD LYMPHOCYTES

| Additive to Normal Human Peripheral Blood Lymphocytes in Culture | Exp. No. 1 | Exp. No. 2 |
|---|---|---|
| | CPM × $10^6$ Lymphocytes | |
| Media Alone | 3,900 | 3,100 |
| TT Alone (1:32) | 175,000 | 61,000 |
| SP-10-TT Alone (1 mg/ml) | 285,500 | 100,400 |
| SP-10-TT (1 mg/ml) + TT (1:32) | 269,500 | 94,400 |
| SP-10-BSA Alone (1 mg/ml) | 8,500 | 35,800 |
| SP-10-BSA (1 mg/ml) + TT (1:32) | 262,900 | 144,200 |

TT = Tetanus toxoid (Wyeth Laboratories, Philadelphia, Pa.), BSA = bovine serum albumin.
CPM = counts per minute of tritiated thymidine incorporation as described (Denning et al J. Immunol. 138:680, 1987).

As seen in Table XIII, SP-10-TT alone was as good an antigen-specific T cell activator as TT alone. Moreover SP-10-TT and SP-10-BSA when added to TT alone did not inhibit TT induced proliferation by normal T cells. In addition, anti-SP-10 goat serum did not bind to peripheral blood lymphocytes or monocytes in indirect immunofluorescence assay using flow cytofluorometry.

These data indicate that the SP-10 peptide does not perturb normal human T cell function that is dependent on a functional CD4 (T4) molecule but does induce antibodies that will inhibit HIV gp120-CD4 (T4) interactions and neutralize HIV in reverse transcriptase inhibition assays.

Thus, vaccines comprising the small synthetic SP-10-like peptides (less than or equal to about 35 amino acids in length) have distinct advantages over HIV vaccines comprising recombinant gp120, or large subunits thereof, as the latter may interfere with normal immune function.

EXAMPLE 6

Isolate Specific Neutralization of HIV

Synthetic peptide SP-10 has an amino acid sequence derived from and unique to the gp120 envelope protein of HIV isolates HTLV-III$_B$ and LAV, while other HIV isolates have varying degrees of differing amino acid sequences in their SP-10-like gp120 envelope proteins. Synthetic peptide SP-10 (that is, SP-10-III$_B$) from the HTLV-III$_B$ isolate of HIV was coupled to tetanus toxoid and used to raise antibodies in goats (0.5 mg of conjugate per kg goat body weight) as described by Palker et al. (*Proc. Nat'l. Acad. Sci. (USA)* 84:2479, 1987). Goat antibodies raised to synthetic peptide SP-10 were tested for the ability to neutralize four different HIV isolates (FIG. 5A: HTLV-III$_B$, FIG. 5B: HTLV-III$_{RF}$, FIG. 5C: HTLV-III$_{MN}$, FIG. 5D: HTLV-III$_{SC}$). Goat anti-SP-10 antiserum (●pre-immune goat serum (O) and AIDS patient serum (■) all at a $\frac{1}{10}$ dilution were first incubated with dilutions ($10^{-1}$, $10^{-2}$, $10^{-3}$) of each virus isolate. Next, these virus isolates were tested for the ability to infect H-9 T cells by cocultivation of virus and cells for 10 days in vitro. Levels of HIV present in cell culture supernatants after 10 days in culture were estimated by measuring RT activity in supernatants, and results are expressed as cpm values obtained in RT assay. Increased cpm values in RT assay reflect increased levels of HIV in culture.

Figure 5A:
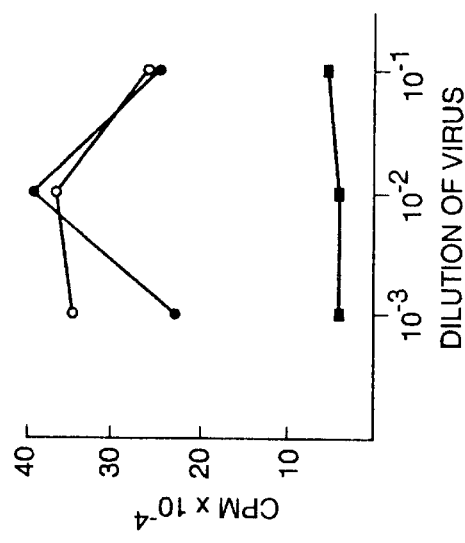
FIGS. 5A–5D. Isolate specific neutralization of HIV.
Figure 5B:
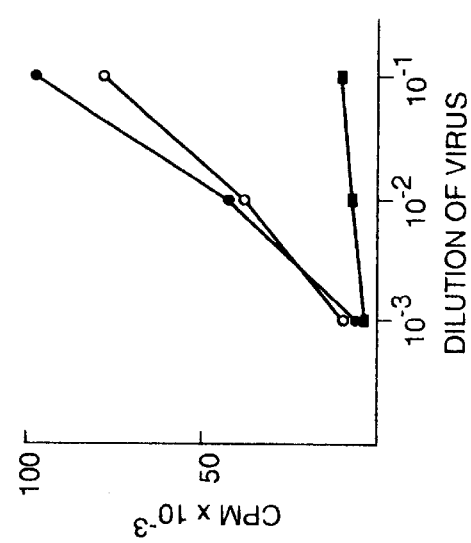
Figure 5C:
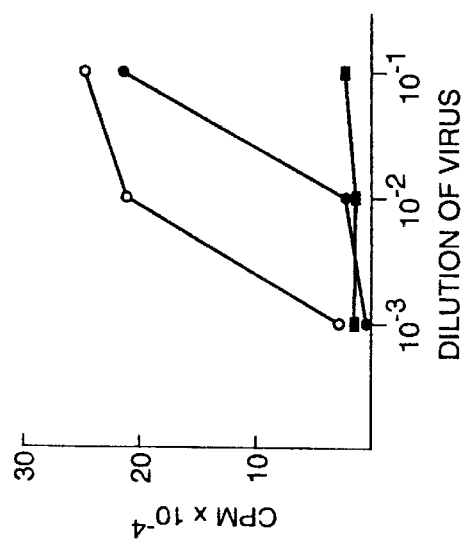
Figure 5D:
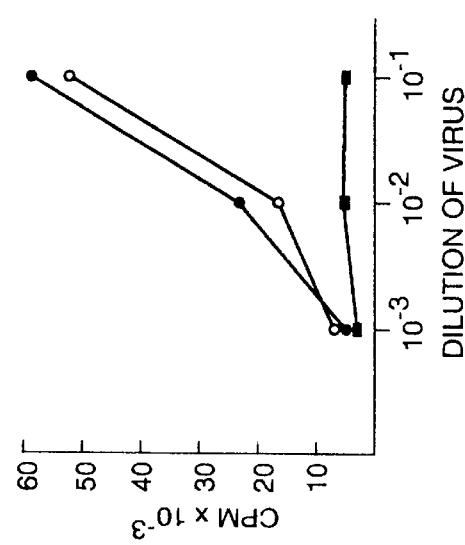

As shown in FIG. 5A, goat anti-SP-10 antiserum inhibited (i.e. neutralized) HTLV-III$_B$ infection of H-9 cells at a virus dilution of $10^{-2}$. Pre-immune goat serum did not inhibit HTLV-III$_B$ infection at the same dilution of virus. In contrast, goat anti-SP-10 antiserum did not neutralize other isolates of HIV (FIGS. 5B–D). AIDS patient antibodies neutralized all four isolates of HIV (FIGS. 5A–D). The data indicate that goat antiserum to synthetic peptide SP-10 neutralizes the HTLV-III$_B$ isolate that contains in its gp120 envelope protein the amino acid sequence present in SP-10. These data, along with data in Table XII, indicate that a vaccine comprising SP-10-like amino acid sequences from a variety of HIV isolates will be effective against a wide spectrum of HIV isolates.

EXAMPLE 7

Binding of Goat Anti-SP-10 Serum to HTLV-III$_B$- but not to HTLV-III$_{RF}$-Infected H9 T Cells The reactivity of goat anti-SP-10 serum and autologous prebleed control serum were compared on either uninfected H9 T cells, H9 T cells infected with HIV isolate HTLV-III$_B$, or H9 T cells infected with HIV isolate HTLV-III$_{RF}$ using flow cytofluorometry and a Coulter EPICS V cytofluorograph (Haynes, *Immunol. Rev.* 57: 127, 1981; Haynes et al., *New Eng. J. Med.* 304:319, 1981).

Figure 6A:
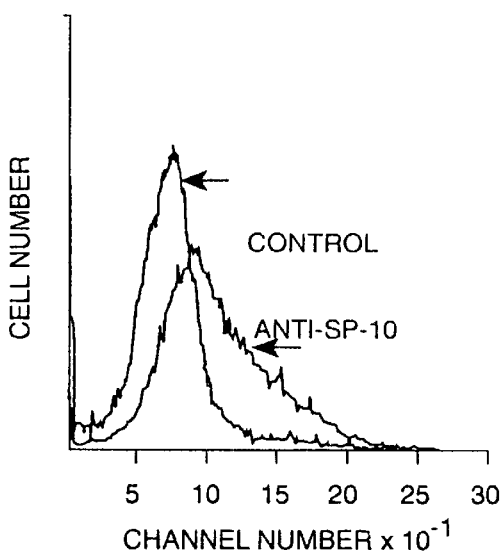
FIGS. 6A–6C. Binding of goat anti-SP-10 serum to HTLV-III$_B$- but not to HTLV-III$_{RF}$-infected H9 T cells.
Figure 6B:
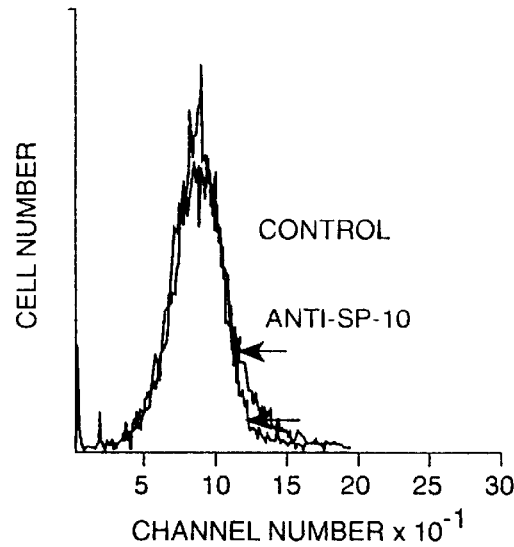
Figure 6C:
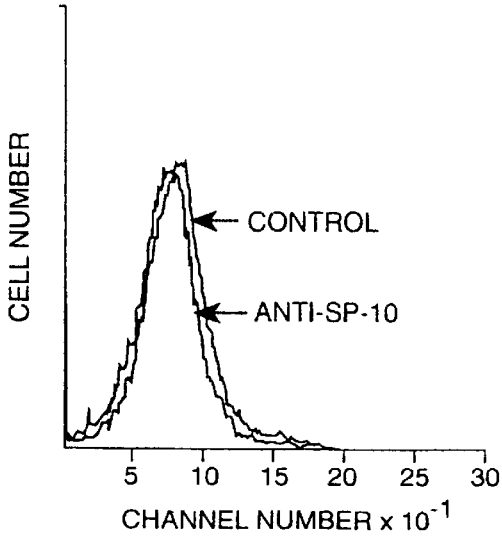

Goat anti-SP-10 serum (1:200) reacted with 40% of HTLV-III$_B$-infected H9 T cells compared to HTLV-III$_B$- infected H9 cells incubated with control (prebleed) goat serum (1:200) (FIG. 6A). Neither goat anti-SP-10 nor control (prebleed) serum (1:50) reacted with noninfected H9 T cells (FIG. 6B). Neither control (prebleed) nor anti-SP-10 serum (1:50) bound to H9 T cells infected with the HTLV-III$_{RF}$ isolate of HIV (FIG. 6C).

EXAMPLE 8

Development of a Synthetic Immunogen Comprising Multiple Regions of the Human Immunodeficiency Virus Envelope that Induces T Helper Cell, CD8+ Cytotoxic T Cell and B Cell Neutralizing Responses In Vivo In order to develop a synthetic peptide immunogen that induces cytotoxic T cell responses to HIV in addition to inducing neutralizing antibody and T helper cell responses, a series of peptides were prepared reflective of regions of the HIV MN isolate that have included therein a defined cytotoxic T cell epitope (see Table III). These studies were performed with the MN HIV isolate since it appears that this is the most common prototypic virus in the US at present (La Rosa et al *Science* 249:932, 1990).

Takahashi et al. (*Science* 246:118, 1989) have defined a cytotoxic T cell (CTL) epitope that includes amino acids 322–326 (FYTTK) from the MN HIV isolate and includes amino acids 323–329 of the HIVIIIB isolates (see Table IV) (Takahashi et al *J. Exp. Med.* 170:2023, 1989). Thus, one T1-SP10 variant peptide made was the T1-SP10MN(A) peptide with the (A) signifying that amino acids 322–326 were added to the existing MN SP10 region of amino acids 303–321 (see Table III). Secondly, to make a synthetic peptide that might insert into the cell membrane of antigen-presenting cells and therefore potentially be processed and expressed via MHC Class I molecules and therefore be recognized by CD8+ CTL, the first 12 amino acids of the gp41 HIV envelope protein (amino acids 519–530 AVGI-GALFLGFL in HIV isolate BH10/IIIB) were covalently linked N-terminal to T1-SP10 peptides. These amino acids (519–530) of HIV gp41 are highly hydrophobic. They have been postulated to be the primary amino acids that are capable of inserting into lipid membranes and to play a role in the ability of HIV to induce cell fusion (Brasseur et al *AIDS Res. Hum. Retrovirol.* 4:83, 1988). Peptides with this 12 amino acid gp41 sequence have the prefix F- before the name of the peptide (F for fusogenic region) (see Tables III and IV). Bosch et al (*Science* 244:694, 1989) have demonstrated that the homologous region in SIV (GVFVLGFLGFLATAG) to the F region in HIV (AVGIGALFLGFL) is indeed the SIV fusion envelope peptide. Thus, it was postulated that F-derivatized peptides might also insert into antigen presenting cell membranes, the F-derivatized peptides would be internalized and CD8+ MHC Class I restricted CTL would be generated in vivo following immunization with F-derivatized peptides. (Deres et al (*Nature* 342:561, 1989) have shown the conjugation of a fatty acid tripalmitoyl-S-glycerylcysteinyl-seryl-serine moiety to synthetic peptides can promote synthetic peptide processing and presentation in the context of MHC Class I molecules and lead to generation of CD8+ CTL in vivo.)

Figure 7:
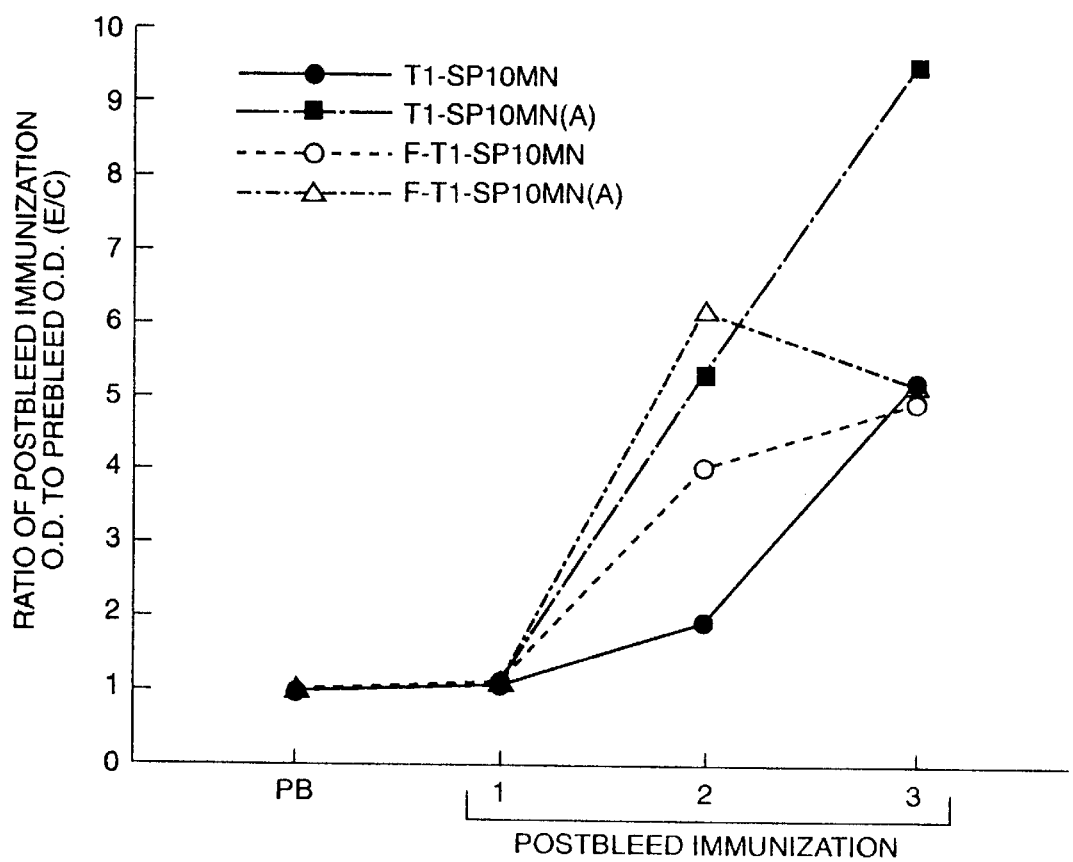
FIG. 7. Comparison of the ability of various T1-SP10 peptides from the envelope of HIV MN to induce anti-T1-SP10MN peptide antibodies in Balb/c mice. Each point represents the mean level of anti-T1-SP10 serum antibody in 4–5 mice as determined by ELISA assay in 96 well plates using the peptide T1-SP10 as antigen on the plate. Data are expressed as ratio (E/C) of postbleed immunization (E) optical density (OD) to prebleed (control) OD. Data show that T1-SP10MN(A), F-T1-SP10MN and F-T1-SP10MN (A) peptides after 2 immunizations induce higher levels of anti T1-SP10MN antibodies than did T1-SP10MN itself.
Figure 8:
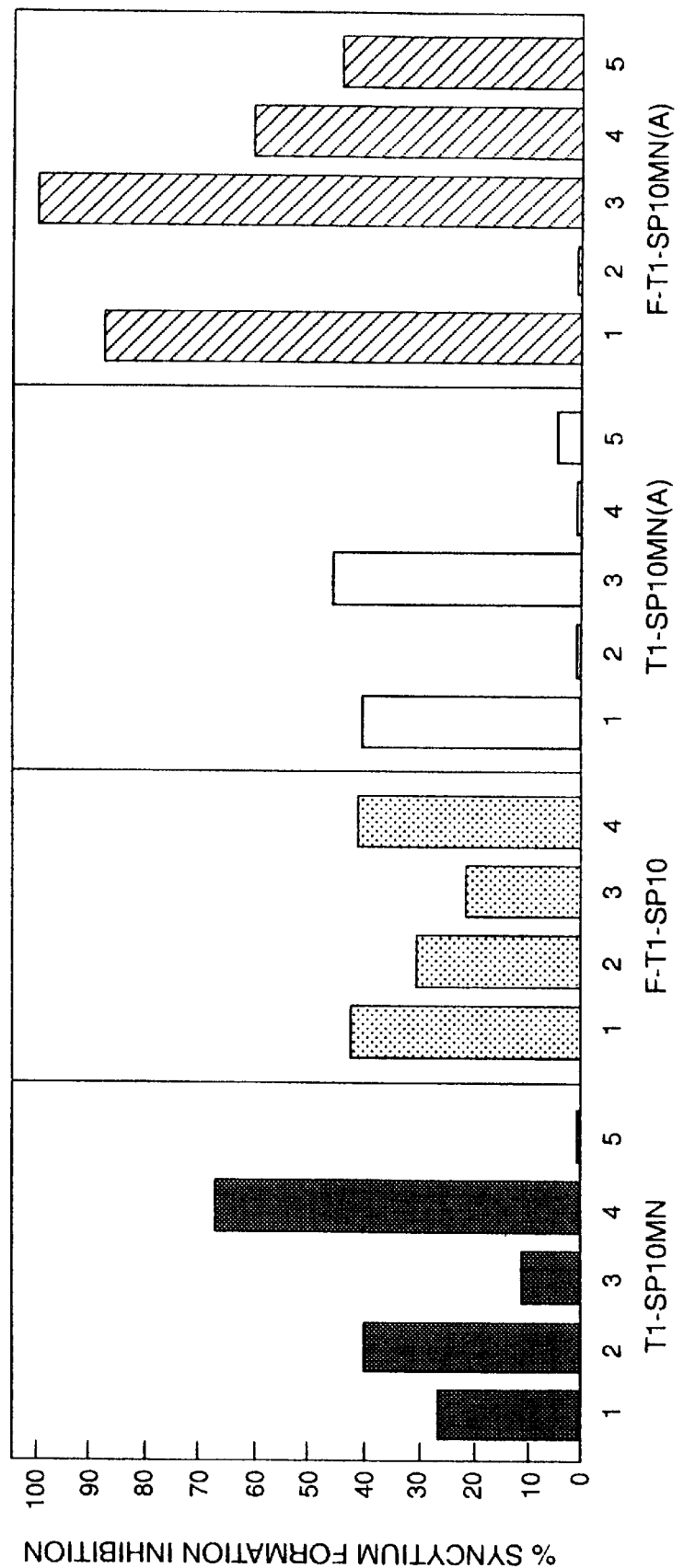
FIG. 8. Comparison of the ability of various T1-SP10 peptides from the envelope of HIV MN to induce antibodies in Balb/c mice that neutralize HIV MN in syncytium inhibitium assays in vitro. Each bar indicates the results of serum from bleed 3 from one mouse immunized with the indicated form of T1-SP10. Height of bar indicates the percent of syncytium formation inhibited by a 1:10 dilution of serum compared to prebleed serum at the same dilution.

A series of studies were performed in Balb/c mice with the MN series of T1-SP10 peptides (Table III) to compare their ability to induce anti-peptide antibodies (see FIG. 7), to compare their ability to induce anti-HIV neutralizing antibodies (FIG. 8), and to determine if any of these peptides could induce MHC Class I restricted CD8 CTL when injected in mice in vivo (Tables XIV and XV).

TABLE XIV

ABILITY OF F-T1-SP10MN(A) PEPTIDE TO INDUCE MHC CLASS I-RESTRICTED CD8+ CYTOTOXIC T CELLS IN VIVO IN Balb/c MICE

| Target Cell (Class I Type) | % Specific $^{51}$Cr Release at 50:1 E/T Ratio Exp. 1 | Exp. 2 | Exp. 3 |
|---|---|---|---|
| L51-78Y (H2$^d$) | 0 | 2 | 2 |
| T1-SP10MN(A) + L51-78Y (H2$^d$) | 33 | 47 | 23 |
| EL4 (H2$^b$) | 3 | 3 | 4 |
| T1-SP10MN(A) + EL4 (H2$^b$) | 2 | 4 | 3 |
| T1-SP10MN(A) + L51-78Y + C* | 32 | ND | ND |
| T1-SP10MN(A) + L51-78Y + Thy1.2 + C* | 4 | ND | ND |
| T1-SP10MN(A) + L51-78Y + Lyt2.2(CD8) + C* | 0 | ND | ND |
| T1-SP10MN(A) + L51-78Y + 172.4(CD4) + C* | 24 | ND | ND |

Soluble F-T1-SP10MN(A) peptide (10 μg) in PBS was injected subcutaneously in Balb/c mice in complete Freund's adjuvant (1st injection) and then incomplete Freund's adjuvant (2nd through 5th injections).
Effector cells were splenocytes of immunized animals grown for 7 days in vitro with 25 μg/ml F-T1-SP10MN(A) peptide in complete T cell media (Takahashi et al. J. Exp. Med. 170:2023, 1989). On day 3 of culture 10% v/v Con A supernatant was added. Con A supernatant was derived from Balb/c spleen cell stimulated 4 days with Concanavalin A 10 μg/ml in complete T cell medium (Takahashi et al. J. Exp. Med. 170:2023, 1989), and the supernatants removed and used in activation of spleen cytotoxic T cells.
*Experiments with complement (C) represent the results from pooled splenocytes from 3 mice immunized with F-T1-SP10MN(A).

TABLE XV

ABILITY OF T1-SP10MN(A) PEPTIDE IN LIPOSOMES TO INDUCE MHC CLASS I RESTRICTED CD8+ CYTOTOXIC T CELLS IN VIVO IN Balb/c MICE

| Target Cell (Class I Type) | % Specific $^{51}$Cr Release at 50:1 E/T Ratio Exp. 1 | Exp. 2 |
|---|---|---|
| L51-78Y (H2$^d$) | 16 | 0 |
| T1-SP10MN(A)-coated L51-78Y (H2$^d$) | 39 | 35 |
| EL4 or RL-12 (H2$^b$)* | 10 | 2 |
| T1-SP10MN(A)-coated EL4 or RL-12 (H2$^b$)* | 14 | 4 |
| T1-SP10MN(A) + L51-78Y + C | ND | 27 |
| T1-SP10MN(A) + L51-78Y + Lyt2.2(CD8) + C | ND | 2 |
| T1-SP10MN(A) + L51-78Y + 172.4(CD4) + C | ND | 31 |

Liposomes were prepared using Octylglucoside 7% (0.7 g/10 ml PBS) L-alpha dioleoyl lecithin, 20 mg/ml, T1-SP10MN(A) peptide and cholesterol 3.1 mg/ml using standard techniques (Mimms et al. Biochemistry 20:833, 1981; Liposome Technology Vol. III Ed. G. Gregoriadis Chapter 14 pp. 205–224, 1984.
Liposomes containing T1-SP10MN(A) peptide were injected into Balb/c mice in a total dose of 10 μg of T1-SP10MN(A) peptide in liposomes in 2 sites subcutaneously in complete Freund's adjuvant (1st dose) followed by incomplete Freund's adjuvant (2nd through 5th doses). Effector cells were splenocytes from immunized animals prepared and shown and described in Table XIV.
*Exp. 1 used RL-12 targets cells and Exp. 2 used EL4 target cells.

Comparison of the ability of various T1-SP10 peptides to induce anti-peptide antibodies in Balb/c mice:

FIG. 7 shows a comparison of the levels of anti-peptide antibody generated in the serum of Balb/c mice after 1, 2 and 3 immunizations with 10 μ/ml of the various peptides. FIG. 7 shows that after the second immunization, addition of either the (A) region or the F region increased the level of anti-peptide antibodies to the T1-SP10MN peptide in ELISA assay.

Comparison of the ability of various T1-SP10 peptides to induce anti-HIV neutralizing antibodies in Balb/c mice:

FIG. 8 shows the percent inhibition of HIV syncytium formation in vitro when antisera from bleed 3 were added to a HIV syncytium inhibition assay. Whereas only 1 animal in the T1-SP10 -injected group and none of the animals in the F-T1-SP10 and the T1-SP10(A) groups had serum antibodies that inhibited syncytium formation by greater than 50%, 3 of 5 animals in the group of animals injected with F-T1-SP10MN(A) had antibody levels that neutralized syncytium formation by greater than 50% (FIG. 8).

Ability of various T1-SP10 peptides to induce CD8+ CTL in vivo:

When injected into Balb/c mice, neither T1-SP10MN peptide nor F-T1-SP10MN peptide induced measurable CTL in Balb/c mice. However, soluble F-T1-SP10MN(A) peptide (Table XIV) and T1-SP10MN(A) peptide in liposomes (Table XV) when injected in vivo were capable of inducing anti-HIV CTL in Balb/c mice that killed T1-SP10MN(A) coated D' target cells in vivo. Table XIV shows that the cytotoxic T cells induced in Balb/c mice by the soluble F-T1-SP10MN(A) peptide in vivo were Thy1+, Ly2 (CD8)+. CD8+ anti-T1-SP10(A) cytotoxic T cells killed only H2' targets and did not kill H2' targets. Table XV shows that the anti-T1-SP10(A) cytotoxic T cells induced by T1-SP10(A) peptide in liposomes were CD8+ and MHC Class I restricted.

Thus, by addition of the F sequence and the (A) sequence (Table III) to the T1-SP10MN sequence, it was possible to construct a 52 amino acid peptide [F-T1-SP10MN(A)] capable of inducing not only neutralizing antibodies and helper T cell responses, but also capable of inducing CD8+ anti-HIV MHC Class I restricted cytotoxic T cells as well. In addition, MHC Class I restricted anti-HIV cytotoxic T cells have been induced in vivo by a 40 amino acid peptide, T1-SP10MN(A) incorporated into liposomes.

EXAMPLE 9

As has been shown, the construction of a synthetic peptide T1-SP10(A) containing aa303–327 of HIV gp120 V3 loop [SP10(A)] and aa 428–43 of HIV gp120 (T1) serves as a potent T cell immunogen for induction of activation of anti-HIV memory T helper cells and B cell immunogen for anti-HIV neutralizing antibodies in vivo (Palker et al., *PNAS* (*USA*), 85:1932–1936, 1988; Palker et al., *J. Immunol.,* 142:3612–3619, 1989; Hart et al., *J. Immunol.,* 145:2677–2685, 1990 and Hart et al., *PNAS* (*USA*), 88:9448–9452, 1991). The T1SP10(A) peptide induces anti-HIV neutralizing antibodies in mice, goats and rhesus monkeys (Palker et al., *PNAS* (*USA*), 85:1932–1936, 1988; Palker et al., *J. Immunol.,* 142:3612–3619, 1989; Hart et al., *J. Immunol.,* 145:2677–2685, 1990 and Hart et al., *PNAS* (*USA*), 88:9448–9452, 1991), induces anti-HIV MHC Class I-restricted CTL in mice (Hart et al., *PNAS* (*USA*), 88:9448–9452, 1991), and induces anti-HIV T helper cell responses in mice, goats, rhesus monkeys, and chimpanzees (Palker et al., *PNAS* (*USA*), 85:1932–1936, 1988; Palker et al., *J. Immunol.,* 142:3612–3619, 1989; Hart et al., *J. Immunol.,* 145:2677–2685, 1990 and Hart et al., *PNAS* (*USA*), 88:9448–9452, 1991). In a recently completed study in mice, it was found that while C57BL/6 and Balb/c mice make high titers of anti-peptide antibodies to T1SP10IIIB peptides, these mouse strains make no neutralizing antibodies to the HIVIIIB V3 loop neutralizing determinants. In contrast, C57BL6 and Balb/c mice make good anti-HIV neutralizing antibodies when immunized with T1SP10 peptides containing sequences from the HIVMN V3 loop.

Immunization trials in chimpanzees were conducted to test the synthetic peptides. The results discussed below show that the chimpanzees at Holloman AFT, New Mexico, made good antibody and good helper T cell responses to T1SP10IIIB(A) peptides, but like Balb/c mice, did not make antibodies against the neutralizing antibody determinants on the HIVIIIB V3 loop.

Figure 9A:
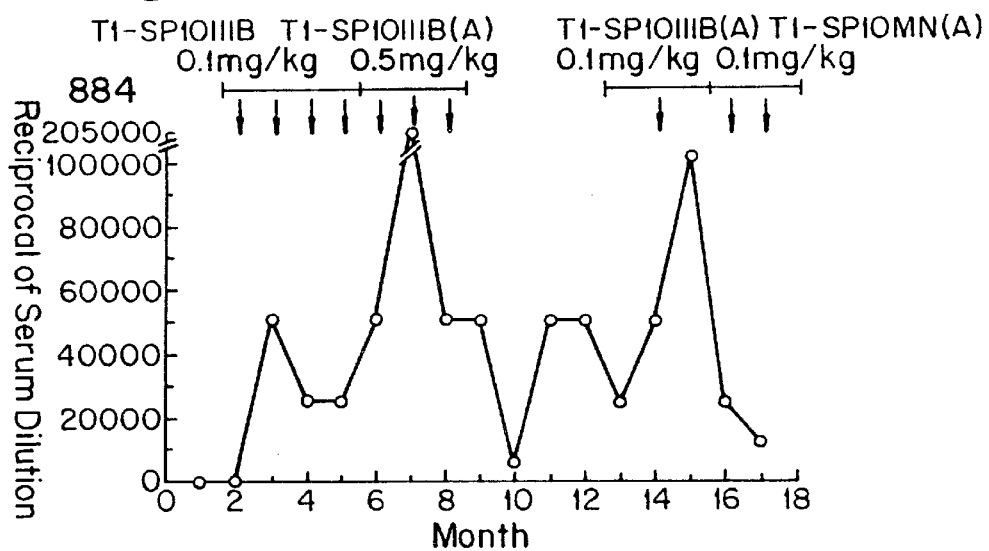
Figure 9B:
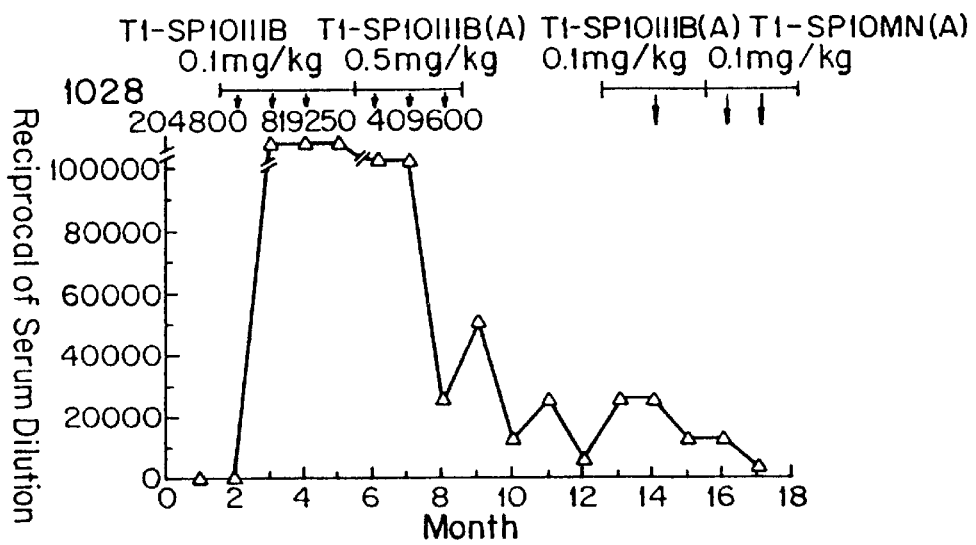
Figure 10A:
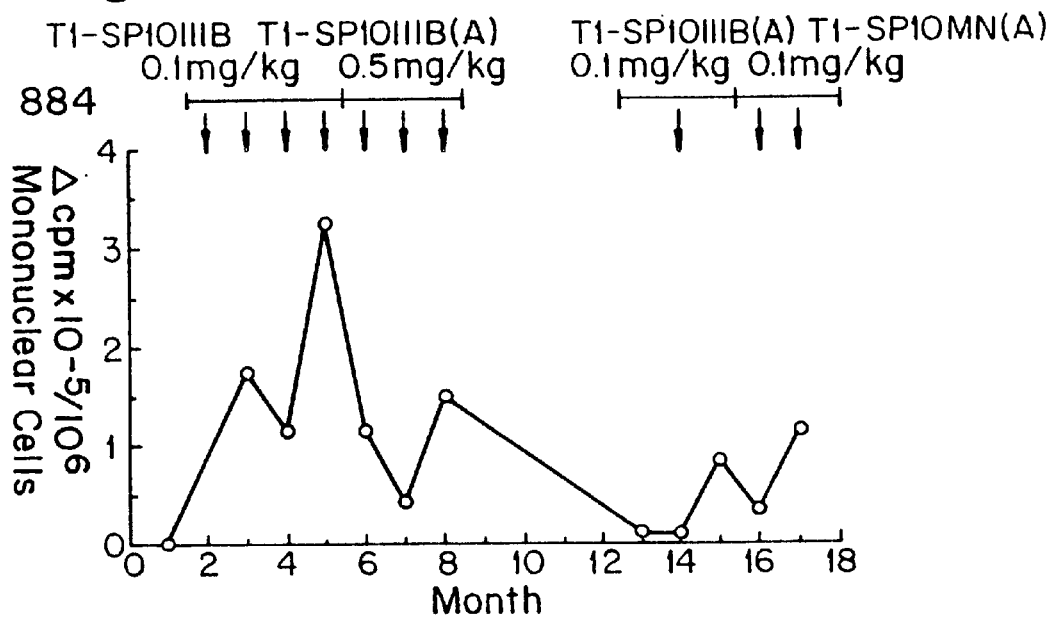
Figure 10B:
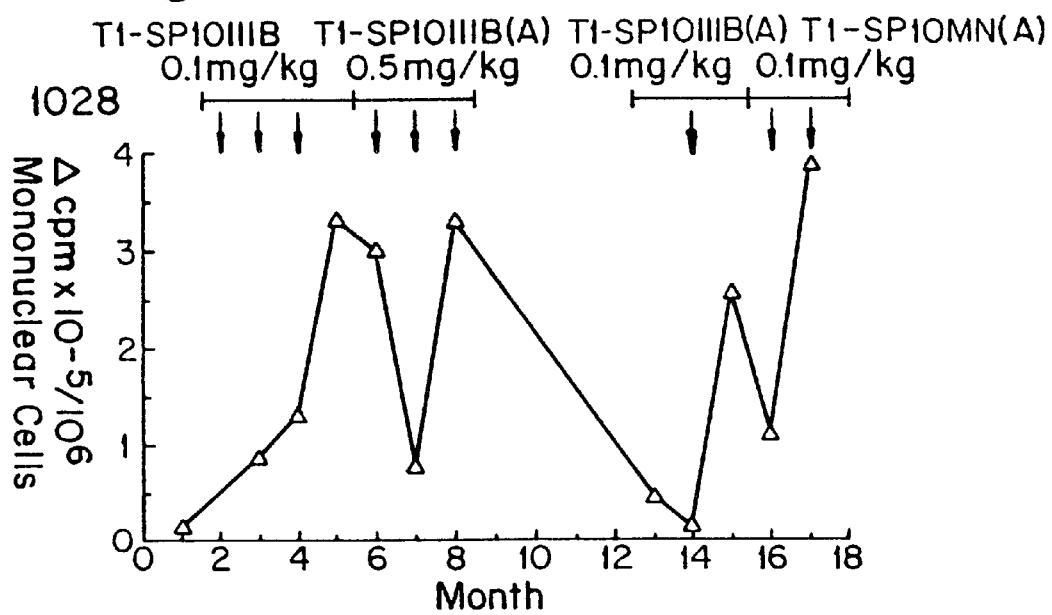
Figure 11A:
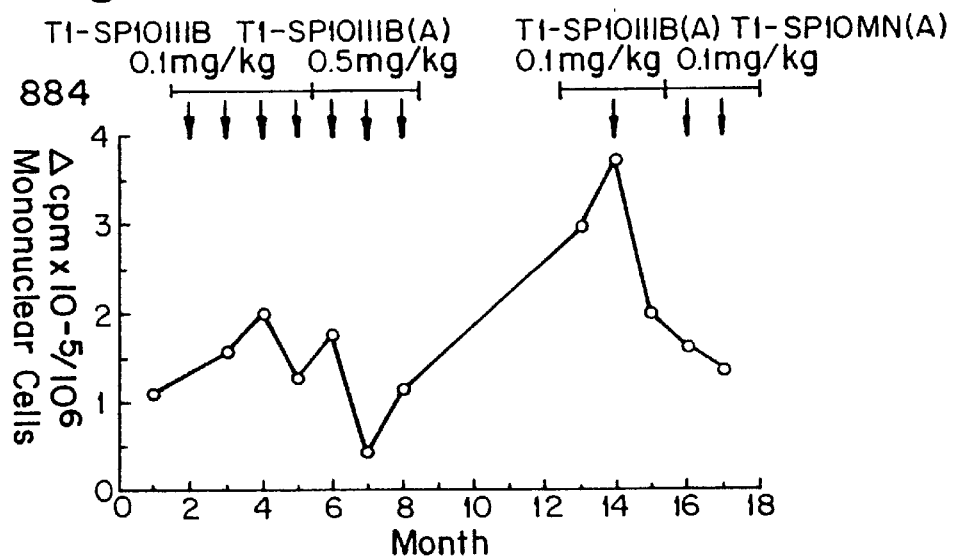
FIGS. 11A–11D show PBMC proliferative responses of chimpanzees immunized with T1-SP10 peptides and F-T1-SP10 peptides to PHA.
Figure 11B:
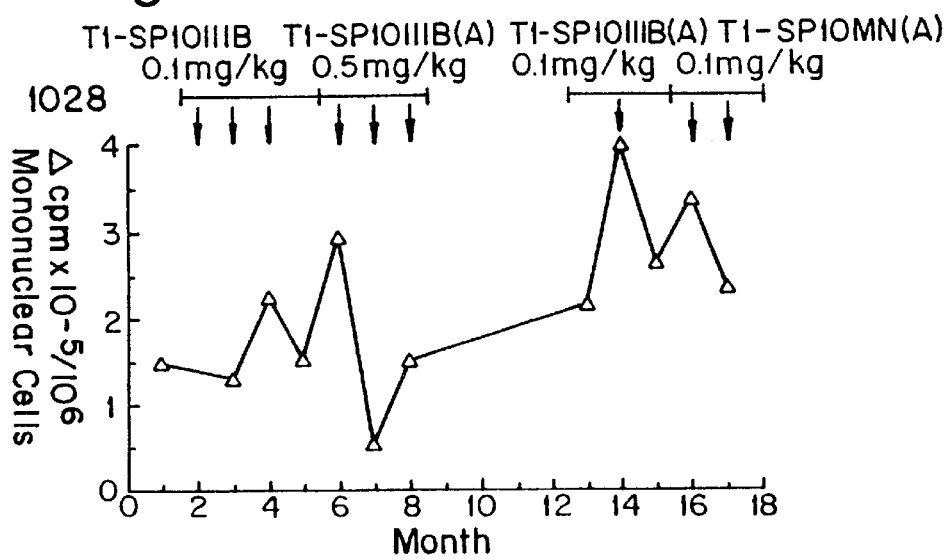
Figure 11C:
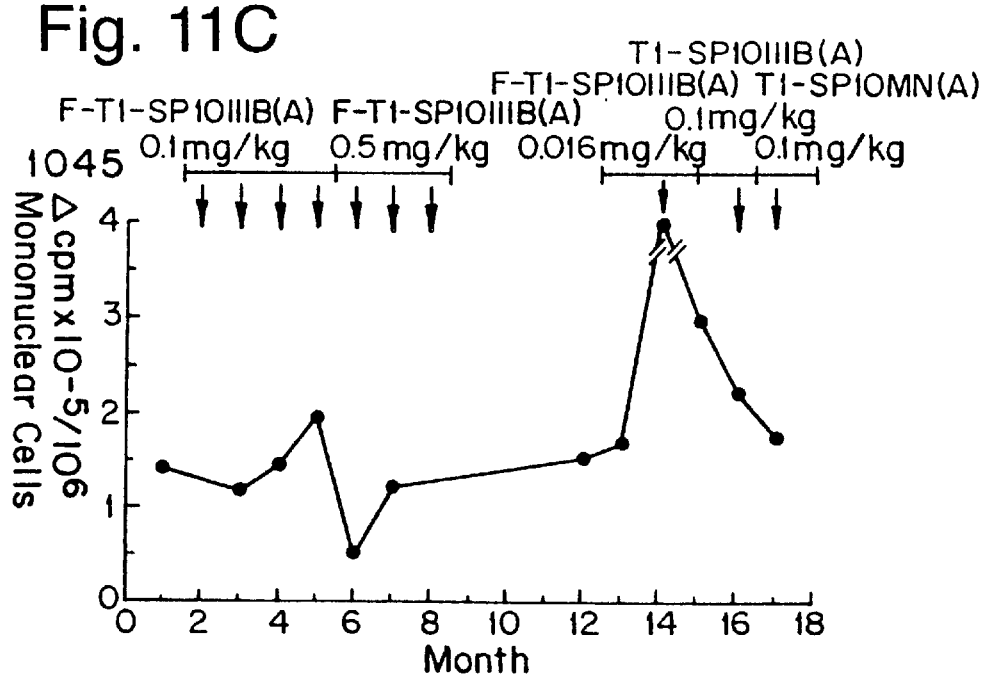
Figure 11D:
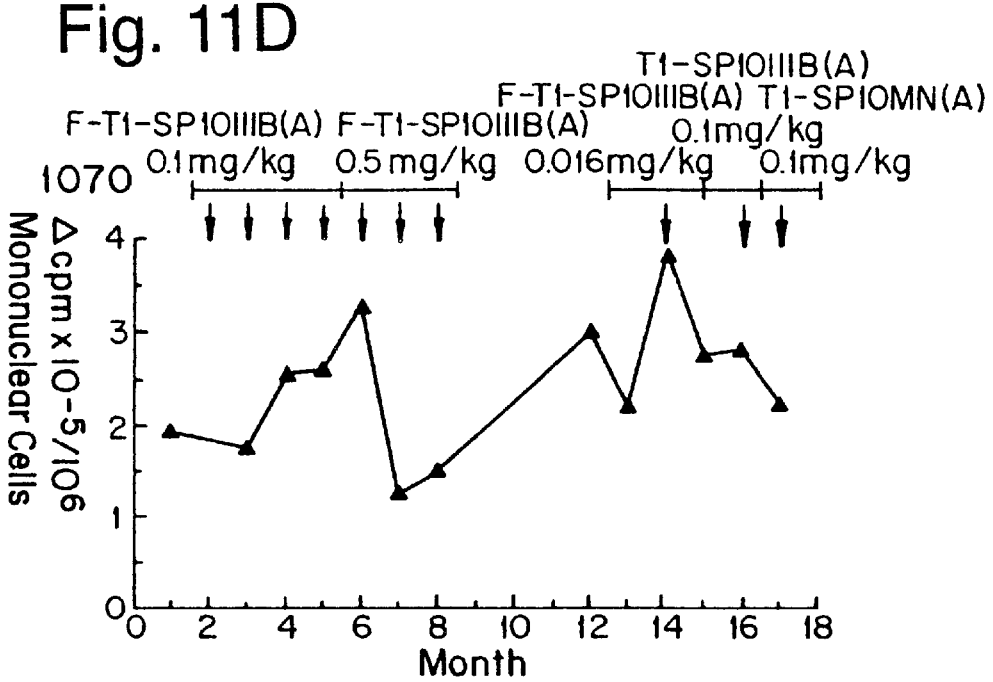
Figure 12:
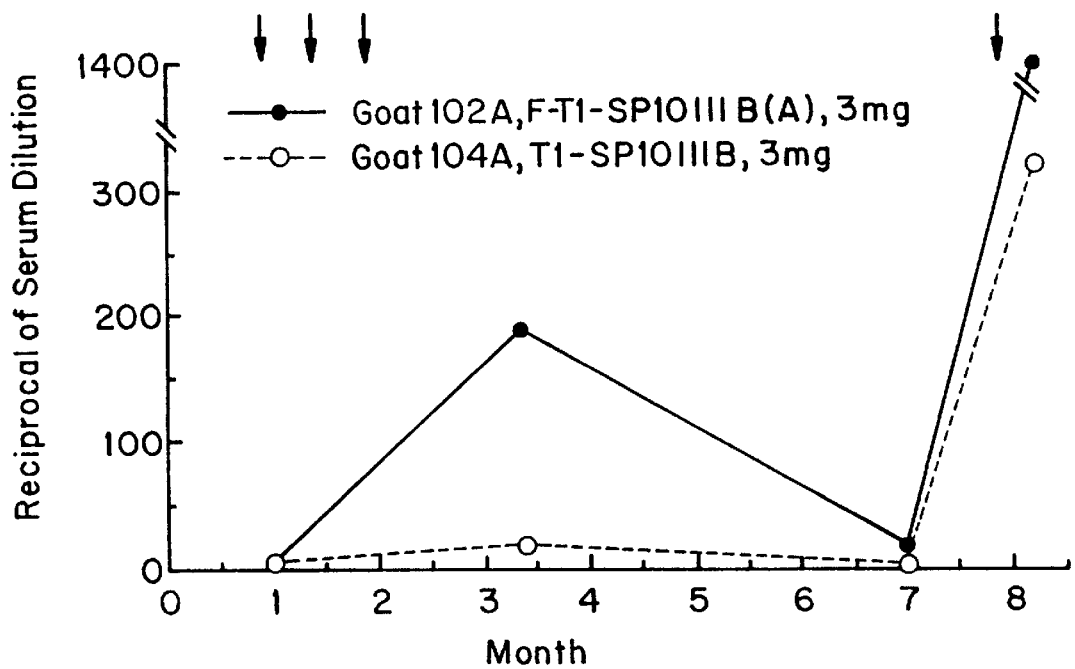
FIG. 12 shows goats immunized with the same batch of peptides used to immunize chimpanzees 884, 1028, 1045 and 1070. The peptides were immunogenic in goats and induced high titers of anti-HIVIIIB neutralizing antibodies.

In FIG. 9 the chimpanzees were immunized with HIV env synthetic peptides and their antibody titers tested using an ELISA assay. Animals 884 and 1028 were immunized with peptide T1-SP10IIIB which was also used in the ELISA assay. Peptide F-T1-SP10IIIB(A) was used in the immunization and ELISA assays for animals 1045 and 1070. All immunizations were in IFA+PBS (1:1) except for animal 1028 that developed IM abscesses after the third immunization and had one immunization held. Subsequent immunizations were given in PBS only.

As can be seen, T1-SP10 peptides were excellent immunogens in animals 884 and 1028, while T1-SP10 peptides with the HIV gp41 fusion (F) domain synthesized N-terminal to the T1-SP10 peptide did not induce antibody titers as high or as of long duration as did peptides without the F domain.

It should be noted that animals 1045 and 1070 were challenged at month 16 with the immunogen T1-SP10IIIB (A) that induced good antibody titers in animals 884 and 1028. Animals 1045 and 1028 did not respond to T1-SP10IIIB(A) in IFA, thus demonstrating that they were tolerant to the T1-SP10(A) peptide from their prior immunizations with F-T1-SP10IIIB(A) peptide. It is also important to note that while boost of animal 884 at week 14 gave a rise in titer to T1-SP10IIIB(A) peptide, boost of animal 1028 at the same time did not. Animal 884 was boosted with IFA, while boost of 1028 was with no adjuvant, but rather only PBS.

The peripheral blood mononuclear cell (PBMC) proliferative response to the immunizing peptides was also studied (see FIG. 10). Peptides T1-SP10IIIB and T1-SP10IIIB (A) induced high levels of proliferation of circulating PBMC in animals 884 and 1028. These levels fell to non-detectable levels after a 6 month rest (month 14) but rose again in animals 884 and 1028. Proliferative responses in animal 1028 rose with each boost after the 6 month rest even though the immunizations were in PBS alone with no adjuvant.

As with B cell responses, animals 1045 and 1070, that were immunized with F-T1-SP10IIIB(A) peptide, did not proliferate to T1-SP10IIIB(A) peptide. When these latter two animals were immunized with the T1-SP10IIIB(A) peptide that was a good immunogen in 884 and 1028, neither of the animals 1045, 1070 developed a proliferative response to T1-SP10IIIB(A) which proves that the addition of the F-domain N-terminal to the T1-SP10 peptide created a toleragen that tolerized animals 1045 and 1070 to the T1 and SP10 regions of gp120. As shown in Table XVI, while animals 884 and 1028 both responded in proliferative assays to native gp120, animals 1045 and 1070 were tolerant to native gp120 as well as to immunizing peptides.

The PBMC proliferative responses of chimpanzees immunized with the synthetic peptides to PHA was also studied (see FIG. 11). The data show that while animals 1045 and 1070 were tolerant to T1 and SP10 regions of HIV gp120, PBMC PHA responses in these animals throughout the immunization period were normal.

The same T1-SP10IIIB peptide batches used in the chimpanzee study, were also used as immunogens in goats, and good anti-HIV neutralization titers in goats were obtained (See FIG. 12). Thus, T1-SP10 peptides were superb immunogens with IFA in chimpanzees, with remarkable anti-peptide serum antibody titers of >1:102, 400 (See FIG. 9), and induction of T cell response to T1-SP10 and to native HIV gp120 (See FIG. 10 and Table XVI below).

TABLE XVI

Tritiated Thymidine Incorporation of Peripheral Blood Mononuclear Cells Following In Vitro Stimulation With HIV Env gp120*

| Chimpanzee No. | Immunogen | Pre-Immunization | Post-Immunization |
|---|---|---|---|
| | | δcpm/$10^6$ cells (Post/Pre) | |
| 884 | T1-SP10IIIB, then T1-SP10IIIB(A) | 169 | 39,189 (232) |
| 1028 | T1-SP10IIIB, then T1-SP10IIIB(A) | 17,955 | 129,121 (7) |
| 1045 | F-T1-SP10IIIB(A) | 6,348 | 12,256 (2) |
| 1070 | F-T1-SP10IIIB(A) | 11,285 | 22,719 (2) |

*Data represent the peak gp120 responses observed during the immunization period. Data for animals 884, 1028, and 1045 represent peak responses using from 2 ug/ml to 0.5 ug/ml of HIVIIIB(LAI) recombinant gp120. Data for animal 1070 represent peak responses using from 1 ug/ml to 0.5 ug/ml of native HIVIIIB(LAI) gp120.

TABLE XVII

Anti-HIVIIIB(LAI) Neutralizing Antibody Titers In Chimpanzees Immunized With Synthetic Peptides Containing T and B Cell Determinants of HIVIIIB(LAI) gp160 Envelop*

| Chimpanzee No. | Immunogen | Month 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| 884 | T1-SP10IIIB, then T1-SP10IIIB(A) | 0 | 0 | 0 | 0 | 0 | 0 | 0 | 0 | 45 | 0 | 21 | 23 | 0 | 24 | 0 | 0 | 22 |
| 1028 | T1-SP10IIIB, then T1-SP10IIIB(A) | 0 | 0 | 0 | 0 | 0 | 0 | 0 | 0 | 10 | 0 | 0 | 0 | 0 | 0 | 0 | 0 | 0 |
| 1045 | F-T1-SP10IIIB(A) | 0 | 0 | 0 | 0 | 0 | 0 | 0 | 0 | 12 | 0 | 0 | 0 | 0 | 0 | 0 | 0 | 0 |
| 1070 | F-T1-SP10IIIB(A) | 0 | 0 | 0 | 0 | 0 | 0 | 25 | 0 | 18 | 0 | 0 | 0 | 0 | 23 | 0 | 0 | 22 |

*Data represent 90% neutralization titers of HIVIIIB(LAI) (8 to 64 Infection Units per well) in reverse transcriptase inhibition assays in vitro.

TABLE XVIII

Syncytium Inhibition Serum Neutralizing Antibody Titers of Rhesus Monkey 18978 Immunized with 500 ug T1-SP10MN(A) Peptide

| Immunization No. | Date | NA Titer (HIVMN) | NA Titer (HIVIIIB) |
|---|---|---|---|
| 1 | 09/04/91 | 0 | 0 |
| | 09/18/91 | 0 | ND |
| 2 | 10/02/91 | 20 | 20 |
| | 10/16/91 | 40 | 40 |
| | 10/30/91 | 80 | 40 |

TABLE XVIII-continued

Syncytium Inhibition Serum Neutralizing Antibody Titers of Rhesus
Monkey 18978 Immunized with 500 ug T1-SP10MN(A) Peptide

| Immunization No. | Date | NA Titer (HIVMN) | NA Titer (HIVIIIB) |
|---|---|---|---|
|  | 11/13/91 | 40 | 40 |
| 3 | 12/04/91 | 40 | 10 |
|  | 12/18/91 | 80 | 40 |
|  | 01/08/92 | 20 | 20 |
|  | 01/23/92 | 40 | 10 |
|  | 02/06/92 | 10 | 0* |

Nd = Neutralizing Antibody
Pd = Pending
ND = Not done
* = 68% inhibition of syncytia at 1:10 dilution.

The high neutralizing antibody responses of goats to the same T1-SP10 peptide batches used in chimpanzees demonstrated that chimpanzees selectively did not recognize the neutralizing V3 sequences as immunogenic, while other non-neutralization T1-SP10IIIB peptide sequences were immunogenic in chimpanzees. Thus, it is possible that selective proteolysis of the HIVIIIB V3 loop occurs by chimpanzee and mouse mononuclear cells in vivo, or more likely, that genetic restriction of antibody responses to neutralizing determinants of the V3 loop exist in chimpanzees and mice.

Figure 13:
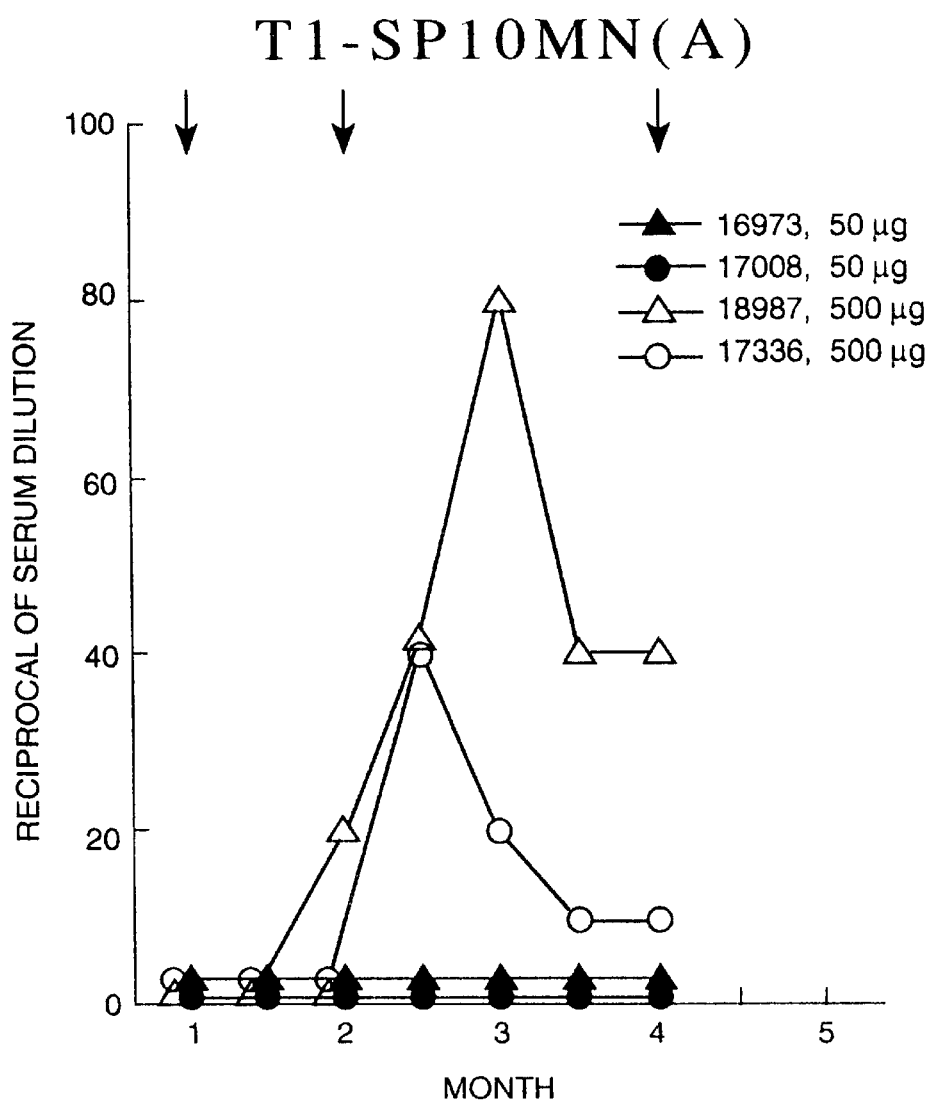
FIG. 13 shows anti-HIVMN neutralizing antibodies in Rhesus monkeys immunized with T1-SP10MN peptides. Data represent 90% neutralization titers in syncytium inhibition assay.
Figure 14:
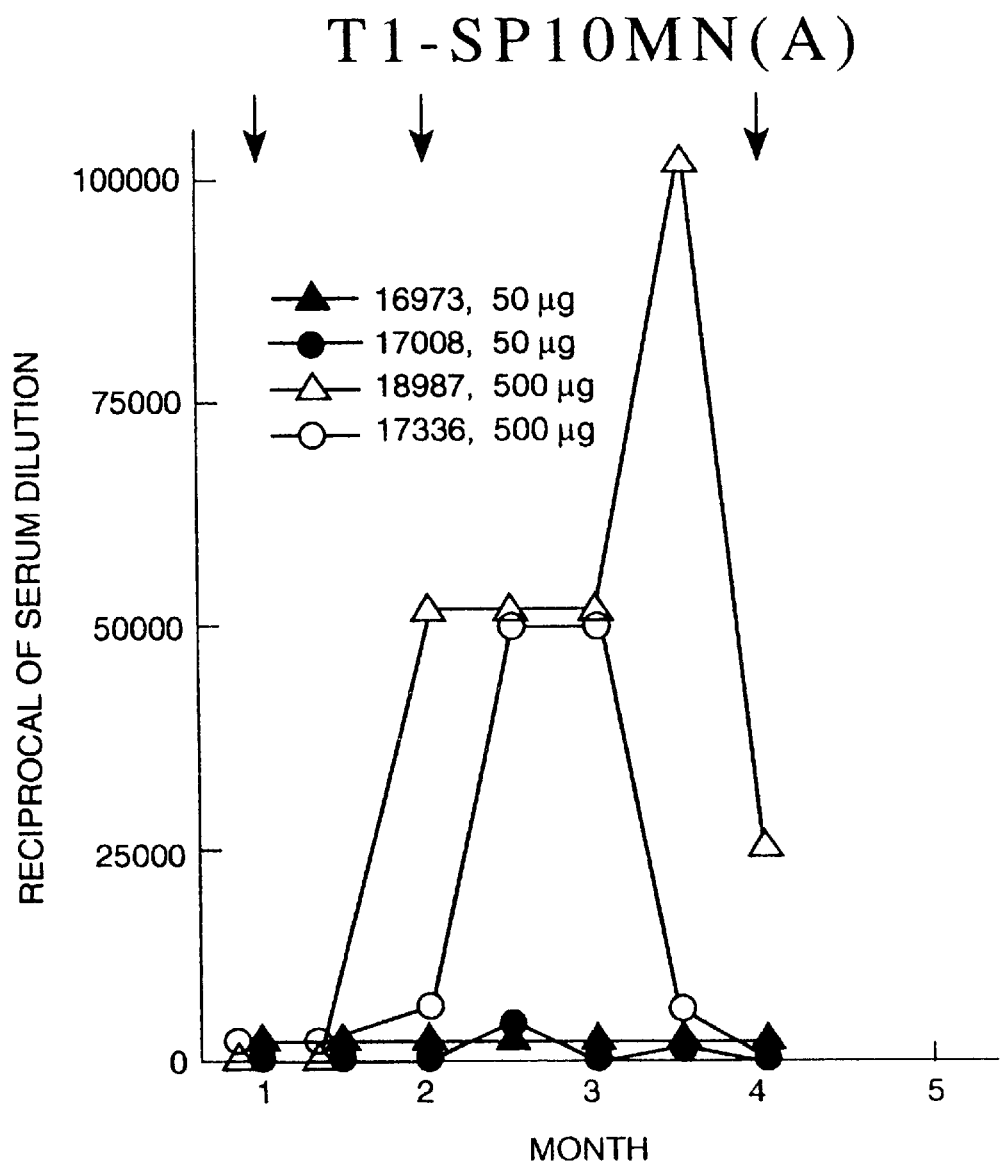
FIG. 14 shows antibody to immunizing peptide in Rhesus monkeys immunized with T1-SP10MN(A) peptide.
Figure 16:
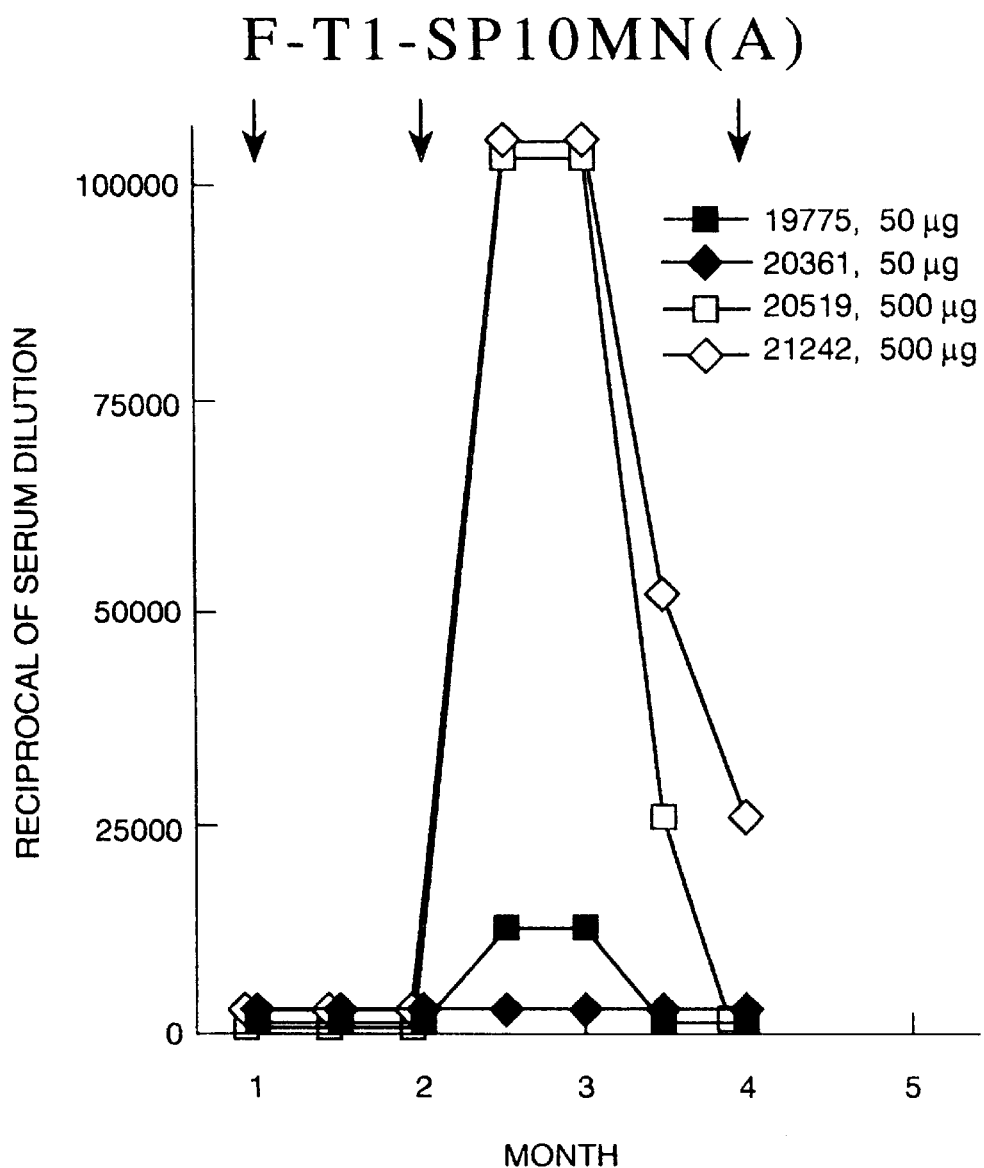
FIG. 16 shows serum antibody titers to immunizing peptide in Rhesus monkeys immunized with F-T1-SP10MN (A) peptide.
Figure 17:
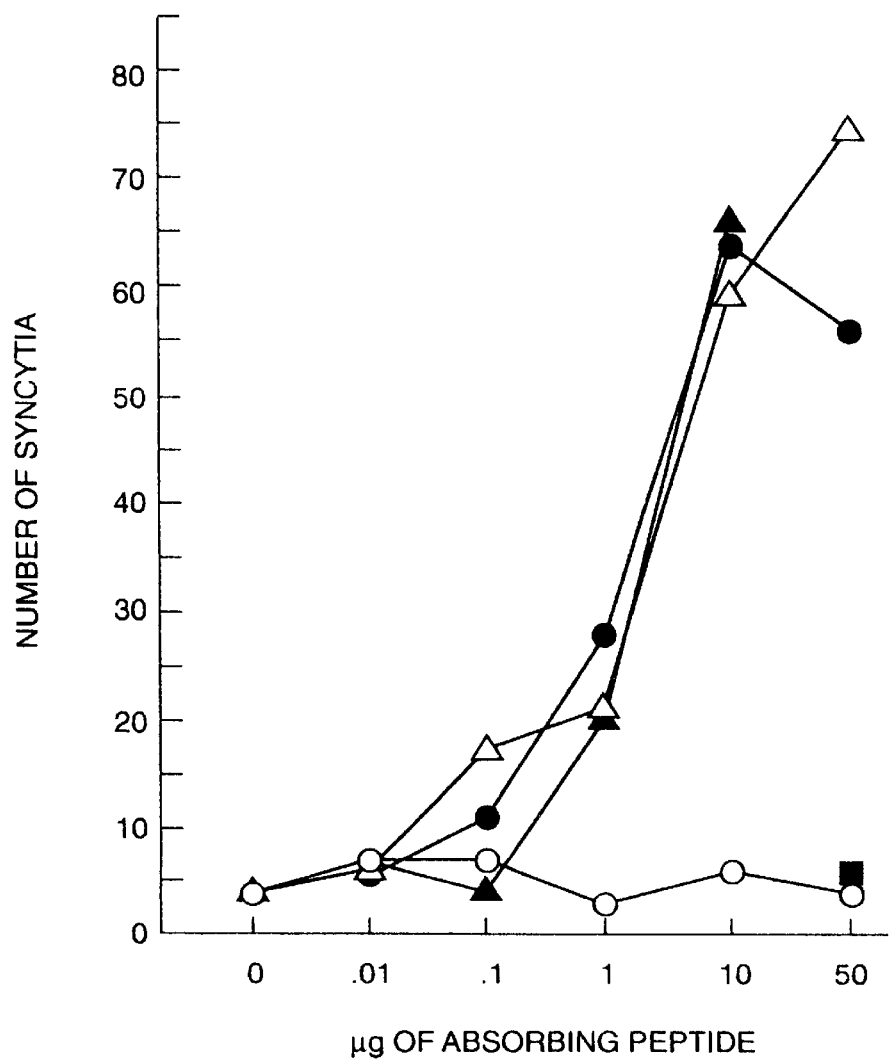
FIG. 17 shows the absorption of cross neutralizing antibodies induced by T1-SP10MN(A) peptide in rhesus monkey 18987 by peptides containing GPGRAF sequence. As shown, a peptide containing T1 did not absorb out neutralizing antibodies nor did a peptide with a sequence not in T1-SP10MN(A). Only peptides with GPGRAF absorbed the neutralizing activity proving that this animal selectively recognized the GPGRAF region of the V3 HIV gp120 loop as immunogenic and made cross-reactive antibodies to this region.
Figure 18A:
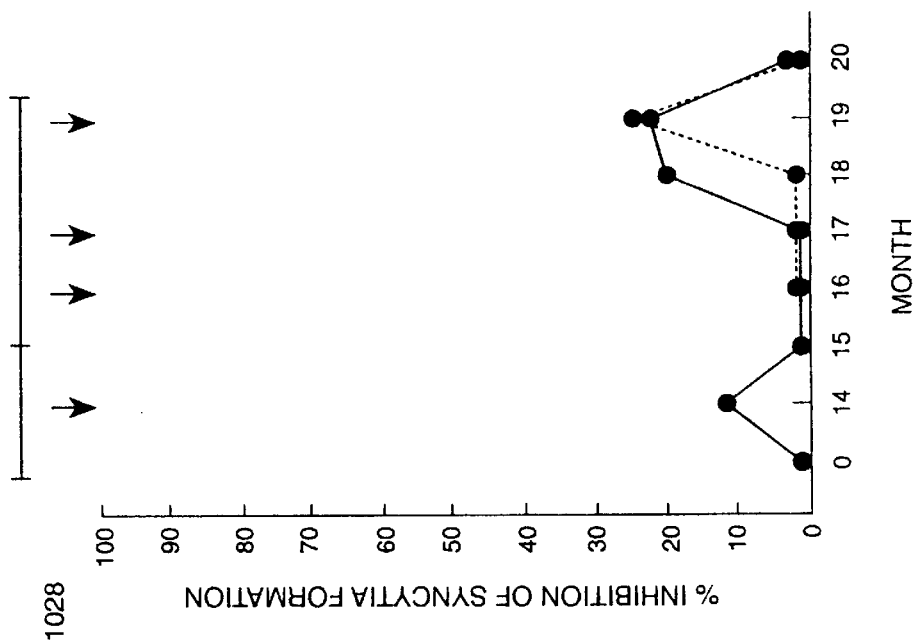
FIGS. 18A–18D. Neutralizing antibody titers against HIV IIIB/LAI (solid lines) and HIV MN (dotted lines) in serum of the four chimpanzees immunized with T1-SP10IIIB or F-T1-SP10IIIB(A) peptides then immunized with T1-SP10MN(A) peptide. Neutralizing antibody titers determined in syncytium inhibition assay.
Figure 18B:
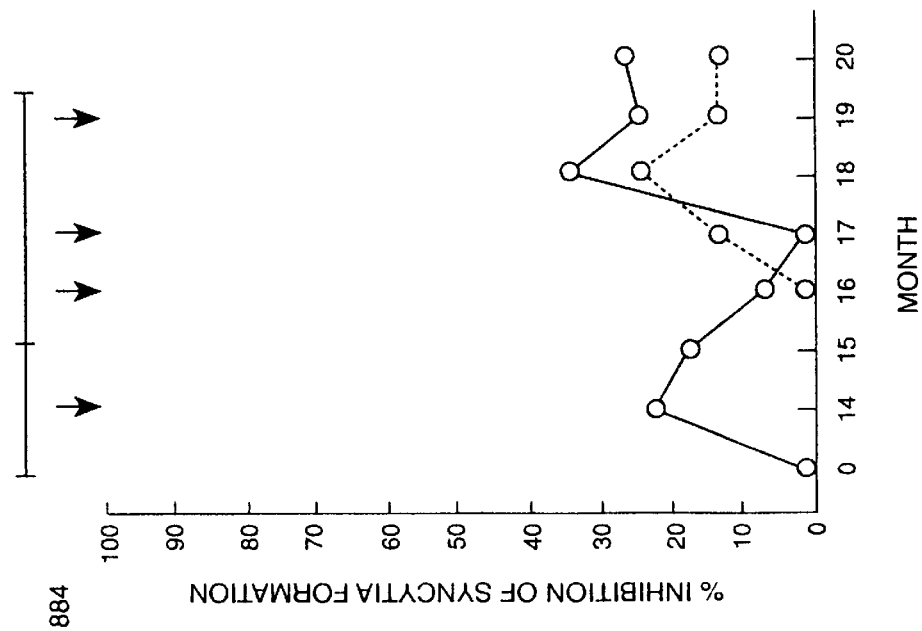
Figure 18D:
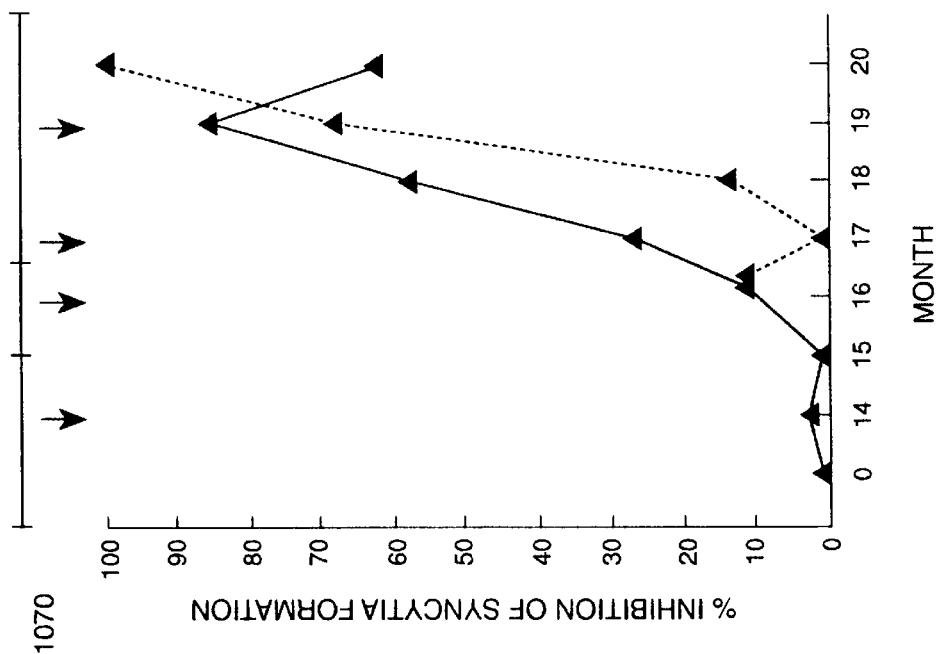
Figure 18C:
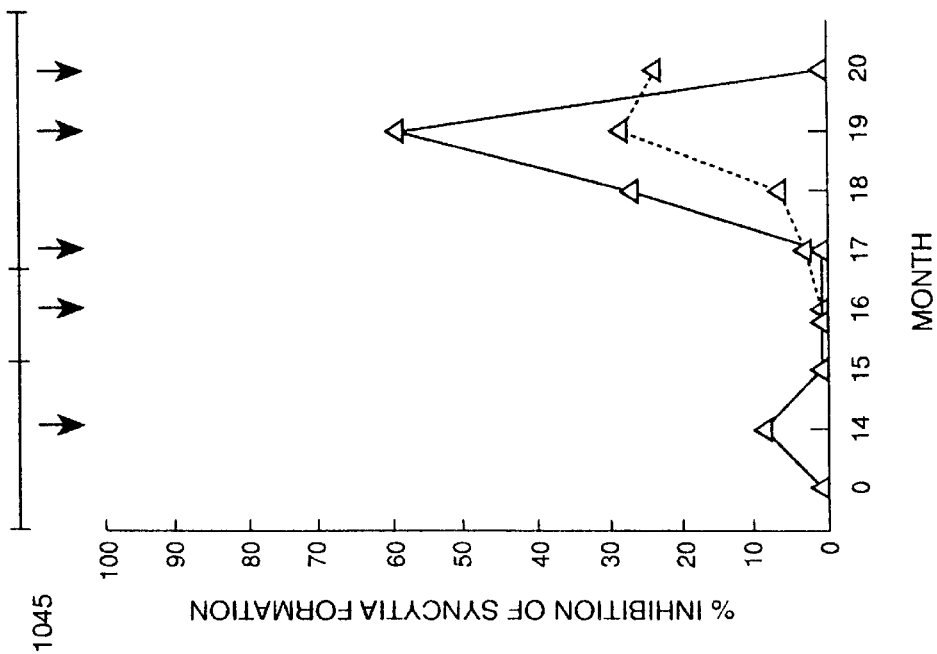

In rhesus monkeys, the injection of 500 ug of purified T1SP10MN(A) peptides was shown to yield very high levels of anti-HIVMN neutralizing antibodies in 4/4 animals (see FIGS. 13–15). In addition, in 1 out of 4 monkeys, immunization yielded cross-reactive anti-HIV neutralizing antibodies that neutralized the HIVIIIB and HIVMN viruses (see Table XVIII below). Thus, if 25% chimpanzees and humans respond to the T1-SP10MN(A) peptide and make cross-neutralizing anti-HIV env antibodies, then an additional 5% of subjects challenged with an otherwise non-MN-like HIV isolate could be protected from HIV challenge. See FIGS. 16 and 17 for additional monkey data.

Figure 19A:
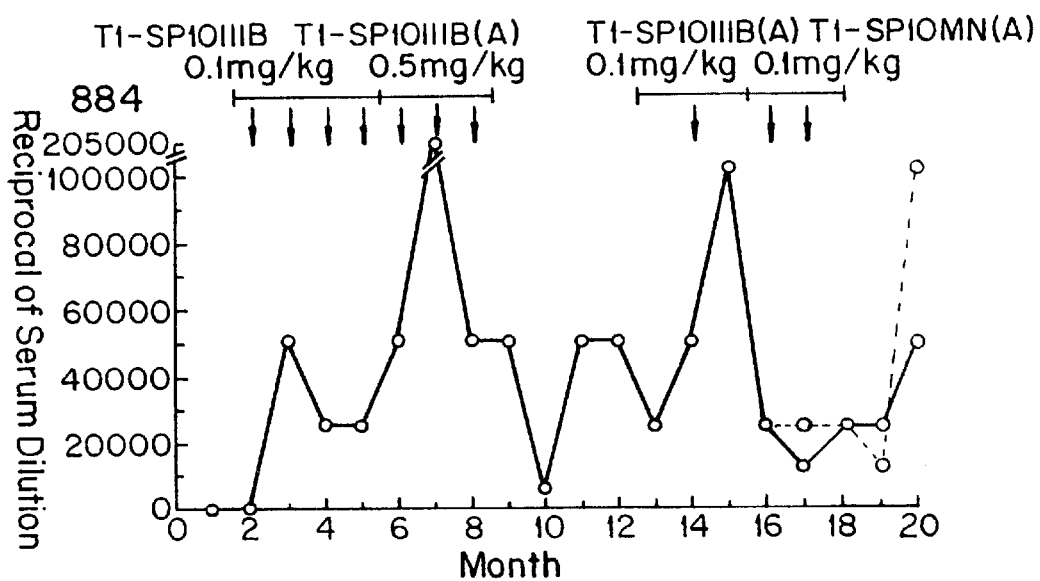
Figure 19B:
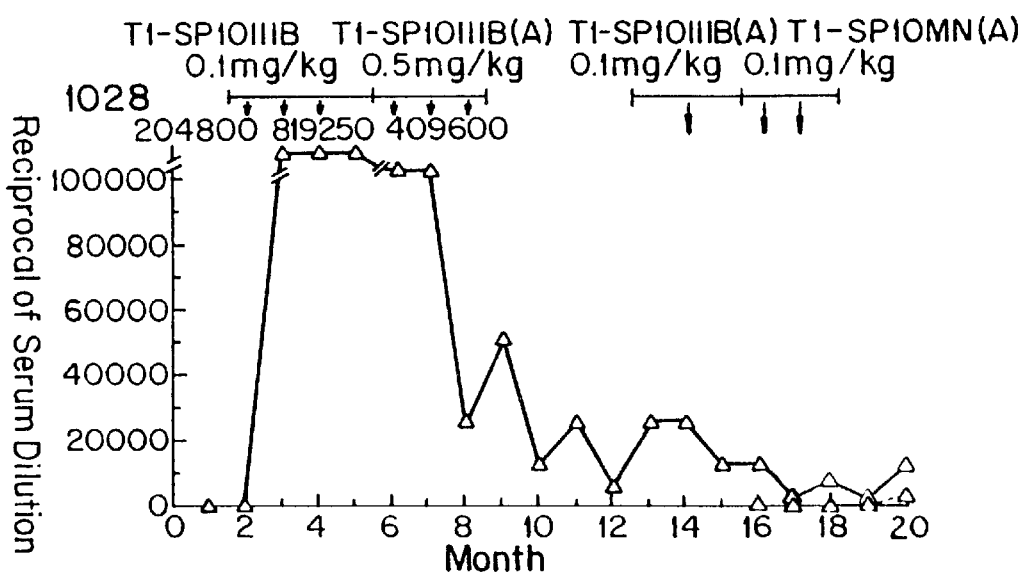

Because T1-SP10IIIB(A) peptides did not induce anti-HIVIIIB neutralizing antibodies in animals 884 and 1028, and because F-T1-SP-10III(B)A peptides induced tolerance in animals 1045 and 1070, all of the chimpanzees were immunized at either month 16 (animals 884, 1028) or month 17 (animals 1045, 1070) with T1-SP10MN(A) peptide. The rationale here was to determine A) if the T1-SP10MN(A) peptide could break tolerance in animals 1045 and 1070, and B) if any of the animals could genetically see the V3 neutralizing determinants of HIV MN V3 loop, since it appeared that none of the animals could see the V3 determinants of HIV IIIB as presented by T1-SP10IIIB peptides. FIG. 18 shows that after immunization of all 4 chimpanzees with 0.1 mg/kg of T1-SP10MN(A) peptide, three of the 4 animals (884, 1028 and 1045 showed the appearance of weak serum anti-HIV MN neutralizing antibodies (dotted lines), while animal 1070 developed high levels of anti-HIV MN neutralizing antibodies that titered to >80% neutralization at 1:20, and also cross-neutralized HIV IIIB (Table XIX, solid lines, FIG. 18). This break in tolerance can also be seen in the rise in titer to T1-SP10MN(A) peptide in the serum of animals 884, 1045 and 1070 (FIG. 19). Animal 1028 had an early abscess associates with the immunizations and did not receive IFA after month 4 of the study, and never had an antibody rise to peptide of HIV after the initial immunization of peptide with IFA.

TABLE XIX

Neutralization of HIV LAI/IIIB And HIV MN in Syncytium Inhibition
Assay In Chimpanzees Immunized with T1-SP10 Peptides

| Animal No. | 1-7-92 | | 2-4-92 | | 3-3-92 | |
|---|---|---|---|---|---|---|
|  | LAI/IIIB | MN | LAI/IIIB | MN | LAI/IIIB | MN |
| Presence of Neutralization in Syncytium Inhibition Assay (Reciprocal Titer in RT Inhibition Assay) | | | | | | |
| 884 | – | – | – | – | – | – |
| 1028 | – | – | – | – | – | – |
| 1045 | – | – | +/– (23) | – | – | – |
| 1070 | +/– (92) | – (22) | + (100) | + (96) | +/– (86) | ++ (350) |

– = <48% inhibition of syncytia
+/– = ≧49% and <80% inhibition of syncytia
+ = ≧50% inhibition of syncytia, titer 1:10
++ = ≧80% inhibition of syncytia, titer 1:20

Figure 20:
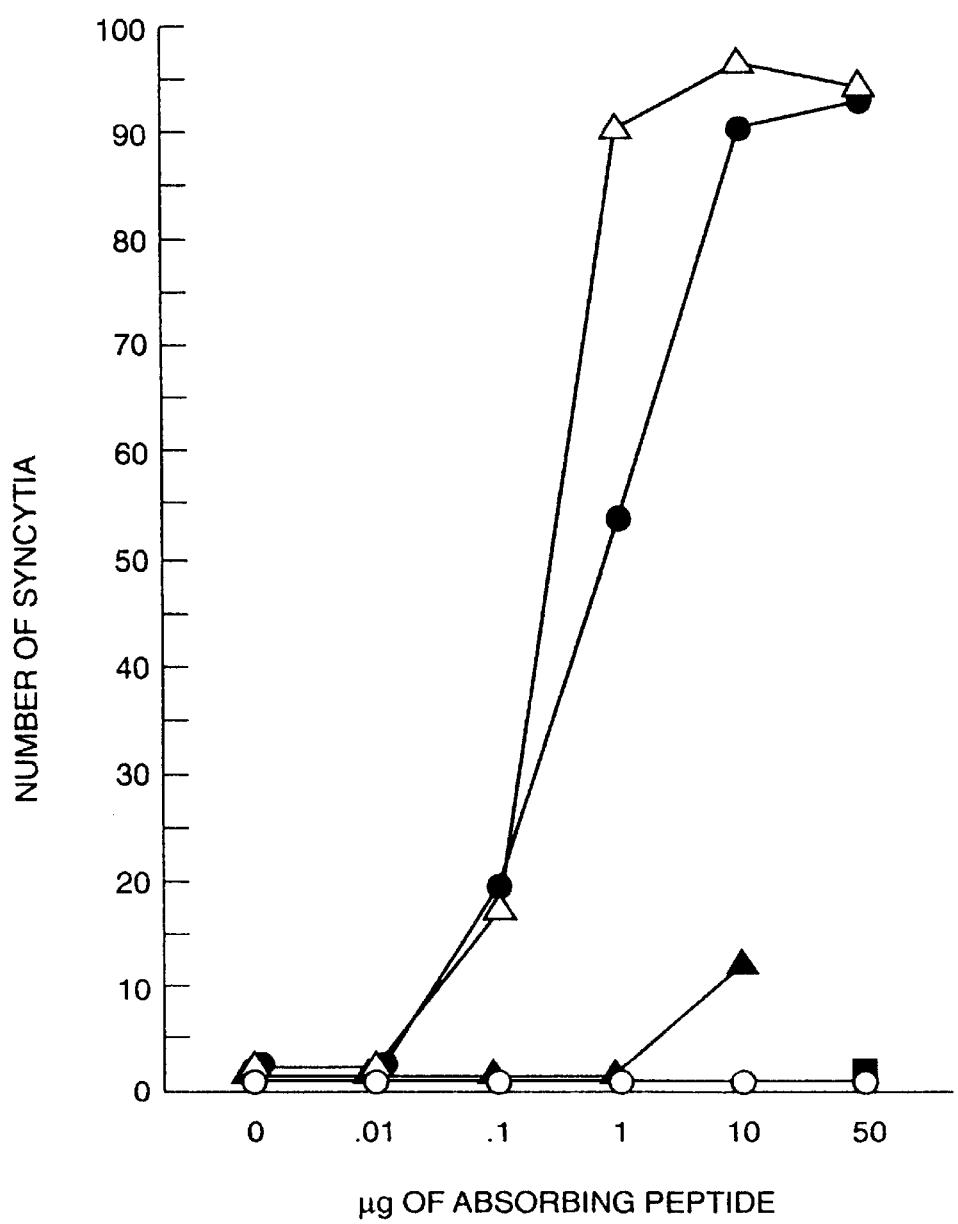
FIG. 20. Absorption of chimpanzee 1070 serum neutralizing antibodies against the HIV MN isolate by SP10MN(A) peptides and partial absorption by DP2 peptide.
Figure 21:
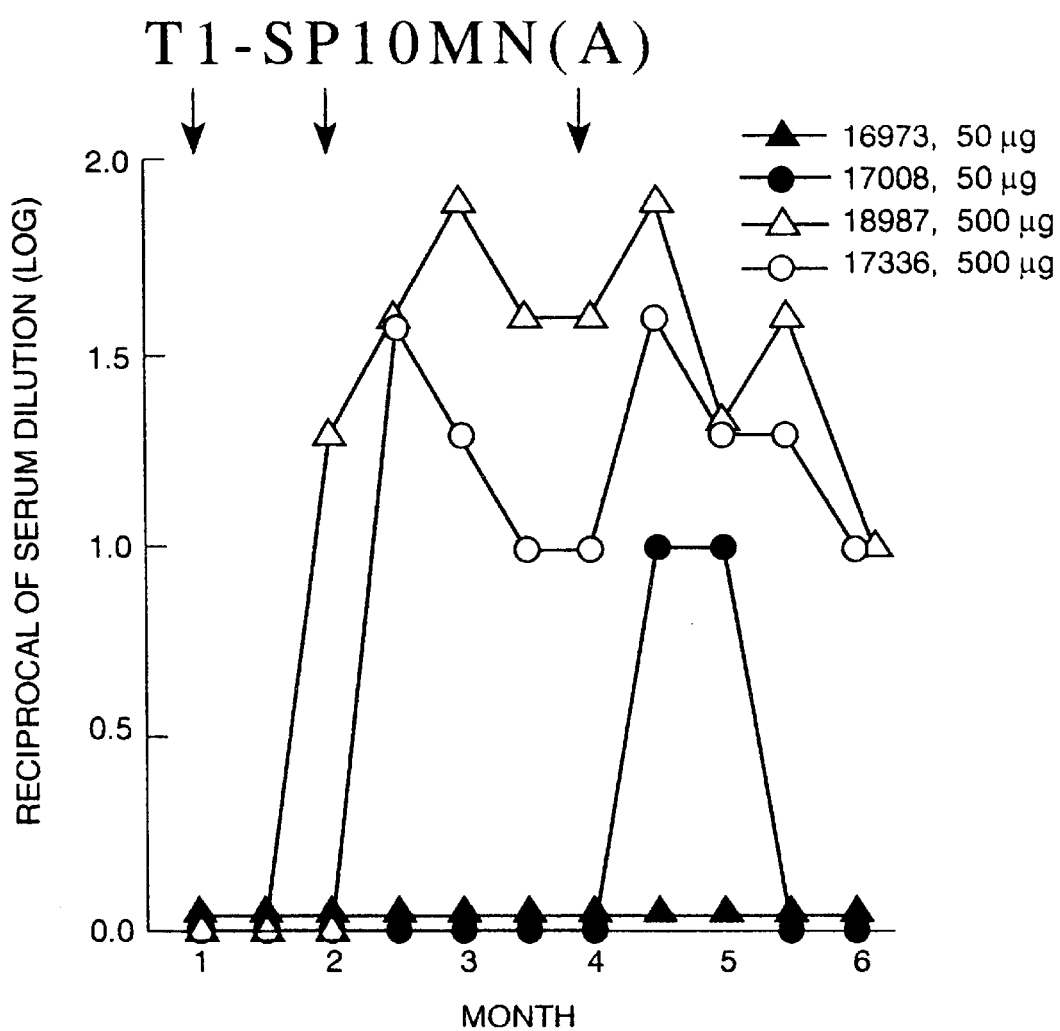
FIG. 21. Induction of high levels of neutralizing antibodies against HIV MN with T1-SP10MN(A) peptide in Rhesus monkeys.
Figure 22:
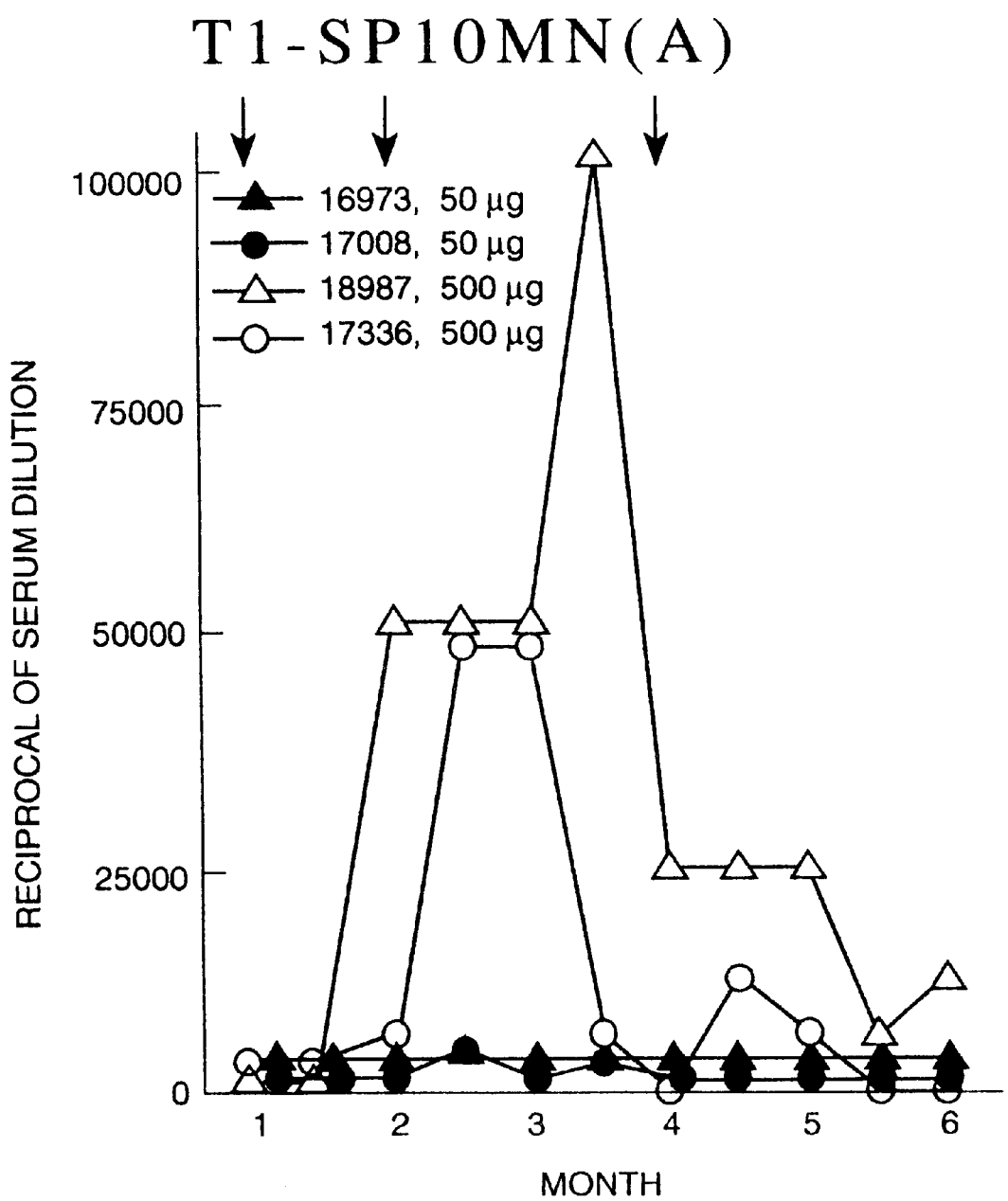
FIG. 22. Induction of anti-T1-SP10MN(A) peptide antibodies with T1-SP10MN(A) peptide in Rhesus monkeys.
Figure 23:
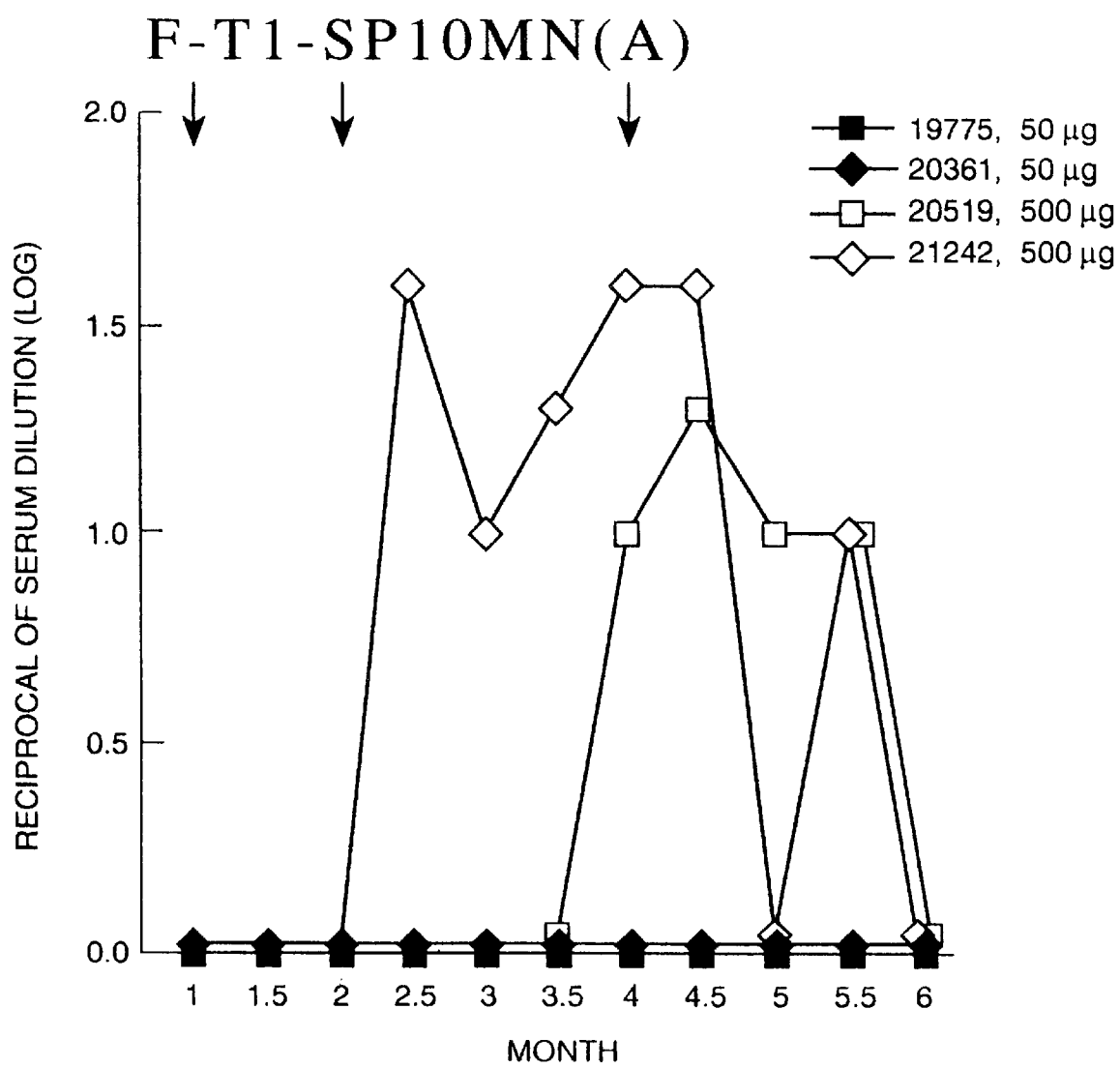
FIG. 23. Induction of high levels of anti-HIV MN neutralizing antibodies with T1-SP10MN(A) peptide.
Figure 24:
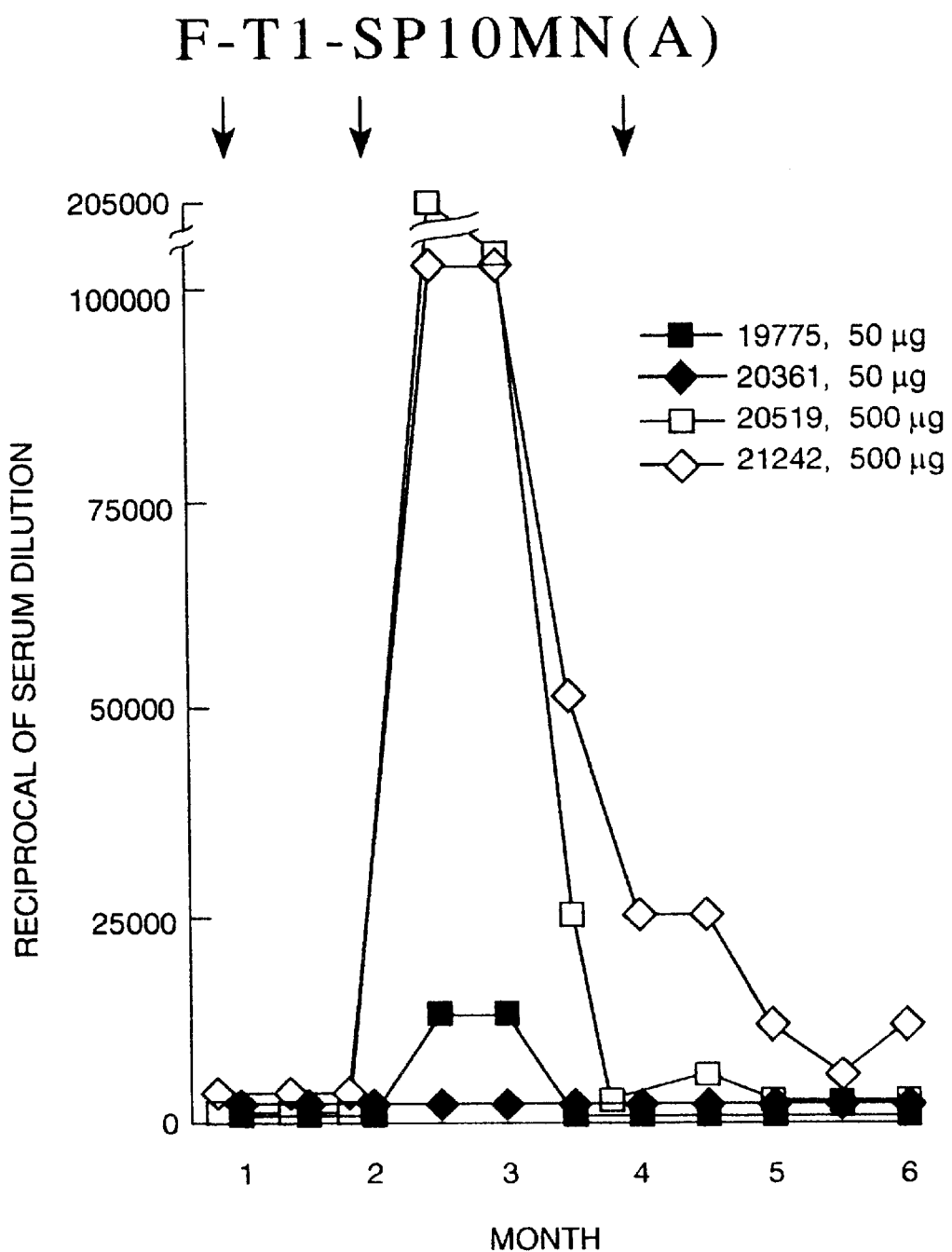
FIG. 24. Induction of antibodies against F-T1-SP10MN (A) peptide using F-T1-SP10MN(A) peptide as immunogen in Rhesus monkeys. Assay used in FIGS. 22, 24 was end-point ELISA against immunizing peptide (E/C greater than 2.9).

The observation that neutralizing antibodies in chimpanzee 1070 neutralized both HIV MN and IIIB isolates could be due to the presence of either type-specific neutralizing antibodies induced by both HIV MN and HIV IIIB peptides (Rusche et al Proc. Natl. Acad. Sci. USA 95:3198 (1988)), or be due to the induction of cross-neutralizing anti-GPGRA antibodies by the T1-SP10MN(A) peptides. Antibody titers against a truncated SP10IIIB peptide, SP10D, IRIQRGPGR, was used in ELISA assay with serum from chimpanzee 1070. End-point ELISA titers against this peptide were 1:800 or less from Oct. 23, 1990 through Dec. 3, 1991 (months 3 through 17 of study). Following the first immunization of animal 1070 with T1-SP10MN(A) on Dec. 3, 1992, the titers of antibody to SP10D peptide rose from 1:800 to 1:3200 on Jan. 7, 1992 and 1:12,800 on Feb. 4, 1992. During the same time period, antibody titers of 1070 to T1-SP10MN(A) peptide rose from 1:12,800 to 1:102,400, while titers to the T1-SP10IIIB peptide rose from 1:3200 to 1:25,600. Absorption studies to absorb out the neutralizing antibodies in animal 1070 serum demonstrated that all of the anti-HIV MN neutralizing activity could be absorbed out with the SP10MN(A) peptide, and part of the HIV MN neutralizing activity could be absorbed out with a peptide with the sequence IGPGRAIGPGRAIGPGRAC (DP2) (Jahaverian et al Science, 250:1590 (1990)) that only contains sequences from the tip of the V3 loop that are common to both HIV MN and HIV IIIB (FIG. 20). Thus, a portion of the chimpanzee antibody response induced by T1-SP10MN (A) peptides cross-neutralize HIV MN and HIV IIIB and are directed against the conserved sequences at the tip of the HIV gp120 V3 loop.

Figure 25:
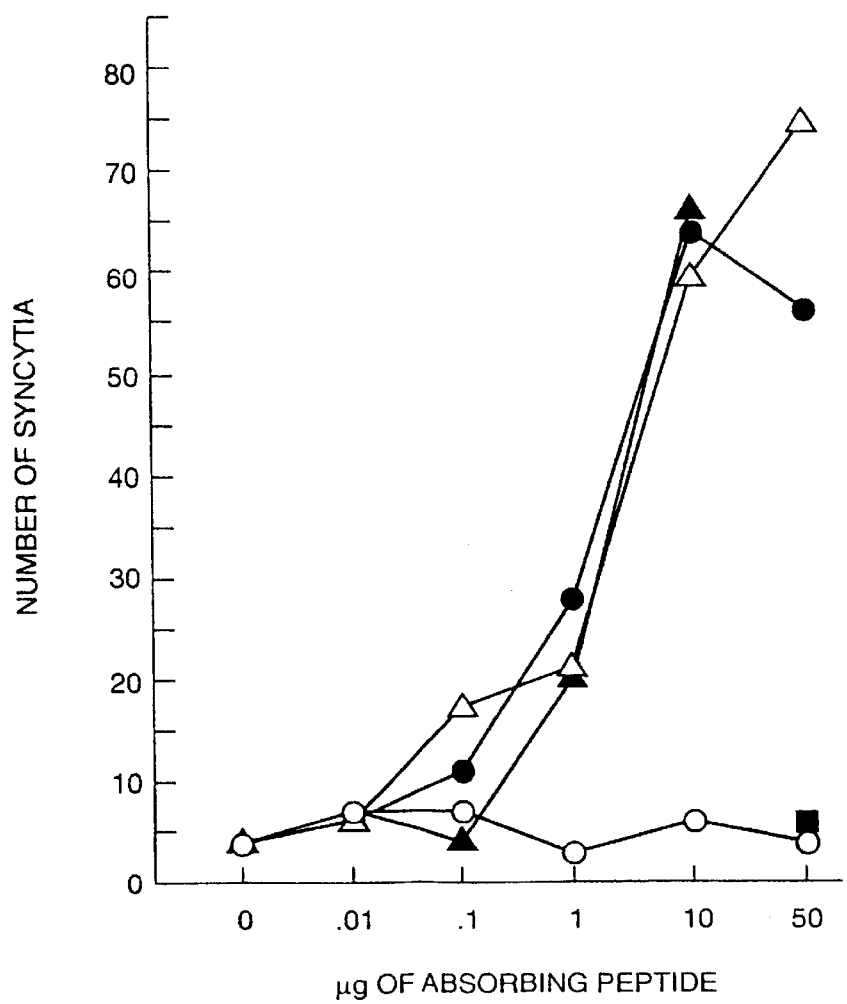
FIG. 25. Absorption of serum neutralizing antibodies against the HIV IIIB isolate by SP10MN(A) and DP2 peptides.

Importantly, in rhesus monkeys it was demonstrated that injection of 500 ug of purified T1SP10MN(A) peptides yielded very high levels of anti-HIVMN neutralizing antibodies in 4/4 animals (FIGS. 20–24) and in 1 of 4 rhesus monkeys, yielded cross-reactive anti-HIV neutralizing antibodies that neutralized the HIVIIIB and HIVMN viruses (Tables XVIII and XX). FIG. 25 shows that the DP2 (IGPGRAIGPGRAIGPFRAC) peptide absorbs the anti-HIVIIIB neutralizing activity in serum from rhesus monkey 18987. Table XXI shows the sequences of peptides used in the chimpanzee and rhesus monkey studies described.

TABLE XX

Cross Neutralization of HIV LAI/IIIB In RT Inhibition Assay By Immune Rhesus Monkey Sera From Animals Immunized with T1-SP10 Peptides

| | Animal No. | | | |
|---|---|---|---|---|
| | 18987 | | 17336 | |
| | LAI/IIIB | MN | LAI/IIIB | MN |
| Date | (Titer in RT Inhibition) | | | |
| 09-18-91 | 0 | 0 | ND | 0 |
| 10-30-91 | 1,430 | 330 | ND | 40 |
| 11-13-91 | 1,400 | 1,400 | ND | 400 |
| 12-18-91 | 350 | 1,450 | 0 | 360 |

TABLE XXI

Variants of T1-SP10 Peptides Derived From HIV MN and IIIB Envelope Sequences

| | Region | | | |
|---|---|---|---|---|
| Peptide Name | F | T1 | SP10 | A |
| HIV MN | | | | |
| TI-SP10MN(A) | | KQIINMWQEVGKAMYACTRPNYNKRKRIHIGPGRAFYTTX | | |
| F-T1-SP10MN(A) | AVGIGALFLGFLKQIINMWQEVGKAMYACTRPNYNKRKRIHIGPGRAFTTTX | | | |
| HIVIIIB | | | | |
| T1-SP10IIIB | | KQIINMWQIVGKAMYACTRPNNHTRKSIRIQRGPG | | |
| T1-SP10IIIB(A) | | KQIINMWQEVGKAMYACTRPNNNTRKSIRIQRGPGRAFVTI | | |
| F-T1-SP10IIIB(A) | AVGIGALFLGFLKQIINMWQEVGKAMYACTRPNNNTRKSIRIQRGPGKAFVTI | | | |

EXAMPLE 10

The following is a protocol for human patient immunization. HIV seronegative subjects will be immunized with a polyvalent mixture of T1SP10(A) peptides (see Tables XXII and XXIII) designed to generate neutralizing antibodies to about 80% of the current HIV isolates in the United States.

TABLE XXII

Sequence of Truncated T1-SP10(A) Peptides For Human Immunization

| | |
|---|---|
| KQIINMWQEVGKAMYARKRIHIGPGRAFYTTK | T1-SP10MN(A)-1T |
| KQIINMWQEYGKAMYARKSITKGPGRVIYATG | T1-SP10RF(A)-1T |
| KQIINMWQEVGKAMYARKSIPIGPGRAFIATS | T1-SP10EV91(A)-1T |
| KQIINMWQEYGKAMYARKSIHMGPGKAFYTTG | T1-SP10Can0A(A)-1T |

TABLE XXIII

Sequence of Full Length T1-SP10(A) Peptides For Human Immunization

| | |
|---|---|
| KQIINMWQEVGKAMYACTRPNYNKRKRIHIGPGRAFYTTK | T1-SP10MN(A) |
| KQIINMWQEVGKAMYACTRPNNNTRKSITKGPGRVIYATG | T1-SP10RF(A) |
| KQIINMWQEVGKAMYACTRPGNNTRKSIPIGPGRAFIATS | T1-SP10EV91(A)- |
| KQIINMWQEVGKAMYACTRPHNNTRKSIHMGPGKAFYTTG | T1-SP10Can0A(A) |

Experimental Protocol

Human patients, both HLA 2A+ and HLA 2A−, will be studied for up to two years. During treatment, the generation of neutralizing antibodies against HIVMN and other HIV isolates as well as the generation of T helper and/or Class I-restricted anti-HIV CTL will be measured.

The immunogens to be used will be T1SP10(A) peptides which are expected to give rise to antibodies against 80% of the HIV isolates in the Los Alamos Data Set (Myers et al., *Human Retroviruses and AIDS* 1991). Some patients will receive the immunogens in Table XX and some will receive the immunogens in Table XIX.

Each patient will receive as immunogen dose about 0.05 mg/kg/peptide or 1 mg of each peptide. If no responses to the original dose schedule result, the dose will be doubled and the regimen repeated after a three month rest.

Incomplete Freund's adjuvant (IFA) will be mixed with the immunogen in a 1:1 v/v mixture (Hart et al., *J. Immunol.*, 145:2677–2685, 1990). Total volume for each immunization should be 2 cc.

The immunogens will be administered by IM. The immunogens will be mixed in a total volume of 2 c and given IM, 1 cc in each of two sites (right or left upper arm, right or left thigh).

Immunizations will be given at 0 month, 1 month and 3 months. The patients will be monitored 4 weeks after each immunization. After the third immunization, the titer of responses to HIV will be tested and a decision made regarding immunization with a larger dose of peptide to begin after a three month rest.

Routine blood and urine tests will be conducted on the patients. The following blood samples will be required.

Serum (10 ml) (approximately 20 cc blood) will be used to study T1SP10 and SP10 peptide binding in RIA and HIV gp120 binding in RIP/Western blot assays. Serum will also be used to determine neutralization titers of HTLV-IIIB, HTLV-IIMN and field HIV isolates in reverse transcriptase and/or syncytium inhibition assays. Routine serum chemistries for toxicity (liver function tests, renal functions and chem 18 panel) and a complete blood count (10 cc heparinized blood) will be performed.

Peripheral blood cells (60 ml blood) will be used to study T cell proliferative responses to PHA, TT candidate T1SP10 and SP10 peptides, gp120 and OKT3 (about 30 ml heparinized blood). T cell, B cell, NK cell, CD4 and CD8 cell numbers will also be measured (about 5 ml heparinized blood). Finally, CTL assays will be performed on autologous or HLA-identical EBV-transformed B cell lines or autologous EBV-transformed B cell lines using vaccinia gp160 infected targets and peptide coated targets.

EXAMPLE 11

Figure 30:
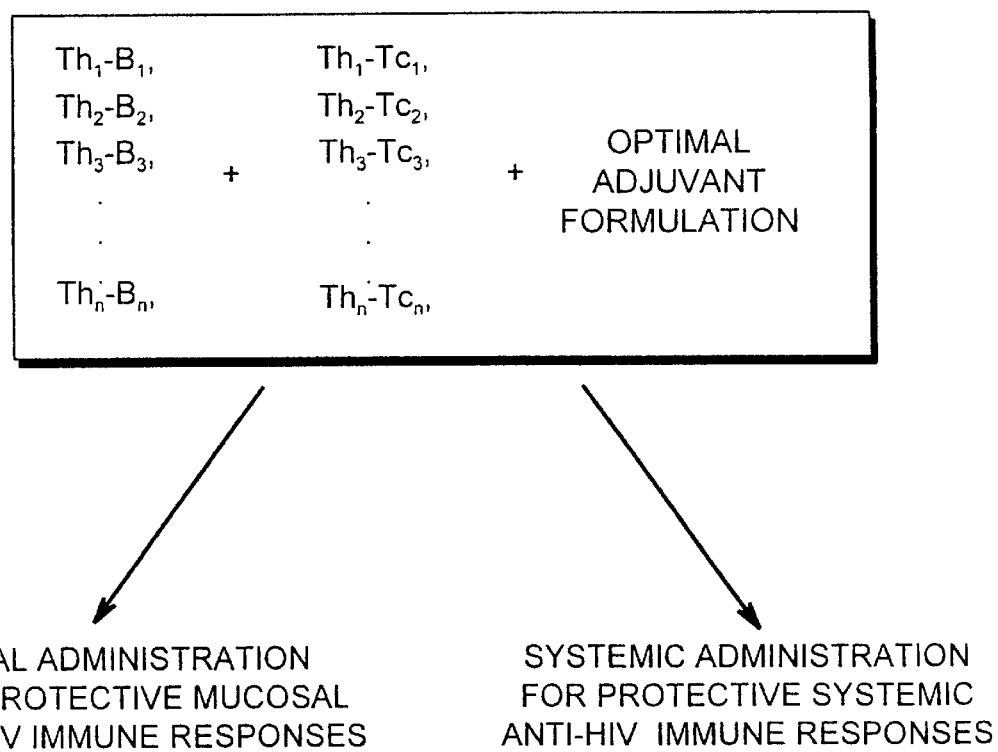
FIG. 30. General scheme for an HLA-based vaccine for AIDS.

A strategy has been developed for the design of experimental synthetic peptide immunogens for induction of T helper (Th) cells, neutralizing antibodies, and MHC Class I-restricted cytotoxic T lymphocytes (CTL) against HIV native proteins or HIV protein-expressing target cells (Palker et al, Proc. Natl. Acad. Sci. USA 85:1932 (1988), Palker et al, J. Immunol. 142:3612 (1989), Hart et al, J. Immunol. 145:2677 (1990), Hart et al, Proc. Natl. Acad. Sci. USA 88:9448 (1991), Haynes et al, AIDS Res. & Human Retroviruses 6:38 (1990), Haynes et al, J. Immunol. 151:1646 (1993), Haynes et al, J. Exp. Med. 177:717 (1993), Haynes et al, Trans. Amer. Assoc. Physician 106:31 (1993), Yasutomi et al, J. Immunol. 151:5096 (1993)). (A general scheme for an HLA-based vaccine for AIDS is set forth in FIG. 30. $Th_{1...n}$-$B_{1...n}$ includes the construct Th-SP10 and, by example, C4-V3. $Th_{1...n}$-$Tc_{1...n}$ is equivalent to Th-CTL (CTL=X)).

Figures 26A, 26B:
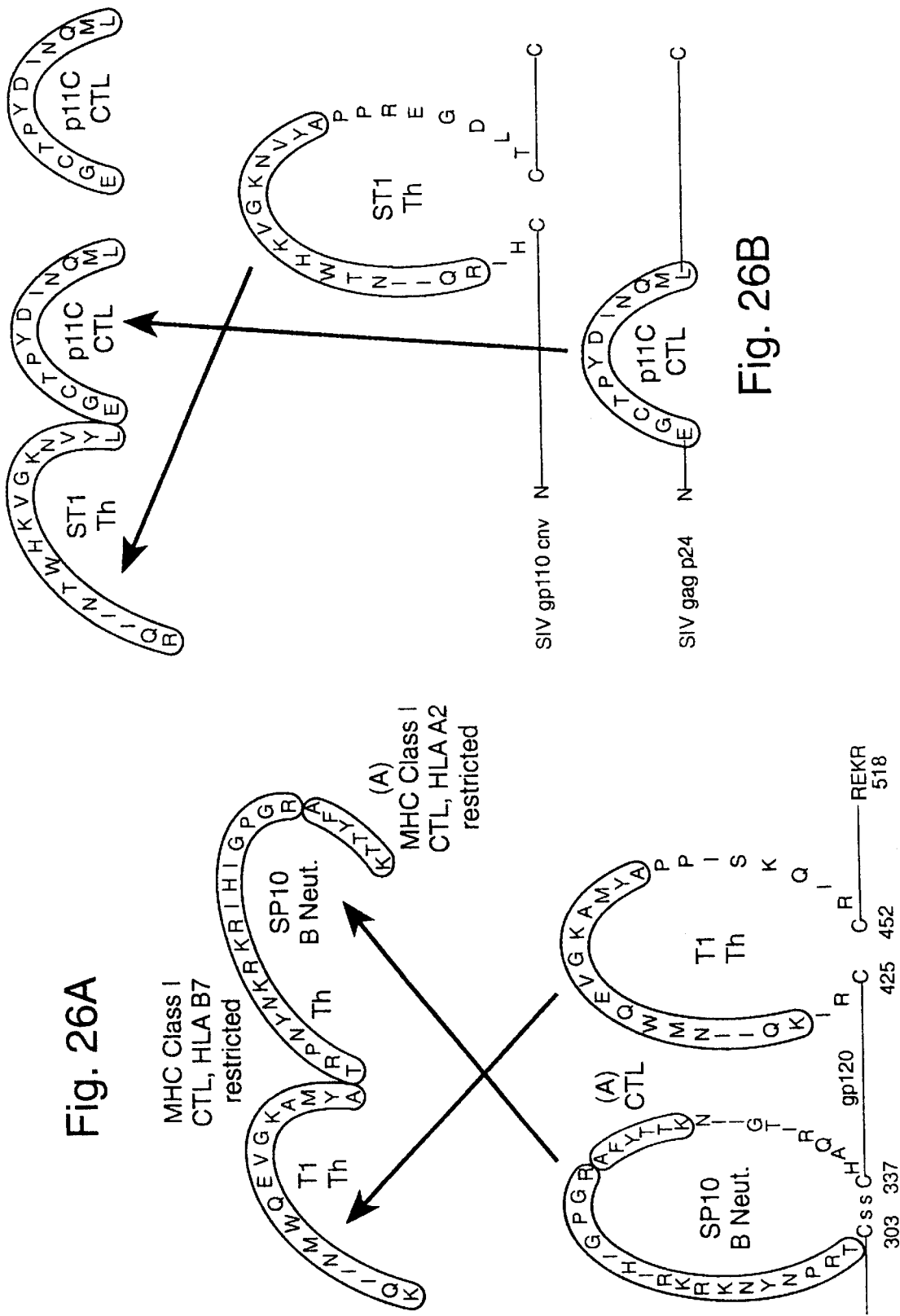
FIG. 26. Panel A is a general prototype design of the C4-V3 peptide called T1-SP10(A) from the HIV isolate MN with 2 T helper determinants in the hybrid peptide, one MHC Class I CTL epitope restricted by B7, and a second CTL epitome restricted by HLA-A2. Panel B shows the Th-CTL peptide designed from simian immunodeficiency virus envelope and simian immunodeficiency virus gag protein. This peptide was used to show the ability of the peptide to generate Class I restricted anti-SIV CTL in primates as described in Yasutomi et al (J. Immunol. 151:5096 (1993)).

A general immunogen design for induction of neutralizing antibodies requires the synthesis of one or more Th epitopes of HIV proteins N-terminal to the gp120 envelope V3 loop neutralizing domain (Th-B, FIG. 26). For MHC Class I-restricted anti-HIV or anti-SIV CTL induction, both Th-B-CTL and Th-CTL peptide designs have been successful (FIG. 26) (Hart et al, Proc. Natl. Acad. Sci. USA 88:9448 (1991), Yasutomi et al, J. Immunol. 151:5096 (1993)). Prototype synthetic peptide immunogens comprised of Th-B-CTL epitopes of HIVIIIB, MN or RF env gp120 have: a) induced Th responses to native gp120 in mice, goats, rhesus monkeys and chimpanzees (Palker et al, Proc. Natl. Acad. Sci. USA 85:1932 (1988), Palker et al, J. Immunol. 142:3612 (1989), Hart et al, J. Immunol. 145:2677 (1990), Haynes et al, J. Exp. Med. 177:717 (1993)) and b) induced in goats, rhesus monkeys and chimpanzees B cell neutralizing antibody responses that have neutralized laboratory HIV isolates in a type-specific manner (Palker et al, Proc. Natl. Acad. Sci. USA 85:1932 (1988), Palker et al, J. Immunol. 142:3612 (1989), Hart et al, J. Immunol. 145:2677 (1990), Haynes et al, J. Immunol. 151:1646 (1993), Haynes et al, J. Exp. Med. 177:717 (1993), Haynes et al, Trans. Amer. Assoc. Physician 106:31 (1993)) and c) induced in mice and rhesus monkeys anti-HIV or SIV MHC Class I-restricted CTL that kill target cells expressiong HIV or SIV proteins (Hart et al, Proc. Natl. Acad. Sci. USA 88:9448 (1991), Yasutomi et al, J. Immunol. 151:5096 (1993)). In rhesus monkeys, it has been demonstrated that the T1-SP10MN(A) peptide induced in select animals antibodies that reacted primarily with the IGPGRAF sequence at the tip of the V3 loop, and cross-neutralized HIVIIIB, HIVMN, HIVRF as well as HIV primary isolates grown in CEM cells (Haynes et al, J. Immunol. 151:1646 (1993)).

Design of a Prototype Polyvalent HIV Immunogen

Because of the extreme variability that exists in HIV isolates both in geographic locations and among patients, a multivalent HIV immunogen design tailored to HIV isolates in specific geographic locations, will likely be required for successful preventive and therapeutic HIV immunogens (Palker et al, J. Immunol. 142:3612 (1989), Haynes et al, Trans. Amer. Assoc. Physician 106:31 (1993)). To this end, a prototype polyvalent HIV immunogen has been designed containing Th-B-CTL epitopes reflective of 4 common HIV isolate motifs in Clave E, HIVMN, HIVRF, HIVEV91, and HIVCANO (FIGS. 26 and 27). In each of these prototype peptides resides at least two Th determinants, two Class I-restricted CTL determinants, one restricted by HLA A2 and A3 (Clerici et al, Nature 339:383 (1989)) and another restricted by B7 (Safrit et al, Characterization of HLA-B7-Restricted cytotoxic T lymphocyte clones specific for the third variable region HIV gp120, isolated from two patients during acute seronversion. Presented at the 6th NCVDG meeting Oct. 30–Nov. 4, 1993)), and three or more epitopes recognized by anti-HIV neutralizing antibodies (Palker et al, Proc. Natl. Acad. Sci. USA 85:1932 (1988), Rusche et al, Proc. Natl. Acad. Sci. USA 85:3198 (1988), Jahavarian et al, Science 250:1590 (1990)) (FIGS. 26 and 27). Preclinial studies of this prototype peptide mixture in mice have demonstrated that two of the components [T1-SP10RF(A) and T1-SP10EV91(A)] induced type-specific anti-V3 peptide [anti-SP10(A)] responses (Table XXIV), while two of the components [T1-SP10MN(A) and T1-SP10CANO(A)] induced broadly cross-reactive anti-V3 peptide antibody response (Table XXIV).

TABLE XXIV

Ability of HIV Envelope gp120 Synthetic Peptides To Induce
Anti-Peptide Antibodies After Three Immunizations

|  | Synthetic Peptides Used In ELISA Assays | | | |
|---|---|---|---|---|
| Synthetic Peptides Used To Immunize | T1-SP10MN(A) | T1-SP10RF(A) | T1-SP10EV91(A) | T1-SP10CANO(A) |
| Mice | (Geometric Mean Titers) | | | |
| Multivalent Peptide Mixture | 51,200 | 16,127 | 51,200 | 204,800 |
| T1-SP10MN(A) | 25,600 | 8,063 | 12,800 | 20,319 |
| T1-SP10RF(A) | 43 | 10,159 | 5 | 9 |
| T1-SP10EV91(A) | 12 | 5 | 2,016 | 0 |
| T1-SP10CANO(A) | 25,600 | 10,159 | 25,600 | 204,800 |

Balb/c mice were immunized three with 50 ug of monovalent peptides subcutaneously in IFA (Seppic ISA 51). Animals were bled 2 weeks after the immunization, and antibody titers determined using end-point ELISA assays (E/C 3.0). Data represent the geometric mean titers of serum antibodies of three mice for each point.
Eliza method are described in Haynes et al, J. Immunol. 151:1646 (1993), Haynes et al, J. Exp. Med. 177:717 (1993), Haynes et al, Trans. Amer. Assoc. Physician 106:31 (1993).

Ability of HIV Env Peptides to Induce Cross-Reactive Peptide Responses to African (Clave A) and Thailand (Clave E) HIV Isolate V3 Loop Peptides In addition, sera from goats and mice immunized with mixtures of all 4 peptides (Table XXV), contained antibodies that also cross-reacted with the T1-SP10(A)A. con. peptide (a Th-B-CTL peptide reflective of the consensus V3 loop sequence of Clave A in Africa), and to a lesser extent, with the T1-SP10(A)E.con. peptide (a Th-B-CTL peptide reflective of the consensus V3 loop sequence of Clave E in Thailand (Table XXV). When sera from mice immunized with only one of each of the 4 components of the polyvalent mixture were tested for their ability to bind to the African T1-SP10(A)A.con. peptide, it was found that the T1-SP10CANO(A) peptide was responsible for generating all of the cross-reactive antibodies to the African Clave A consensus sequence. Thus, although the primary V3 sequences of the CANO envelope is widely disparate from other HIV env V3 sequences (FIG. 27), secondary and possibly higher order structures of the V3 loop of the HIVCANO isolate appear to have the ability to induce cross-reactive anti-V3 antibodies against many different HIV V3 motifs.

TABLE XXV

Ability of Th-B HIV Env Polyvalent Peptide Mixture To Prime and Boost Mouse
and Goat Serum Antibodies That Cross-React With The Th-B Peptide With V3
Clave A (VHIGPGQAFYAT) Consensus Sequences

|  | Th-B Peptide V3 Sequence | | | | | |
|---|---|---|---|---|---|---|
|  | MN | RF | EV91 | CanO | A. Con. | E. Con. |
| Animals | Geometric Mean Titers | | | | | |
| Mouse | 51,200 | 16,200 | 51,200 | 204,800 | 81,100 | 1,600 |
| Goat | 25,600 | 18,000 | 12,800 | 25,600 | 28,600 | 4,500 |

Data represent the geometric mean titers of either 3 mice or 2 goats injected with the polyvalent Th-B HIVenv peptide mixture.
Method used are described in Haynes et al, J. Immunol. 151:1646 (1993), Haynes et al, J. Exp. Med. 177:717 (1993), Haynes et al, Trans. Amer. Assoc. Physician 106:31 (1993).
T1-SP10(A) SEQUENCES FOR AFRICAN (A.CON) AND SOUTHEAST ASIAN (E.CON) HIV ISOLATES

T1 SP10 A

| | |
|---|---|
| KQIINMWQRVGQAMYATRPNNNTRKSVHIGPGQAFYATGDI | T1-SP10(A)A.con |
| KQHNMWQGAGQAMYATRPSNNTRTSITIGPGQVFYRTGDI | T1-SP10(A)E.con |

Human Retroviruses and AIDS 1993.
edited by G. Myers, J. A. Berzofsky, B. Korber, R. F. Smith, and G. N. Pavlakis
published by the Theoretical Biology and Biophysics Group T-10
Mail Stop K710
Los Alamos National Laboratory
Los Alamos, NM 87545

Neutralizing Antibody Responses Generated by the Polyvalent HIV Env Immunogen Regarding neutralizing antibody responses, sera from animals immunized with the polyvalent immunogen (FIG. 27) bind to HIV gp120IIIB and gp120SF2 in either radioimmunoprecipitation assay or in ELISA assay. Sera from these animals have neutralized HIVMN and RF isolates in syncytium inhibition assays.

Demonstration of a Neutralizing CD4-V3 Conformational Determinant in HIV gp120

Figure 28:
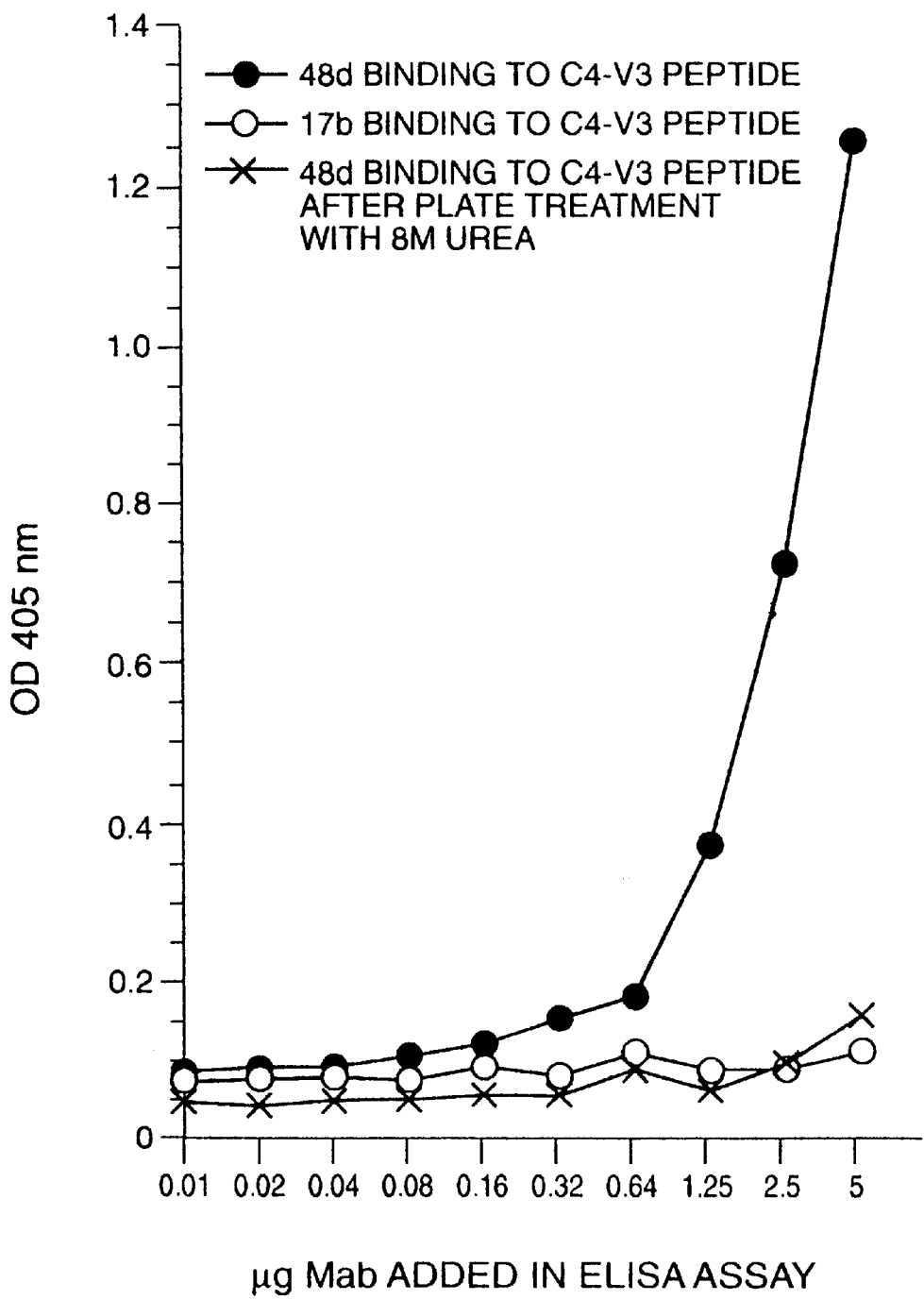
FIG. 28. Mab 48d binds to the C4-V3 peptide T1-SP10CANO(A) whereas monoclonal antibody 17b does not. Increasing amounts of monoclonal antibodies were added to ELISA plates on which the T1-SP10CANO(A) C4-V3 peptide was coated (2 μg/well) as described in detail in Haynes et al (J. Immunol. 151:1646 (1993), J. Exp. Med. 177:717 (1993)).
Figure 29:
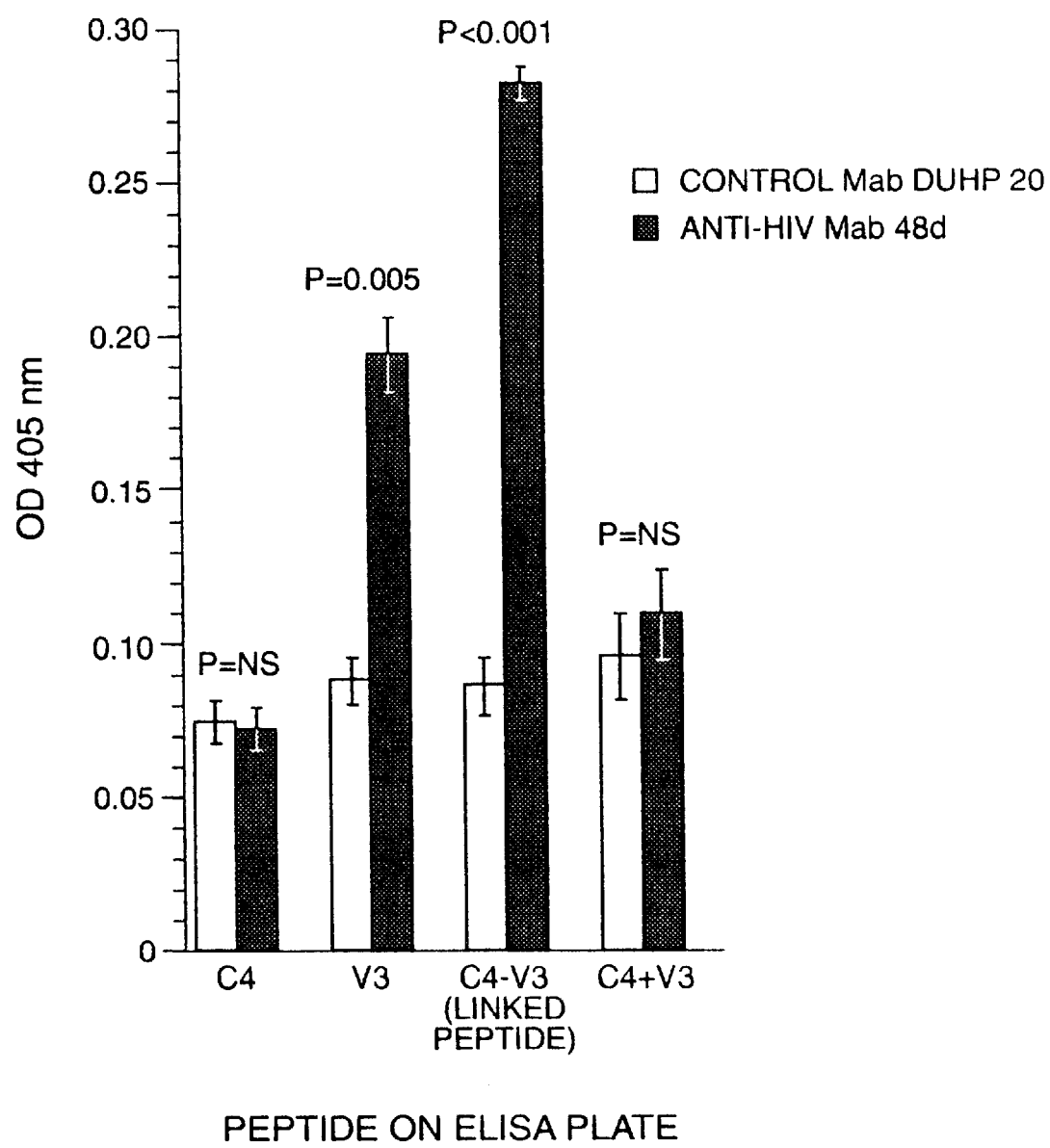
FIG. 29. The whole T1-SP10CANO(A) peptide is required for maximal peptide binding to mab 48d. Either the T1 peptide (C4 region alone) the V3 peptide [SP10CANO (A)], C4-V3 peptide [T1-SP10CANO(A)] or a mixture of equal amounts of C4 (T1)+V3[SP10CANO(A)] peptide were incubated on an ELISA plate with the total concentration of 2 μg/well. It can be seen in FIG. 29 that control monoclonal antibodies DU.HP20 did not bind to any of these peptides, whereas the 48d mabs bound to SP10CANO (A) peptide and significantly better to the C4-V3 version of the T1-SP10CANO(A) peptide. Mixing the T1+the SP10CANO(A) peptide together did not increase 48d binding.

The 17b and 48d human anti-gp120 mabs were isolated from human PBMC B cells from patients infected with HIV (Thali et al, J. Virol. 67:3978–3988 (1993); Moore et al, AIDS Res. Human. Retroviral. 9:1185 (1993)). The 17b and 48d mabs cross-block mouse mabs that block CD4 binding to gp120, broadly neutralize disparate HIV isolates, but do not in and of themselves block gp120-CD4 binding (Moore et al, personal communication, 1994; Thali et al, J. Virol. 67:3978 (1993)). Rather, binding of the 48d mab is upregulated to native gp120 following ligation of gp120 by CD4. It has been found that one peptide, T1-SP10CANO(A), binds to the 48d mab (FIG. 28), and the optimal binding of mab 48d to HIV env hybrid peptide T1-SP10CANO(A) depended on the presense of the CD4 peptide, T1 N-terminal to the SP10CANO(A) peptide (FIG. 29). Thus, the T1-SP10CANO(A) hybrid C4-V3 peptide mirrors a conformational determinant of HIV gp120 recognized by a potent broadly neutralizing human mab. It is interest that Wyatt et al, J. Virol. 66:6997 (1992) and Moore et al, J. Virol. 67:4785 (1993) have suggested that the V3 loop [SP10(A)] and the C4, T1 region are in close physical proximity to each other in native gp120. Thus, the present data directly demonstrate that the T1-SP10CANO(A) synthetic peptide can mimic broadly neutralizing C4-V3 conformational determinants of native gp120.

General Strategy for Identification of Multiple CD4-V3 [T1-SP10(A)] Peptides that Mirror Other HIV Isolate C4-V3 Conformational Determinants Whereas the HIV V3 loop by itself induces primarily type-specific anti-HIV neutralizing antibodies, the C4-V3 determinant as defined by the T1-SP10CANO(A) peptide will induce more broadly, cross-reactive neutralizing antibodies. This is known from the fact that the 48d human monoclonal antibody derived from a HIV seropositive patient binds to a complex conformational determinant on the surface of gp120, binds to a wide spectrum of HIV isolates and neutralizes disparate HIV isolates such as HIVIIIB and HIVMN (Thali et al, J. Virol. 67:3978 (1993); Moore, J. personal communication (1994)). Thus, a general strategy for identifying multiple C4-V3 peptides would be to construct a large number of C4-V3 peptides derived from C4 sequences (for example, from amino acids 419 to 428 from the HIVMN isolate and from homologous regions in other HIV isolates) linked N-terminal to SP10 or SP10(A) regions (such as amino acids 301–327 of HIVMN and from homologous regions in other HIV isolates) from sequences listed in the Los Alamos database (Human Retrovirus and AIDS, 1991, 1992, 1993 edited by G. Myers, J. A. Berzofsky, B. Korber, B. F. Smith and G. N. Pavlakis, published by the Theoretical Biology and Biophysic Group T-10, Mail Stop K710, Los Alamos National Laboratory, Los Alamos, N.M. 87545) (see Table XXVI for other examples). One would then screen approximately 40 to 100 of these different C4-V3 peptides against a combinatorial library of heavy and light chain immunoglobulin variable genes expressed on the surface of phage (Borbas et al, Proc. Natl. Acad. Sci. USA 88:7978 (1991)). The work of Borbas et al provides a method for screening a large number ($10^7$ to $10^8$) of human monoclonal antibodies derived from a patient with HIV infection making a screen possible of a wide spectrum of antibody responses to search for antibodies species against complex conformational determinants on gp120. Using this technology C4-V3 peptides can be identified that are in such a conformation to fit into the Fab notch of the variable region of the heavy and light chain heterodimer expressed in the combinatorial library on the surface of phage. These Fab monoclonals can be isolated and cloned (Borbas et al, Proc. Natl. Acad. Sci. USA, 88:7978 (1991)). Most importantly, C4-V3 peptide designs can be identified that reflect native gp120 C4-V3 conformational determinants of a wide variety of HIV strains. When this type of protein based selection is performed with combinatorial libraries derived from a large number of HIV-infected individuals from many different geographic sites of HIV infection around the world, a wide selection of C4-V3 peptides that mimic broadly reactive neutralizing determinants from the C4-V3 region of native gp120 can be identified and, for example, combined together with the T1-SP10CANO(A) prototype C4-V3 peptide into a multivalent C4-V3 peptide immunogen for induction of highly cross-reactive, broadly-neutralizing antibodies against C4-V3 conformational determinants of multiple HIV strains.

TABLE XXVI

C4-V3 Immunogen Constructs

| | T1 | SP10 | A |
|---|---|---|---|
| C4-V3 LAI | KQFINMWQEVGKAMYATRPNNNTRKSIRIQRGPGRAFVTIG | | |
| C4-V3 HXB2R | KQIINMWQKVGKAMYATRPNNNTRKSIRIQRGPGRAFVTIG | | |
| C4-V3 NL43 | KQFINMWQEVGKAMYATRPNNNTRKSIRIQRGPGRAFVTIG | | |
| C4-V3 MFA | KQFINMWQEVGKAMYATRPNNNTRKSIRIQRGPGRAFVTIG | | |
| C4-V3 MN | KQIINMWQEVGKAMYATRPNYNKRKRIHIGPGRAFYTTK | | |
| C4-V3 BRVA | KQIINMWQEVGKAMYATRPNNNTRKRITMGPGRVYYTTG | | |
| C4-V3 SC | KEIINMWQEVGKAMYATRPNNNTTRSIHIGPGRAFYATG | | |
| C4-V3 JH3 | KQIINMWQEVGKAMYATRPSKTTRRRIHIGPGRAFYTTR | | |
| C4-V3 ALA1 | KQIVNMWQEVGKAMYATRPNIYRKGRIHIGPGRAFHTTR | | |
| C4-V3 BAL1 | KQIINMWQEVGRAMYATRPNNNTRKSIHIGPGRAFYTTG | | |
| C4-V3 JRCSF | KQIINMWQEVGKAMYATRPSNNTRKSIHIGPGRAFYTTG | | |
| C4-V3 JRFL | KQIINMWQEVGKAMYATRPNNNTRKSIHIGPGRAFYTTG | | |
| C4-V3 OYI | KQIVNMWQEVGKAMYATRPNNNTRNRISIGPGRAFHTTK | | |
| C4-V3 SF2 | KQIINMWQEVGKAMYATRPNNNTRKSIYIGPGRAFHTTG | | |
| C4-V3 NY5CG | KQIINRWQEVGKAMYATRPNNNTRKGIAIGPGRTLYARE | | |
| C4-V3 SF162 | KQIINRWQEVGKAMYATRPNNNTRKSITIGPGRAFYATG | | |

TABLE XXVI-continued

C4-V3 Immunogen Constructs

| | T1 | SP10 | A |
|---|---|---|---|
| C4-V3 JFL | KQIINRWQEVGKAMYATRPNNNTRKSITLGPGRAFYTTG | | |
| C4-V3 CDC4 | KQIINRWQVVGKAMYATRPNNHTRKRVTLGPGRVWYTTG | | |
| C4-V3 SF33 | KQIINMWQEVGKAMYATRPNNNRRRRITSGPGKVWYTTG | | |
| C4-V3 HAN | KQIINMWQEVGKAMYATRPNNNTRKGIHIGPGRAVYTTG | | |
| C4-V3 ADA | KQIINMWQEVGKAMYATRPNNNTRKSIHIGPGRAFYTTG | | |
| C4-V3 WMJ2 | KQIINMWQGVGKAMYATRPYNNVRRSLSIGPGRAFRTRE | | |
| C4-V3 RF | KQIVNMWQEVGKAMYATRPNNNTRKSITKGPGRVIYATG | | |

Sequences taken from sequences taken from the Los Alamos Database, Human Retroviruses and AIDS 1991 edited by G. Myers, J. A. Berzofsky, B. Korber, R. F. Smith, and G. N. Pavlakis published by the Theoretical Biology and Biophysics Group T-10 Mail Stop K710, Los Alamos National Laboratory, Los Alamos, NM 87545

EXAMPLE 12

In the design of an HLA-based HIV vaccine, the following variables are taken into account: a) the HLA molecules that are expressed in the population or cohort to be immunized, b) the CTL or T helper epitopes present in the immunogen and their respective HLA-restricting elements, and c) the HIV variants present in the geographic location of the cohort to be vaccinated. An HLA-based vaccine for induction of anti-HIV T cell immunity is a multivalent mixture of immunogens reflective of the most common HIV variants in a geographic location, and containing immunogenic CTL and T helper epitopes that bind to the HLA molecules expressed on antigen-presenting cells of subjects of the cohort to be vaccinated. The mixture of immunogens can range from a mixture of non-HIV vectors expressing HIV proteins, to mixtures of HIV recombinant proteins and/or synthetic peptides (Palker et al, J. Immunol. 142:3612 (1989); Hart et al, Proc. Natl. Acad. Sci. USA 88:9448 (1991); Berzofsky, FASEB J. 5:2412 (1991); Haynes et al, Trans. Assoc. Amer. Phys. 106:33 (1993); Haynes et al, AIDS Res. Hum. Retroviral 11:211 (1995); Cease et al, Ann. Rev. Immunol. 12:923 (1994); Walfield et al, Vaccines 92, Cold Spring Harbor Laboratory Press pp. 211–215 (1992)).

Data sets that can be used to develop HLA-based AIDS vaccines include: 1) a compilation of CD8+ CTL and CD4+ T helper epitopes in HIV proteins that can be derived from the available literature (see particularly Nixon et al, Immunology 76:515 (1992)), 2) a listing of the HLA restricting antigens that present HIV CTL and T helper epitopes which also can be derived from the available literature, 3) a compilation of the HIV variants present in specific geographic locations that can be derived from the available literature (see particularly Human Retroviruses and AIDS 1993, Myers et al (eds) published by Theoretical Biology and Biophysics Group, Los Alamos National Laboratory, Los Alamos, N.M. 87545), and 4) a listing of HLA types for ethnic groups in geographic locations (HLA 1991 Tsuji et al (eds), Proceedings of the 11th International Histocompatibility Workshop and Conference, Oxford Unv. Press, Oxford, England 1992).

Table XXVI shows an HLA-based HIV vaccine design for CTL induction for African-Americans, and shows analyses of the most common HLA types present in the cohort to be immunized, the HLA Class I CTL epitopes restricted by the common HLA types in the cohort, and the HIV variants in the geographic location under consideration. The most useful HIV preventive immunogens will be those designed for all members of a cohort to be immunized in a geographic area regardless of ethnic background, and such immunogens can be designed by expanding the number of HLA types used in the analysis, and by choosing HIV CTL immunogenic epitopes presented by several disparate HLA molecules (see available literature including Haynes et al, AIDS Res. Human Retroviral. 11:211 (1995)). Since a number of HIV CTL epitopes are presented by more than one allotype of HLA Class I molecules, by using nine CTL epitopes (as well as variant peptides reflective of HIV mutations at these sites) 95% of African-Americans, 97.5% of Caucasian Americans, 97% of Native Americans and 99% of Thais can be expected to respond to such an HIV immunogen (see Table XXVII below) (Haynes et al, AIDS Res. Human Retroviral 11:211 (1995)).

TABLE XXVI

Steps in the Development of an HLA-Based Subunit HIV Vaccine For Induction of Anti-HIV CTL in African-Americans in the United States 1. Analysis of common MHC types in cohort to be immunized.
   Example: For African-Americans in the United States, 80% will express HLA A2, A3, A28, A30, B7, or B8.
2. Analysis of the HLA Class I HIV CTL epitopes restricted by these common HLA types in African-Americans in the cohort to be immunized.
   Example: For HLA-A2, aa77–85, from p17 gag (Johnson et al, J. Immunol. 147:1512 (1991)); for HLA-A3, aa73–82 from nef (Culmann et al, J. Immunol. 146:1560 (1991)); for HLA-A28, aa583–592, from gp41 (Lieberman et al, J. Immunol. 148:2738 (1992)); for HLA-A30, aa844–863, from gp41 (Lieberman et al, J. Immunol. 148:2738 (1992)) for HLA-B7, aa302–312, from gp120 McMichael et al, AIDS 85:S155 (1994)); for HLA-B8, aa586–593 from gp41 (Sutton et al, Eur. J. Immunol. 23:447 (1993)).
3. Analysis of the HIV clade variants in the geographic locations of the cohort to be immunized.
   Example: The most common clade in the United States and Western Europe is Clade B. For Clade B, epitope aa77–85 from p17, of 26 isolates analyzed in the Los Alamos database, these are 8 variants, necessitating including 8 peptides for this sequence. A similar analysis for the other 5 epitopes would require an additional 54 peptides, for a total of 62.
4. T cell help can be obtained for anti-HIV CTL induction by peptides by synthesizing immunodominant T helper determinants N terminal to the CTL epitopes or includsion of T helper determinants in larger subunits of HIV immunogens* (Palker et al, J. Immunol. 142:3612 (1989); Milich, Nature 329:547 (1987)).

TABLE XXVI-continued

| Steps in the Development of an HLA-Based Subunit HIV Vaccine For Induction of Anti-HIV CTL in African-Americans in the United States | |
|---|---|
| Example: | $Th_1$-$X_1$, $Th_2$-$X_2$, $Th_3$-$X_3$, $Th_N$-$X_N$, etc: where Th = immunodominant T helper epitopes and X = MHC Class I CTL epitopes. |

*Specific CTL epitopes are included because of the restricted nature of CTL-epitope presentation by HLA molecules (Palker et al, J. Immunol. 142:3612 (1989); Berzofsky, FASEB J. 5:2412 (1991); Berzofsky, Sem. Immunol. 3:203 (1991)). Only the most common immunodominant T helper epitopes need to be included for T cell help for CTL generation without regard to immunized cohort restriction element expression, since many HIV T helper epitopes are presented by multiple HLA Class II types (rev. in (Berzofsky, FASEB J. 5:2412 (1991); Berzofsky, Sem. Immunol. 3:203 (1991)), and some retrovirus CTL epitopes also been suggested to have T helper cell stimulating activity (rev. in Berzofsky, FASEB J. 5:2412 (1991); Berzofsky, Sem. Immunol. 3:203 (1991)).

It will be appreciated that the actual degree of HIV variability may not be reflected by the degree of variability seen in existing databases. It will also be appreciated that it is not certain that every variant of every HLA type will equally present each peptide to T cells. Further, it is not certain that every HIV CTL epitope variant will be a potent agonist and trigger T cells to an optimum anti-HIV immune response. However, vaccines designed in accordance with the present approach can be expected to be of significant clinical effectiveness. Further, for design of an HLA-based HIV preventive immunogen that induces both anti-HIV T cell responses and anti-HIV neutralizing antibodies, HIV B cell immunogens that induce broadly neutralizing antibodies for HIV primary isolates can be added to a multivalent HIV T cell immunogen.

le;2qBy way of example, set forth below is an HLA-based HIV vaccine formulated based on the International Histocompatibility Workshop data presented in Histocompatibility Testing 1994, Albert et al eds Springer-Verlag, Berlin (1994) and HLA 1991, 2 volumes, Tsuji et al (eds) Oxford University Press, Oxford England (1992)) supplemented with other published data (Williams et al, Human Immunol. 33:39 (1992); Chandanayingyong et al, HLA antigens in Thais, In Proceedings of the Second Asia and Oceania Histocompatibility Workshop Conference, Simons and Tait (eds) Immunopublishing Toorak pp. 276–87 (1983)). Using these data and the Hardy-Weinberg theorem (Hardy, Science 28:49 (1908)), an estimate was made of the proportion of each of four populations that would be expected to present peptides to the immune system if a limited number of HIV epitopes were included in a vaccine designed specifically for that population. Similar calculations were made for a vaccine designed to be immunogenic for all four populations. These results are presented in Table XXVII.

TABLE XXVII

| Population | HLA Restriction Elements Chosen | HIV Protein | Epitope Location | Epitope |
|---|---|---|---|---|
| a) African Americans | A2, A3, A11, B35 | nef | 73–82 | QVPLRPMTYK |
| | A28, B14 | gp41 | 583–592 | VERYLKDQQL |
| | A30, B8 | gp41 | 844–863 | RRIRQGLERALL |
| | B17, B37 | nef | 117–128 | TQGYFPQWQNYT |
| | Cw4 | gp120 | 576–583 | (S)FNCGGEFF |
| (Proportion of African Americans expected to present these 5 epitopes is 92.3%) | | | | |
| b) USA Caucasians | A2, A3, A11, B35 | nef | 73–82 | QVPLRPMTYK |
| | A30, B8 | gp41 | 844–863 | RRIRQGLERALL |
| | B7 | gp120 | 302–312 | RPNNNTRKSI |
| | or | nef | 126–138 | NYTPGPGVRYPLT |
| | B12 | p24 | 169–184 | IPMFSALSEGATPQDL |
| (Proportion of USA Caucasians expected to present these 4 epitopes is 90.2%) | | | | |
| c) North American Indians | A2, A3, A11, B35 | nef | 73–82 | QVPLRPMTYK |
| | A24 | gp41 | 584–591 | YLKDQQLL |
| | or | nef | 120–144 | YFPDWQNYTPGPGIRYPLTFGWCYK |
| | A31 | gp41 | 770–780 | RLRDLLLIVTR |
| (Proportion of North American Indians expected to present these 3 epitopes is 96.4%) | | | | |
| d) Thais | A2, A3, A11, B35 | nef | 73–82 | QVLRPMTYK |
| | A24 | gp41 | 584–591 | YLKDQQLL |
| | or | nef | 120–144 | YFPDWQNYTPGPGIRYPLTFGWCYK |
| (Proportion of Thais expected to present these 2 epitopes is 93.6%) | | | | |
| e) African Americans | A2, A3, A11, B35 | nef | 73–82 | QVPLRPMTYK |
| USA Caucasians | A28, B14 | gp41 | 583–592 | VERYLKDQQL |
| North American Indians | A30, B8 | gp41 | 844–863 | RRIRQGLERALL |
| Thais | B17, B37 | nef | 117–128 | TQGYFPQWQNYT |
| | Cw4 | gp120 | 376–383 | (S)FNCGGEFF |
| | B7 | gp120 | 302–312 | RPNNNTRKSI |
| | or | nef | 126–138 | NYTPGPGVRYPLT |
| | B12 | p24 | 169–184 | IPMFSALSEGATPQDL |
| | A31 | gp41 | 770–780 | RLRDLLLIVTR |
| | A24 | gp41 | 584–591 | YLKDQQLL |
| | or | nef | 120–144 | TFPDWQNYTPGPGIRYPLTFGWCYK |
| (Proportions of African Americans, USA Caucasians, North American Indians, and Thais expected to present these 9 epitopes are 95.4%, 97.5%, 99.4%, and 97.2%, respectively) | | | | |

The most frequent restriction elements in the population under consideration for vaccination (or common to the 4 populations) are first identified, peptides that are presented by more than one HLA allele are next identified, and commonality between the two lists is then determined. Probability calculations utilize the frequencies of the commonality alleles supplemented by those of additional high frequency alleles in the population. Alleles are added until the proportion of the individuals in the population carrying one or more of the alleles in the list is at an acceptable level, eg greater than 90%. The sum of the HLA gene frequencies that recognize the fewest number of different HIV peptides to be included in the HIV immunogen is thus maximized. The next step is to choose the peptides associated with the restricting allele. In some instances only one peptide is associated with an allele while in others, multiple peptides are presented by the same allele.

For the four population cohorts considered in this analysis, as few as 2 and as many as 5 epitopes are required to achieve a theoretical protection level of at least 90%. (Table XXVII). The different numbers of required epitopes reflect, in part, the relative amounts of HLA Class I polymorphism observed in the different ethnic groups and presentation of a peptide by multiple HLA class I molecules.

A comparison between the individual and combined population (Table XXVII) demonstrates that relatively little is gained by including epitopes that are associated with low frequence alleles. The proportion of individuals protected approaches 100% asymptotically so that even adding on epitopes associated with high frequency alleles adds little to the proportion as this level is approached. This is illustrated by the North American Indians where including 6 more epitopes associated with 5 very low frequency alleles and one intermediate frequency allele in the combined theoretical vaccine added only 3.0% protection.

All documents cited above are hereby incorporated in their entirety by reference.

The foregoing invention has been described in some detail by way of examples for purposes of clarity and understanding. It will be obvious to those skilled in the art from a reading of the disclosure that the synthetic peptides of the instant invention may differ slightly in amino acid sequence from the sequences of SP-10 regions of specific HIV isolates, without departing from the scope of the invention.

What is claimed is:

1. A peptide of the general formula

Th-SP10(X)

wherein:

Th represents an amino acid sequence comprising a T helper epitope;

SP10 represents a peptide consisting essentially of an amino acid sequence of up to about 35 units in length and corresponding to at least one antigenic determinant of the envelope glycoprotein of HIV recognized by B lymphocytes, said peptide being capable, when covalently linked to a carrier molecule, of inducing in a mammal the production of high titers of type-specific antibodies against HIV; and (X) represents an amino acid sequence corresponding to a HIV protein sequence recognized by MHC Class I or Class II restricted cytotoxic T cells.

2. A peptide of the general formula:

Th-SP10 wherein:

Th represents an amino acid sequence comprising a T helper epitope; and

SP10 represents a peptide consisting essentially of an amino acid sequence of up to about 35 units in length and corresponding to at least one antigenic determinant of the envelope glycoprotein of HIV recognized by B lymphocytes, said peptide being capable, when covalently linked to a carrier molecule, of inducing in a mammal the production of high titers of type-specific antibodies against HIV.

* * * * *